(12) United States Patent
Oberg et al.

(10) Patent No.: US 10,570,439 B2
(45) Date of Patent: *Feb. 25, 2020

(54) SAMPLE CONCENTRATION DEVICES

(71) Applicant: Monolythix, Inc., Camarillo, CA (US)

(72) Inventors: Keith A. Oberg, Camarillo, CA (US);
Anthony Spence, Camarillo, CA (US);
Ivan Rueda, Camarillo, CA (US);
Mark D. Dobbs, Camarillo, CA (US);
Milton Lee, Camarillo, CA (US)

(73) Assignees: Monolythix, Inc., Camarillo, CA (US);
Alfred E. Mann Foundation for Scientific Research, Santa Clarita, CA (US)

( * ) Notice: Subject to any disclaimer, the term of this patent is extended or adjusted under 35 U.S.C. 154(b) by 38 days.

This patent is subject to a terminal disclaimer.

(21) Appl. No.: 15/240,960

(22) Filed: Aug. 18, 2016

(65) Prior Publication Data

US 2017/0051273 A1  Feb. 23, 2017

Related U.S. Application Data

(60) Provisional application No. 62/206,749, filed on Aug. 18, 2015.

(51) Int. Cl.
| G01N 1/40 | (2006.01) |
| B01L 3/00 | (2006.01) |
| C12Q 1/6806 | (2018.01) |
| G01N 1/00 | (2006.01) |
| C12Q 1/68 | (2018.01) |

(52) U.S. Cl.
CPC .......... C12Q 1/6806 (2013.01); B01L 3/5023 (2013.01); G01N 1/405 (2013.01); B01L 2200/026 (2013.01); B01L 2300/069 (2013.01); B01L 2300/0832 (2013.01); B01L 2300/12 (2013.01); B01L 2400/0406 (2013.01)

(58) Field of Classification Search
CPC ...... C12Q 1/6806; C12Q 1/6802; C12Q 1/68; B01L 3/5023; B01L 3/502; B01L 3/50; G01N 1/405; G01N 1/40; G01N 1/02; G01N 1/00
USPC .................. 436/174; 422/947, 408, 401, 400
See application file for complete search history.

(56) References Cited

U.S. PATENT DOCUMENTS

| 5,728,457 | A | 3/1998 | Frechet et al. |
| 5,939,259 | A | 8/1999 | Harvey et al. |
| 6,887,384 | B1 | 5/2005 | Frechet et al. |
| 7,691,263 | B1 | 4/2010 | Gu |
| 7,846,383 | B2 | 12/2010 | Song |
| 7,867,780 | B2 | 1/2011 | Jones et al. |
| 8,703,058 | B1 | 4/2014 | Hatch |
| 2004/0101442 | A1 | 5/2004 | Frechet et al. |
| 2004/0161788 | A1 | 8/2004 | Chen et al. |
| 2005/0023456 | A1 | 2/2005 | Frechet et al. |
| 2005/0202427 | A1 | 9/2005 | Soufla |
| 2006/0040406 | A1 | 2/2006 | Jones et al. |
| 2008/0116137 | A1 | 5/2008 | Bonn et al. |
| 2010/0143905 | A1 | 6/2010 | Lane et al. |
| 2011/0033663 | A1 | 2/2011 | Svec et al. |
| 2012/0264116 | A1 | 10/2012 | Michlitsch |
| 2012/0276576 | A1 | 11/2012 | Haddad et al. |
| 2013/0139834 | A1 | 6/2013 | Karisson et al. |
| 2014/0017672 | A1 | 1/2014 | Holmberg et al. |
| 2014/0031952 | A1 | 1/2014 | Harshbarger et al. |
| 2014/0041462 | A1 | 2/2014 | Beerling et al. |
| 2014/0127669 | A1 | 5/2014 | Hilder et al. |
| 2014/0178252 | A1 | 6/2014 | Hatch et al. |
| 2014/0295415 | A1 | 10/2014 | Rolland et al. |
| 2014/0356874 | A1 | 12/2014 | Bearinger et al. |
| 2016/0047642 | A1 | 2/2016 | Zhou |
| 2016/0146714 | A1 | 5/2016 | Oberg et al. |

FOREIGN PATENT DOCUMENTS

| GB | 2477093 | 7/2011 |
| WO | 2005098439 | 10/2005 |
| WO | 2007120808 | 10/2007 |
| WO | 2008007359 | 1/2008 |
| WO | 2011082449 A1 | 7/2011 |
| WO | 2011137533 A1 | 11/2011 |
| WO | 2013006904 A1 | 1/2013 |

OTHER PUBLICATIONS

Bakry, Rania, et al., "Monolithic Porous Polymer Layer for the Separation of Peptides and Proteins Using Thin-Layer Chromatography Coupled with MALDI-TOF-MS", Analytical Chemistry, 2007, vol. 79; pp. 1-8.

Bhattacharyya, A., et al., "Thermoplastic Microfluidic Device for On-Chip Purification of Nucleic Acids for Disposable Diagnostics", Analytical Chemistry, Feb. 1, 2006, vol. 78, No. 3. pp. 738-792.

Chatterjee, Anirban, et al., "RNA Isolation from Mammalian Cells Using Porous Polymer Monoliths: An Approach for High-Throughput Automation", Analytical Chemistry, Jun. 1, 2010, vol. 82, No. 11, pp. 4344-4356.

Frechet, J., "Immobilization of Enzymes onto Porous Monolithic Polymer Supports to Facilitate Fabrication of Micro and Nanofactories", http://www.nsec.ohio.state.edu/briefs/immobilization.pdf, document created Feb. 14, 2008, 2 pages.

Millipore Corp., "Hi-Flow Plus Membranes and SureWick Pad Materials", Lit. No. PS1267EN00, Rev May 2008, Diagnostics-08-00087, 2008: pp. 1-10.

(Continued)

*Primary Examiner* — Christine T Mui
(74) *Attorney, Agent, or Firm* — Basil S. Krikelis; Michael J. DeGrazia

(57) ABSTRACT

The present disclosure relates to a concentrator for concentrating, purifying or otherwise isolating one or more target analytes in a fluid matrix, and related methods, using self-wicking materials, such as monoliths. The present disclosure can be used as a point-of need sample preparation device. The self-contained device can be used for the extraction and concentration of specific target molecules, such as nucleic acids.

33 Claims, 27 Drawing Sheets

(56) References Cited

OTHER PUBLICATIONS

Millipore Corp., "Rapid Lateral Flow Test Strips: Considerations for Product Development", lit. No. TB500EN00 Rev B May 2008, Diagnostics-08-00161, 2008, pp. 1-42.

Potter, Oscar G., et al., "Porous Polymer Monoliths for Extraction: Diverse Applications and Platforms", Journal of Separation Science, 2008, vol. 31, pp. 1881-1906.

Shkolnikov, Viktor, et al., "Design and Fabrication of Porous Polymer Wick Structures", Sensors and Actuators B Chemical, 2010, vol. 150, pp. 556-563.

Wong, Raphael C., et al., "Lateral Flow Immunoassay", ISBN 978-1-56829-908-6, e-ISBN 978-1-59745-240-3, DOI 10.1007/978-1-59745-240-3, Humana Press, 2009, pp. 1-223.

Bechtle, M., "Preparation of Macropourous Methacrylate-based Monoliths for Chromatographic Appications", Dissertation No. 18401, Institute for Chemical and Bioengineering, ETH Zurich, 2009, pp. 1-99.

International Search Report and Written Opinion relating to co-pending PCT Application No. PCT/US2016/047642 dated Aug. 18, 2015; 10 pages.

Supelco. (1998). Guide to Solid Phase Extraction. [Bulletin 910]. Bellefonte: Sigma-Aldrich. Retrieved from: <www.sigmaaldrich.com/Graphics/Supelco/objects/4600/4538.pdf>. (12 pages).

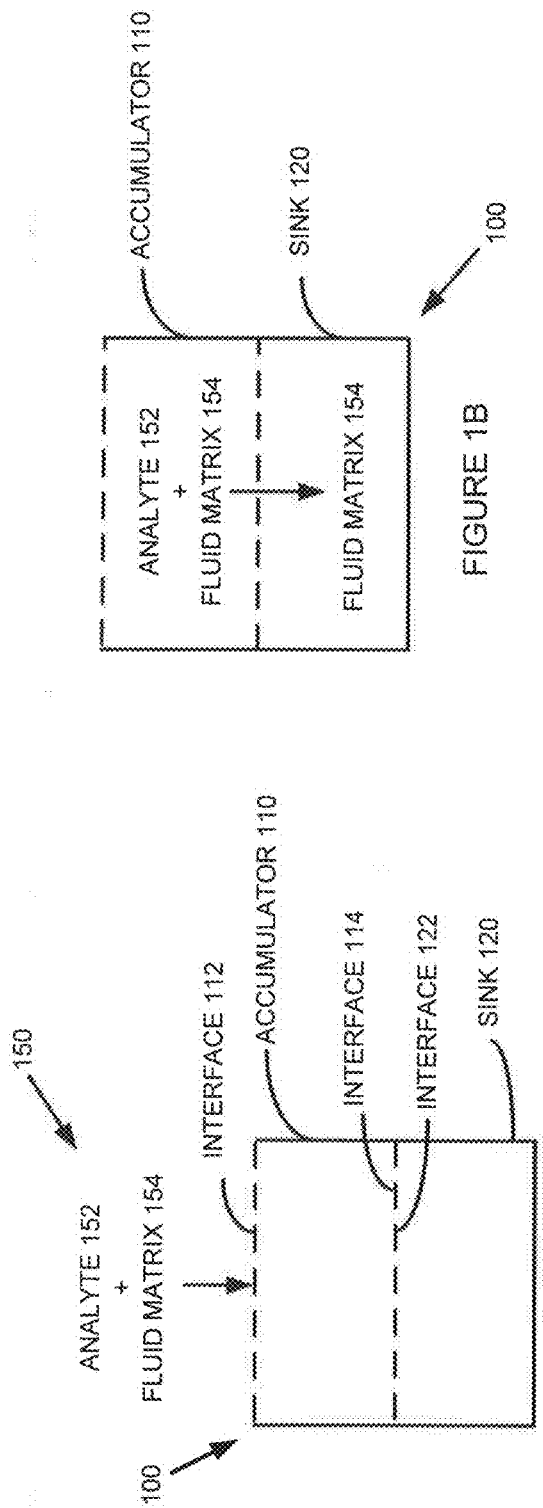
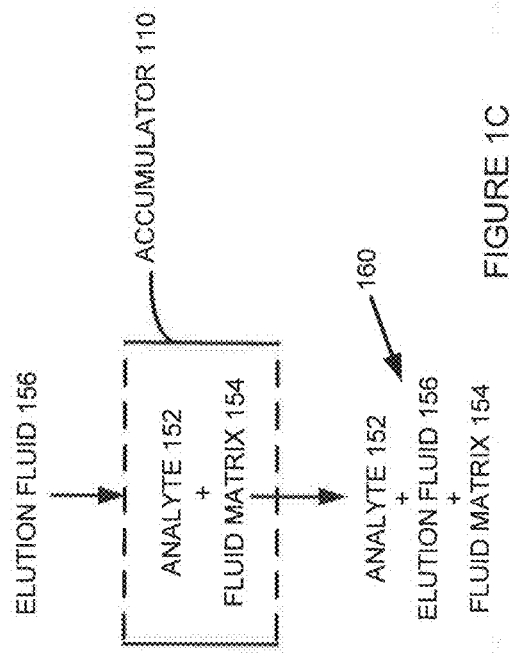

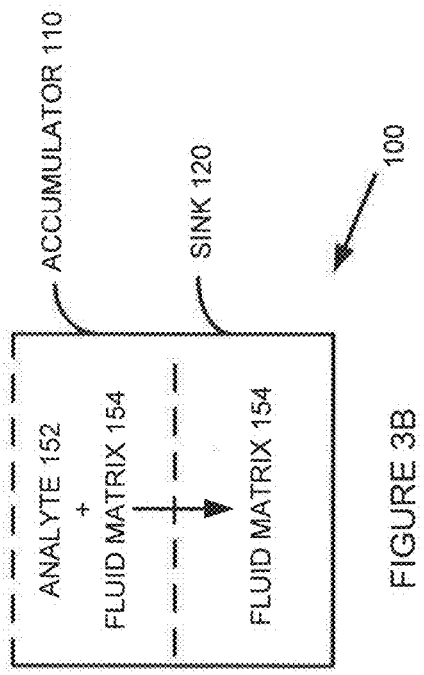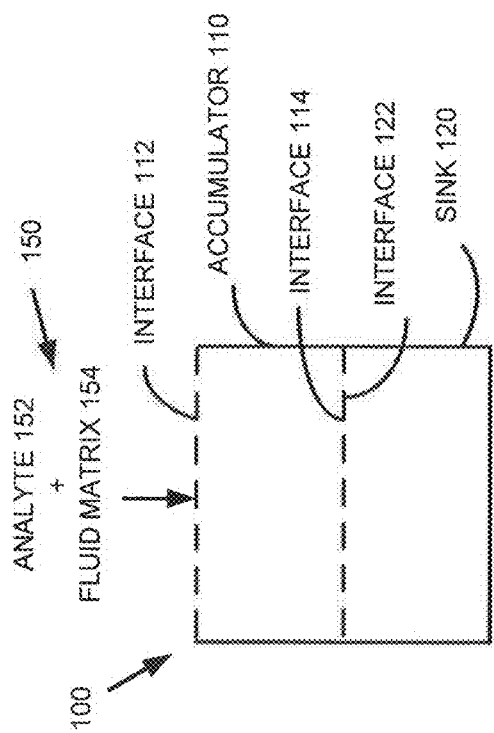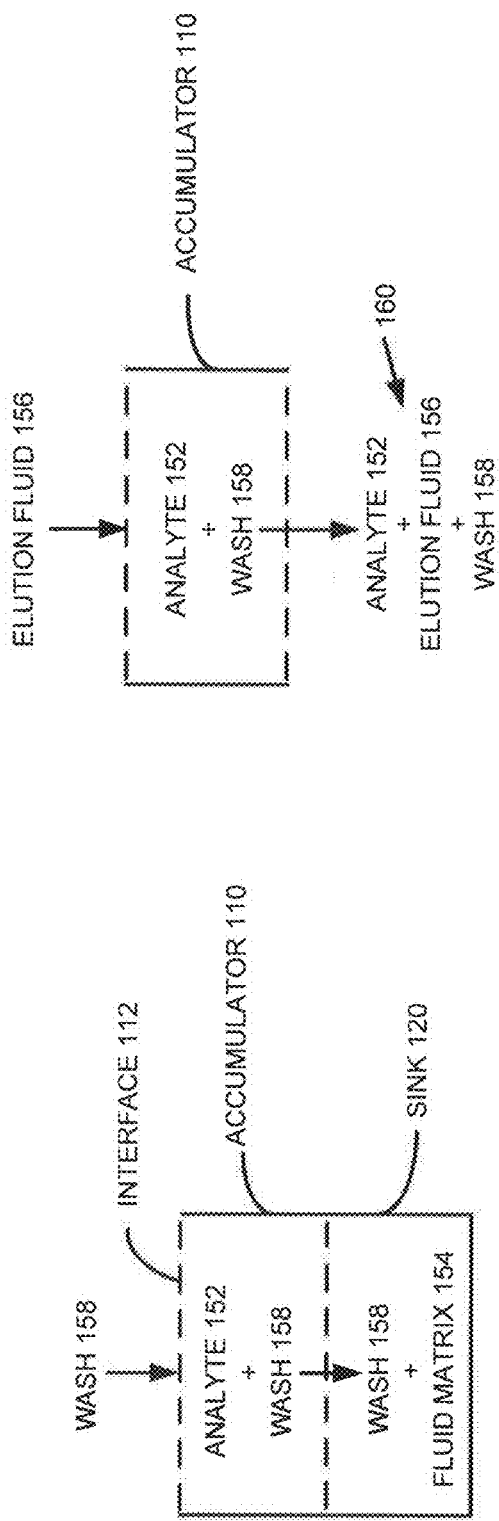

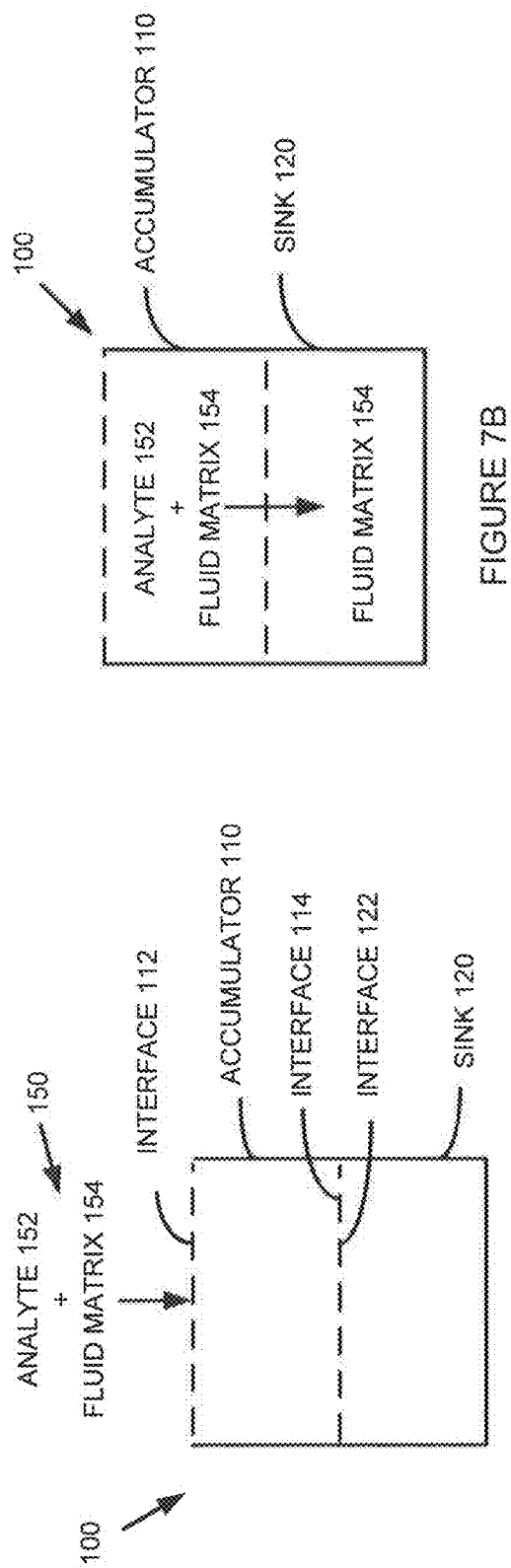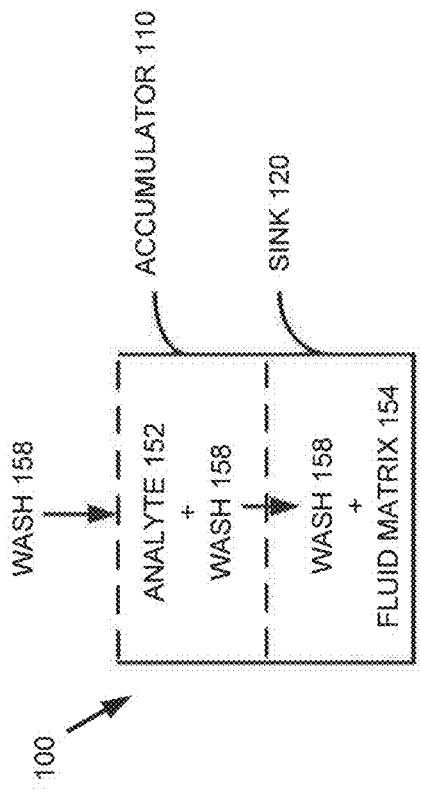
FIGURE 7A
FIGURE 7B
FIGURE 7C

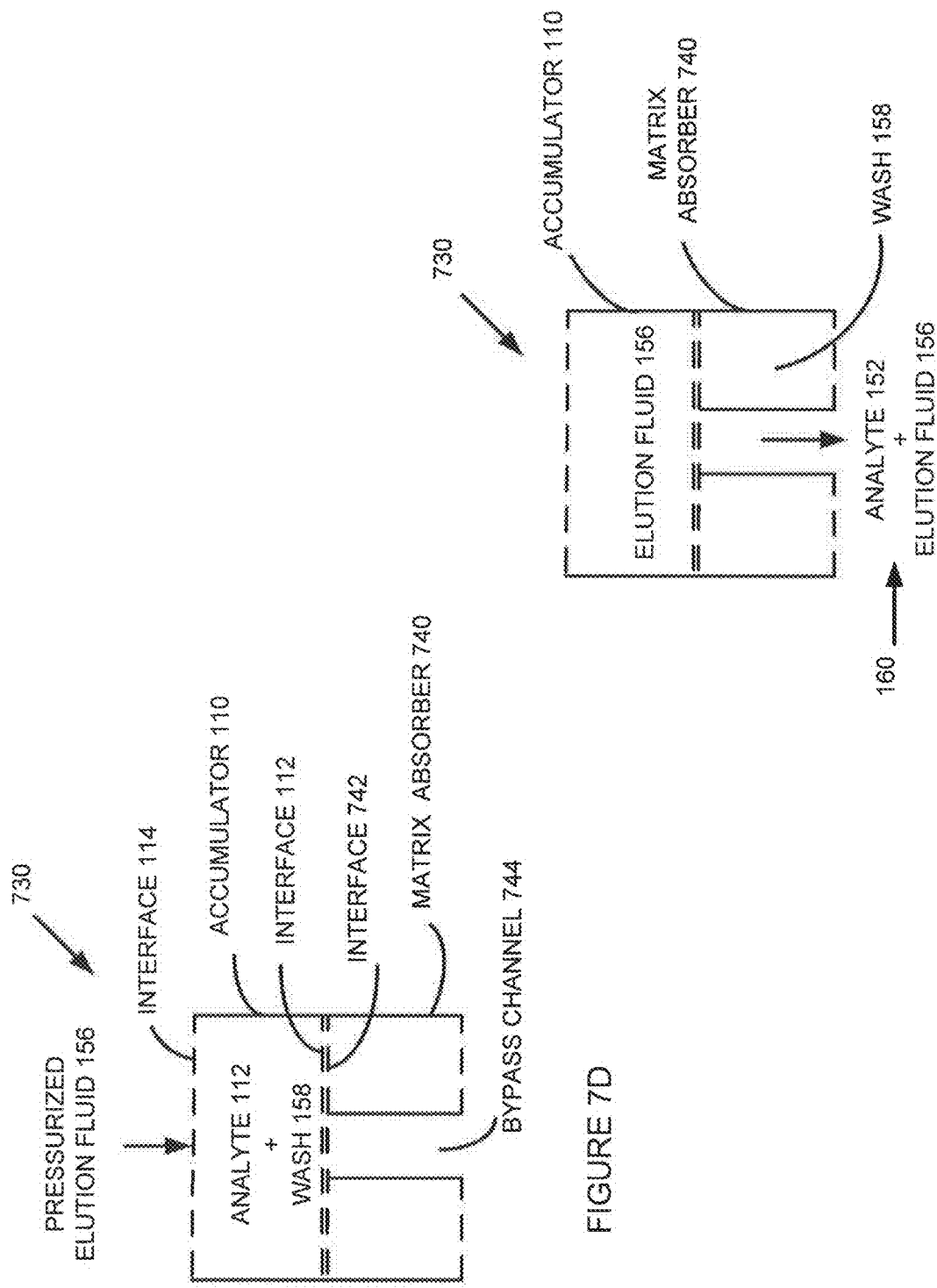

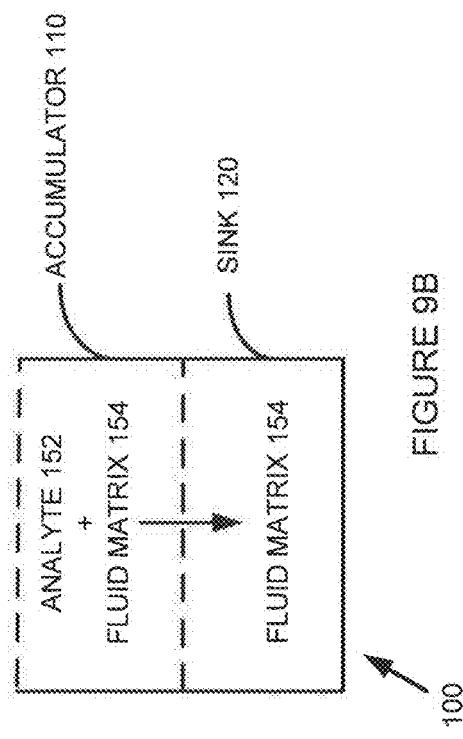
FIGURE 9B
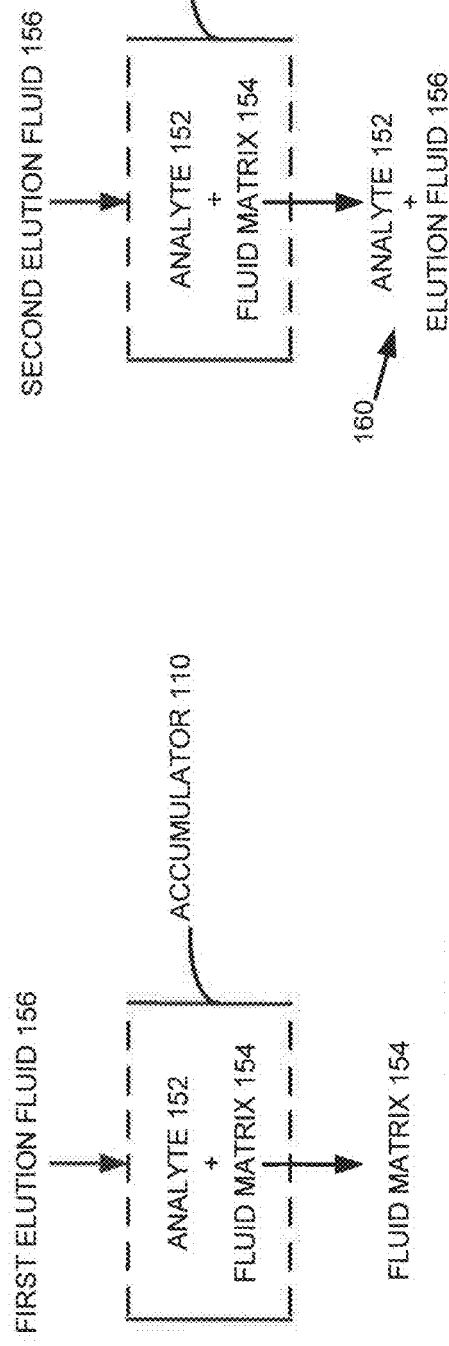
FIGURE 9D
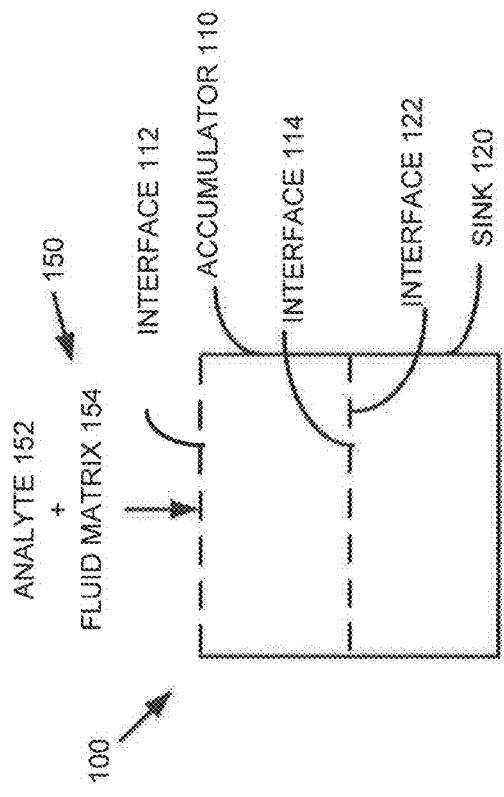
FIGURE 9A
FIGURE 9C

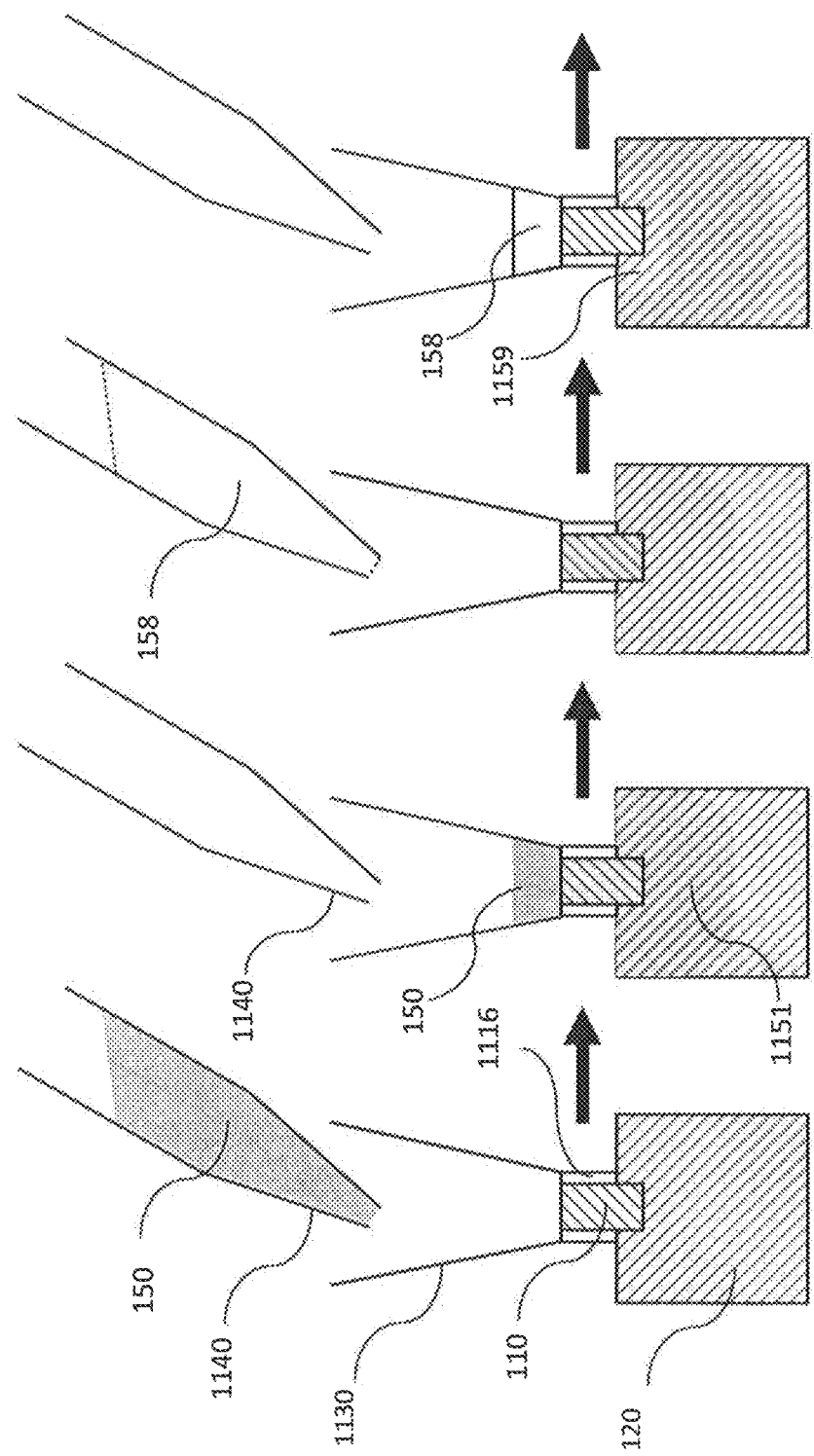

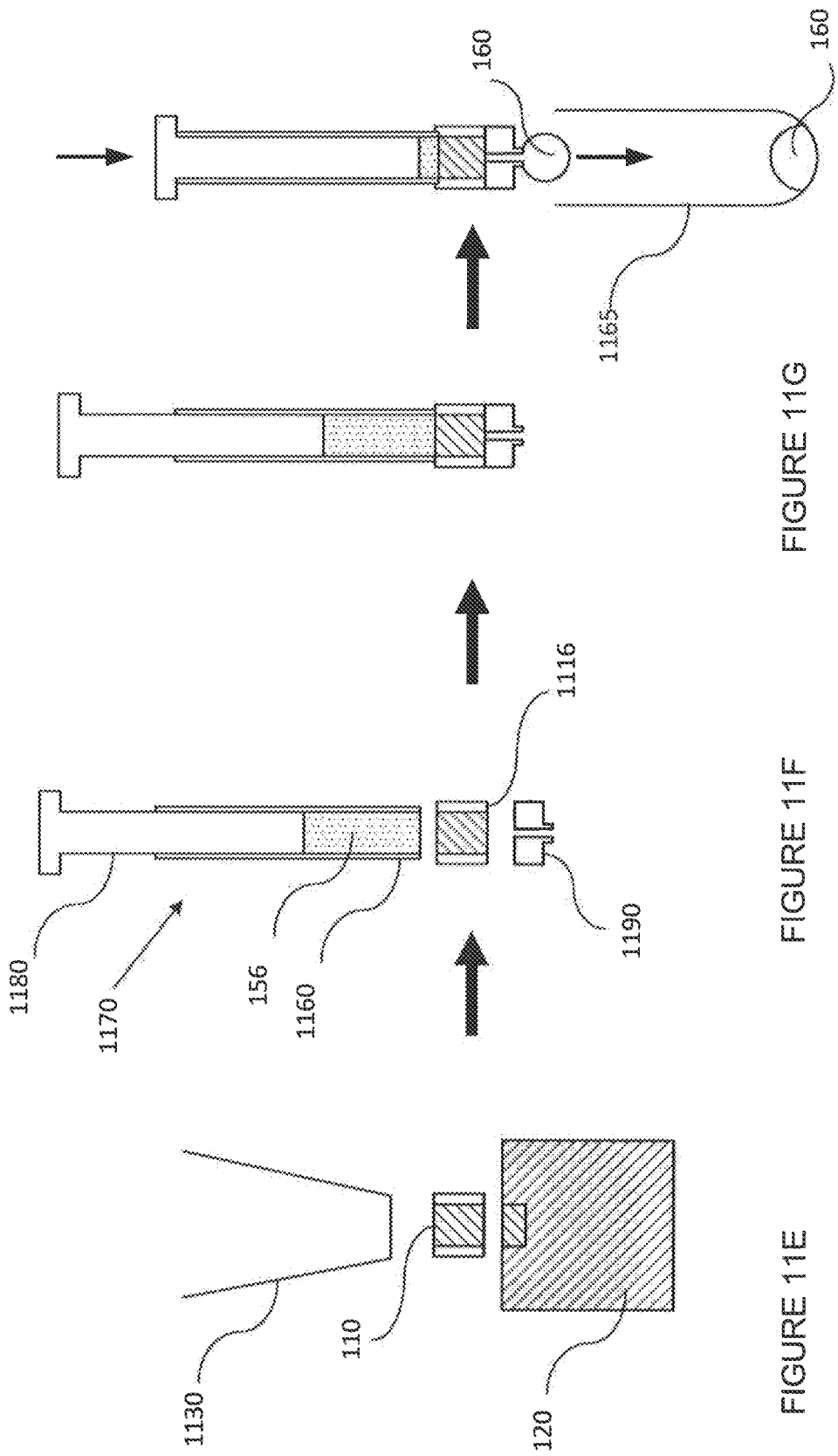

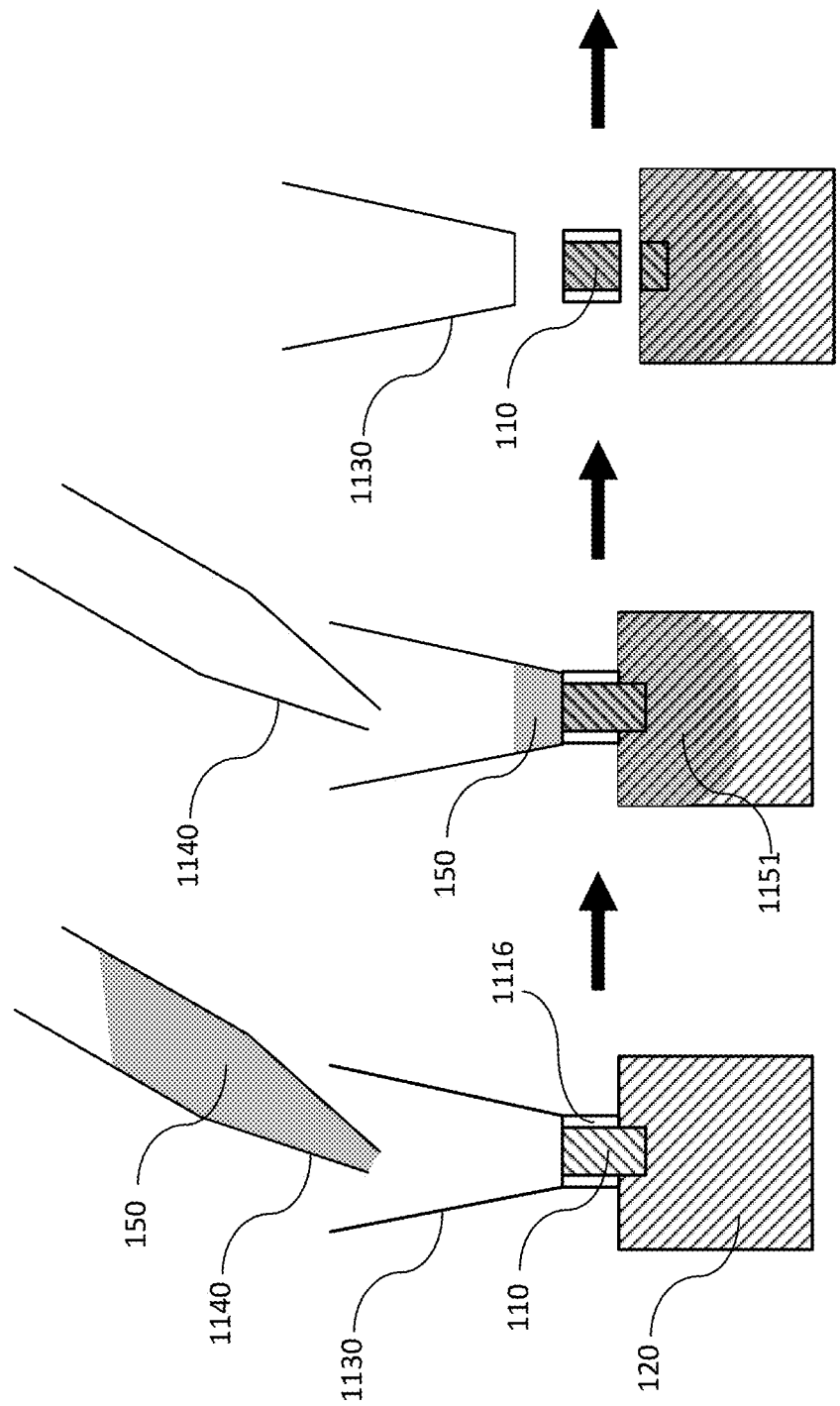

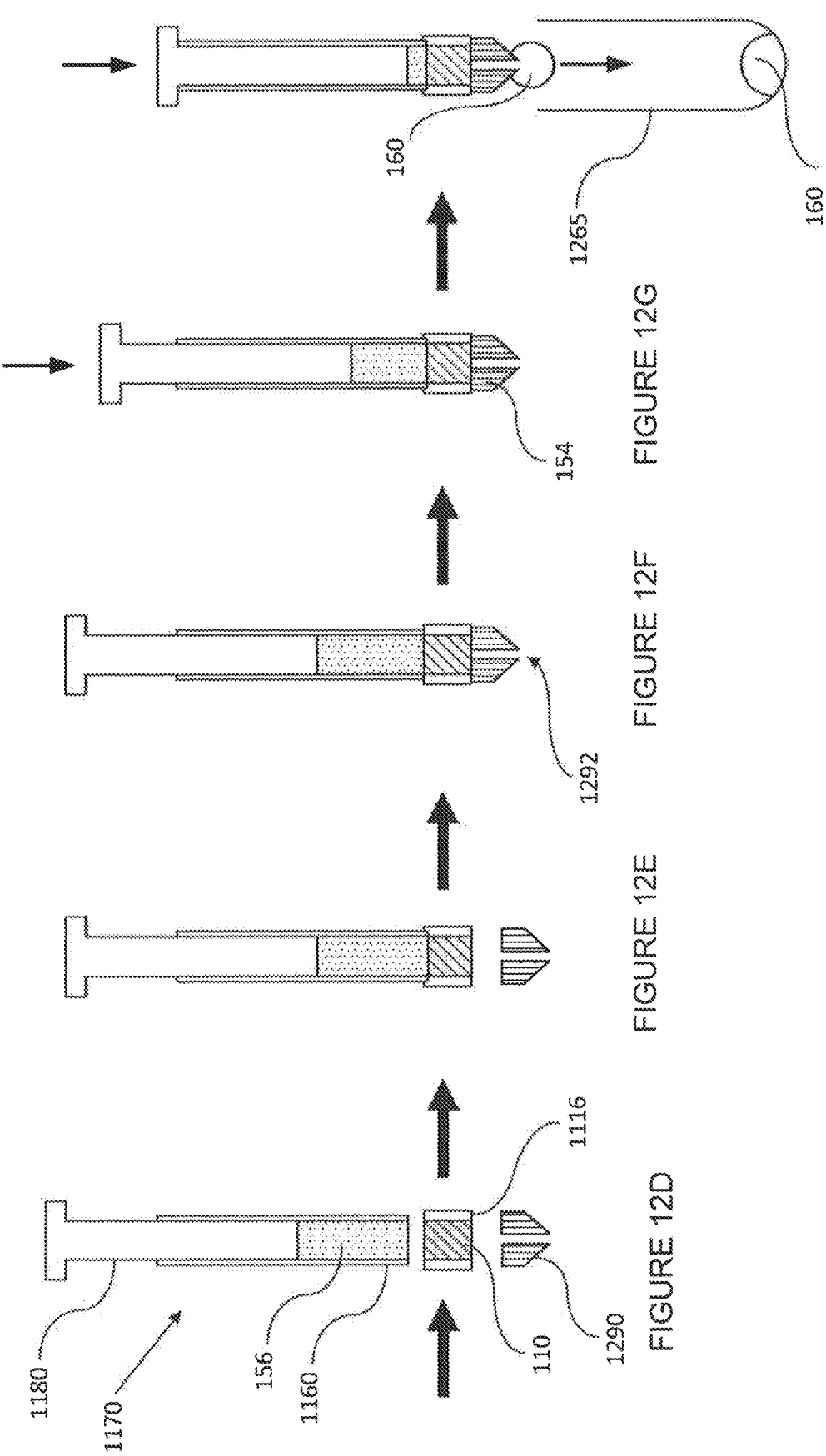

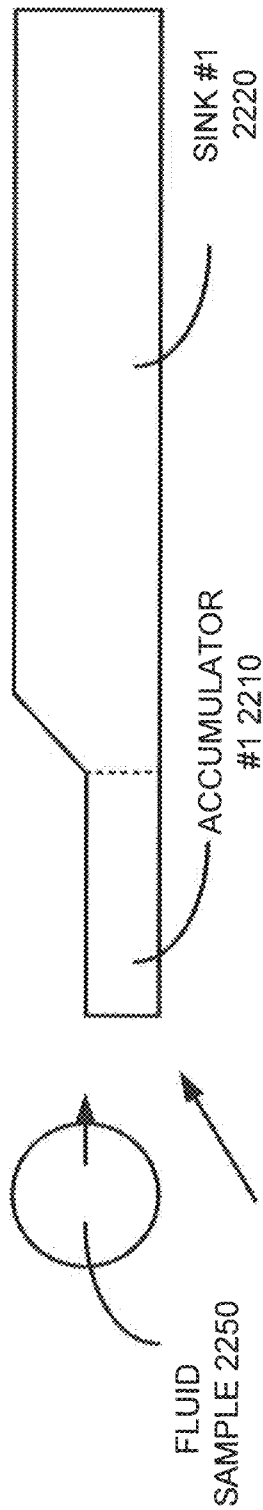
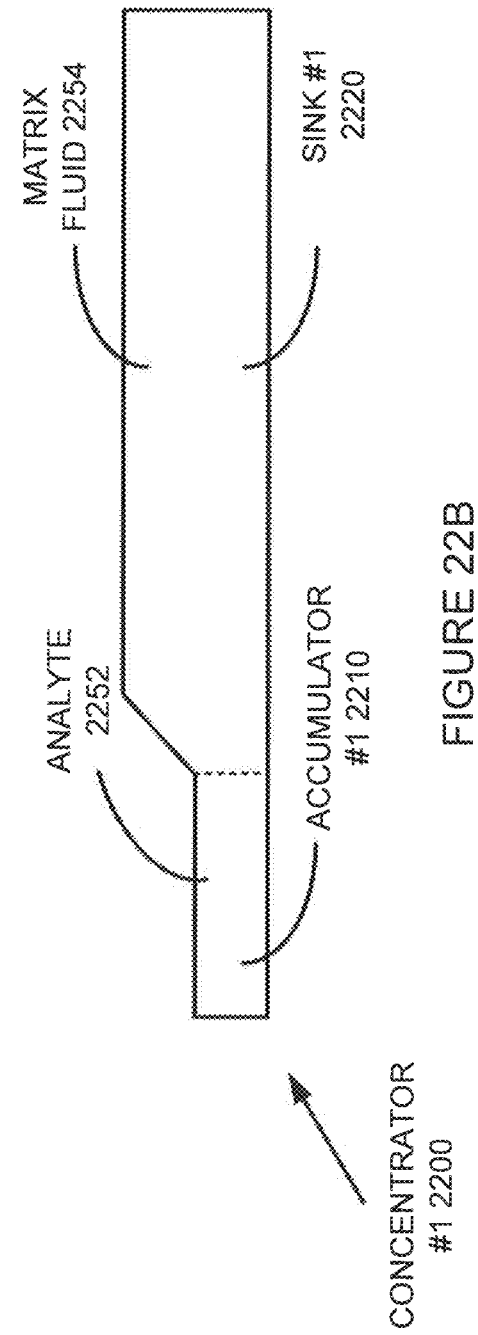
FIGURE 22A
FIGURE 22B

SAMPLE CONCENTRATION DEVICES

CROSS-REFERENCE TO RELATED APPLICATIONS

This application claims priority to U.S. Provisional Application Ser. No. 62/206,749 filed Aug. 18, 2015, the entire contents of which is incorporated herein by reference.

FIELD OF THE TECHNOLOGY

The present disclosure relates to a concentrator for concentrating, purifying or otherwise isolating one or more target analytes in a fluid matrix, and related methods, using self-wicking materials, such as monoliths. The present disclosure can be used as a point-of need sample preparation device. The self-contained device can be used for the extraction and concentration of specific target molecules, such as nucleic acids.

BACKGROUND

Extraction of important target analyte(s) form a sample matrix for concentrating, purifying or otherwise isolating the target analyte can be challenging. The type of target analyte, the amount or concentration of the target analyte in the sample matrix, the sample matrix components, and the desired purity or concentration of the extracted analyte are all variables that can affect the extraction of a target analyte. The extraction of nucleic acids, for example, from biological samples for the purpose of diagnostic procedures is an increasingly important capability for medical science. The science of whole-genome sequencing is emerging as a powerful diagnostic technology that is becoming accessible in first world countries for routine medical services.

While the technology for sequencing DNA has advanced tremendously, obtaining DNA from a biological sample remains a challenge. Common processes to obtain DNA still involve invasive, labor intensive and time consuming techniques using specialized equipment. For example, genomic DNA extraction necessarily begins with the lysis of cells that contain the DNA to be analyzed. After lysis, only two commonly used DNA isolation procedures exist. One is phenol-chloroform extraction followed by DNA precipitation. This process is time consuming, requires multiple manipulations of the sample, requires refrigeration, centrifugation and evaporation, and finally, generates toxic waste. The other involves DNA adsorption on a silica matrix. This process is also labor intensive, time consuming, requires the use of chaotropic salts that must be disposed of as hazardous waste, and finally, also requires specialized equipment. DNA extraction methods that are simpler, generate less waste and require less equipment will further increase the availability of genetic analysis methods.

Currently, blood samples are the most reliable source for nucleic acids to be used in whole-genome sequencing or other forms of genetic testing such as Sanger Sequencing, SNP Arrays, RFLP analysis, and forensic methods. Other DNA sources, such as saliva and buccal swabs, are less invasive to collect than blood but are much more variable in matrix composition and DNA content. All of these samples tend to yield dilute DNA or DNA extracts contaminated with inhibitors that interfere with downstream processing, e.g., enzymological reactions. Nevertheless, the ease of collection makes these samples an attractive DNA source.

As sequencing technology advances, the amount of DNA required for successful sequencing continues to decrease. The demand for simple at-home sample collection also continues to increase. The ability to extract adequate amounts of DNA from typical buccal or saliva samples as well as a method of increasing the concentration of DNA in low-yield buccal samples can increase the success rate of DNA sequence analyses.

Self-wicking materials can include a number of different materials, including monoliths, absorbent pads, etc. Macroporous monolithic materials are used in the field of separations science, most commonly as chromatographic media. The two most common base materials for monoliths are silica gel and acrylic polymers. Both can be made with the mechanical strength necessary to withstand the extreme pressure of HPLC or the mechanical stresses of industrial-scale purification processes. Polymeric monoliths are also frequently used in solid-phase extraction consumables and in microfluidic devices. For example, polymeric monoliths are popular components in microfluidic chips because they can be cured-in-place with masked UV irradiation to generate integrated microscale chromatography columns.

U.S. Patent Publication No. 2014/0127669 describes the use of polymeric monoliths in the field of sample preservation as an alternative to paper-based dry blood-spot (DBS) DNA preservation matrices. Blood spots spiked with small molecule pharmaceuticals dried on a monolith film were treated to recover the pharmaceuticals.

The concentrator and related methods of the present disclosure, using self-wicking monoliths, can provide a simple, stand-alone target analyte isolation and concentration system that minimizes the need for hazardous chemicals and specialized equipment. For example, the concentrator of the present disclosure can provide the ability to extract adequate amounts of biological targets, e.g., nucleic acid, from typical clinical samples and increase the concentration of nucleic acid in these samples to increase the efficiency of various testing methods, e.g., DNA sequencing. The concentrator of the present disclosure can also reduce the chemicals and equipment needed to obtain a concentrated target analyte, e.g., DNA sample.

SUMMARY

The present disclosure relates to a concentrator for concentrating, purifying or otherwise isolating one or more target analytes in a fluid matrix, and related methods, using self-wicking materials, such as monoliths. The present disclosure can be used as a point-of need sample preparation device. The self-contained device can be used for the extraction and concentration of specific target molecules, such as nucleic acids.

The present disclosure describes a self-contained, simple-to-use, and optionally disposable device that can be constructed for target analyte, e.g., nucleic acid, extraction from a sample matrix (e.g., biological sample, such as lysed cells) with a self-wicking material, such as macroporous monolithic polymers, as the central fluidic components. The device can be used for both the extraction and the concentration of dilute target analytes, e.g., DNA extracts.

In one embodiment, the present disclosure relates to a method for concentrating an analyte in a fluid matrix, the method including providing an accumulator comprising a first self-wicking porous polymer monolith, the accumulator having at plurality of interface surfaces, and a fluid capacity volume (Vac), and wicking the fluid matrix containing the analyte into the accumulator through any interface surface of the accumulator; and capturing the analyte in the accumulator. The method can further include providing a sink comprising a second self-wicking porous polymer monolith, the sink having an interface surface, and a fluid capacity volume (Vfs), and coupling any interface surface of the accumulator to the interface surface of the sink, wherein the interface surface of the accumulator and the interface surface of the sink are in fluid communication and configured to facilitate wicking of fluid across the coupling.

The method can further include uncoupling the accumulator from the sink, providing an elution fluid source, coupling the elution fluid source to any selected interface surface of the accumulator wherein the elution fluid source and the interface surface of the accumulator are in fluid communication, introducing an elution fluid having a volume Vef from the elution fluid source into the accumulator through the selected interface surface of the accumulator, wherein Vef is greater than Vac, and wherein the elution fluid releases the analyte from the accumulator, and collecting the analyte from any other interface surface of the accumulator. In some embodiments, the method can utilize a matrix absorber. The elution fluid can be introduced in portions wherein each portion can generate a corresponding volume of eluate, referred to as fractions by those skilled in the art of chromatography, where at least one of the portions contains the released and eluted analyte.

In one embodiment, the present disclosure relates to a concentrator for concentrating an analyte in a fluid matrix, the concentrator including an accumulator comprising a first self-wicking porous polymer monolith, the accumulator having a plurality of interface surfaces, and a fluid capacity volume (Vac), wherein the accumulator has an affinity for the analyte.

The concentrator can further comprise a sink, wherein the sink includes a second self-wicking porous polymer monolith, the sink having at least one interface surface, and a fluid capacity volume (Vfs), wherein the at least one interface surface of the sink and any interface surface of the accumulator are coupled together in fluid communication and configured to facilitate wicking of fluid across the coupling. The accumulator, sink or both can be contained in a sleeve or housing. The sleeve or housing can form a water-tight seal with the accumulator, sink or both. For example, the sleeve or housing can be coupled with an elution syringe wherein the junction between the monolith(s) and the syringe is water tight.

The concentrator can further include an elution fluid dispenser, the elution fluid dispenser having an elution fluid reservoir, and an elution fluid pressurizer wherein the elution fluid dispenser is configured to attach to the interface port of the housing and to establish fluid communication between the elution fluid reservoir and the at least one interface surface of the accumulator.

The concentrator can further include a cutter which can be configured to separate the accumulator and the sink such that the accumulator and sink are no longer in fluid communication.

In another embodiment, the present disclosure relates to a method for concentrating an analyte in a fluid matrix, the method includes providing a first concentrator having a first self-wicking porous polymer monolith, the monolith includes a first accumulator, the first accumulator having a plurality of interface surfaces, and a fluid capacity volume (Vac1), providing a first sink having a second self-wicking porous polymer monolith, the sink having an interface surface, and a fluid capacity volume (Vfs1); coupling any interface surface of the first accumulator to the interface surface of the first sink, wherein at least one interface surface of the first accumulator and the interface surface of the first sink are in fluid communication and configured to facilitate wicking of fluid across the coupling, wicking the fluid matrix containing the analyte into the first accumulator through any interface surface of the first accumulator, and capturing the analyte in the first accumulator. The method can further include wicking the fluid matrix in excess of the Vac from the first accumulator into the first sink, and retaining the excess fluid matrix in the first sink. The method can further include wicking a wash fluid having a volume Vw1 into the first accumulator through any interface surface of the first accumulator, wherein Vw1 is greater than Vac1.

A second concentrator can also be used. The method can further include uncoupling the first accumulator from the first sink, providing a second concentrator including a third self-wicking porous polymer monolith, the monolith having an second accumulator and a second sink, the second accumulator having at plurality of interface surfaces, and a fluid capacity volume (Vac2), the second sink having a fourth self-wicking porous polymer monolith, the second sink having an interface surface, and a fluid capacity volume (Vfs2), and coupling any interface surface of the first accumulator to any interface surface of the second accumulator, wherein the interface surface of the first accumulator and the interface surface of the second accumulator are in fluid communication.

A first elution fluid can be provided by coupling a first elution fluid source to any selected interface surface of the first accumulator, introducing a first elution fluid having a volume Vef1 from the first elution fluid source through the selected interface surface of the first accumulator through the second accumulator and into the second sink, wherein Vef1 is greater than Vac1+Vac2, and wherein the first elution fluid releases the analyte from the first accumulator, and capturing the analyte in the second accumulator. The method can further include uncoupling the first accumulator from the second accumulator, uncoupling the second accumulator from the second sink, providing a source of a second elution fluid, coupling the second elution fluid source to any selected interface surface of the second accumulator, introducing a second elution fluid having a volume Vef2 from the second elution fluid source into the second accumulator through the selected interface surface of the second accumulator, wherein Vef2 is greater than Vac2, and wherein the second elution fluid releases the analyte from the second accumulator; and collecting the analyte from any other interface surface of the second accumulator. The method can also include a matrix absorber having an interface surface, a bypass channel with an outlet, and a fluid capacity volume (Vma), wherein Vma is smaller than or equal to Vac2; coupling the interface surface of the matrix absorber to any selected interface surface of the second accumulator, wherein the interface surface of the matrix absorber and the selected interface surface of the second accumulator are in fluid communication, providing a source of a second elution fluid, coupling the second elution fluid source to any other interface surface of the second accumulator, introducing a second elution fluid having a volume Vef2 from the second elution fluid source into the second accumulator through the any other interface surface of the second accumulator, wherein Vef2 is greater than Vac2, and wherein the second elution fluid releases the analyte from the second accumulator, and collecting the analyte from the bypass channel outlet of the matrix absorber.

In another embodiment, the present disclosure relates to a system for concentrating an analyte in a fluid matrix including a first accumulator having a first self-wicking porous polymer monolith, the accumulator having a plurality of interface surfaces, and a fluid capacity volume (Vac1), a first sink having a second self-wicking porous polymer monolith, the sink having an interface surface, and a fluid capacity volume (Vfs1), a second accumulator having a third self-wicking porous polymer monolith, the second accumulator having a plurality of interface surfaces, and a fluid capacity volume (Vac2), a second sink having a fourth self-wicking porous polymer monolith, the second sink having an interface surface, and a fluid capacity volume (Vfs2), wherein at least one interface surface of the first accumulator and the interface surface of the first sink, at least one interface surface of the second accumulator and the interface surface of the second sink, and at least one interface surface of the first accumulator and at least one interface surface of the second accumulator are configured to form a coupling, and wherein the first and second accumulators have an affinity for the analyte. The system can also include a first elution fluid configured to release the analyte from the first accumulator, a second elution fluid configured to release the analyte from the second accumulator, or both. The system can also include a matrix absorber having a fifth self-wicking porous polymer monolith, the matrix absorber having an interface surface, a bypass channel, and a fluid capacity volume (Vma), wherein Vma is smaller than or equal to Vac2, wherein the interface surface of the matrix absorber is configured for fluid communication with any interface surface of the accumulator of the second concentrator.

BRIEF DESCRIPTION OF THE DRAWINGS

The foregoing and other features and advantages provided by the present disclosure will be more fully understood from the following description of exemplary embodiments when read together with the accompanying drawings, in which:

FIGS. 1A-1C show a block diagram of an embodiment of a system configured to concentrate a target analyte from a fluid sample.

FIGS. 3A-3D show a block diagram of an embodiment of a system configured to concentrate analyte from a fluid sample.

FIGS. 7A-7E show a block diagram of an embodiment of a system configured to concentrate a target analyte from a fluid sample.

FIGS. 9A-9D show a block diagram of an embodiment of a system configured to concentrate a target analyte from a fluid sample.

FIGS. 11A-11H show an exemplary step by step method for the operation of an embodiment of an analyte concentrator.

FIGS. 12A-12H show another exemplary step by step method for the operation of an embodiment of an analyte concentrator.

FIGS. 22A-22D show an exemplary embodiment of an analyte in a fluid sample being concentrated in one concentrator (2200) and thereafter being further concentrated on a second concentrator (2230).

DETAILED DESCRIPTION

Figure 2:
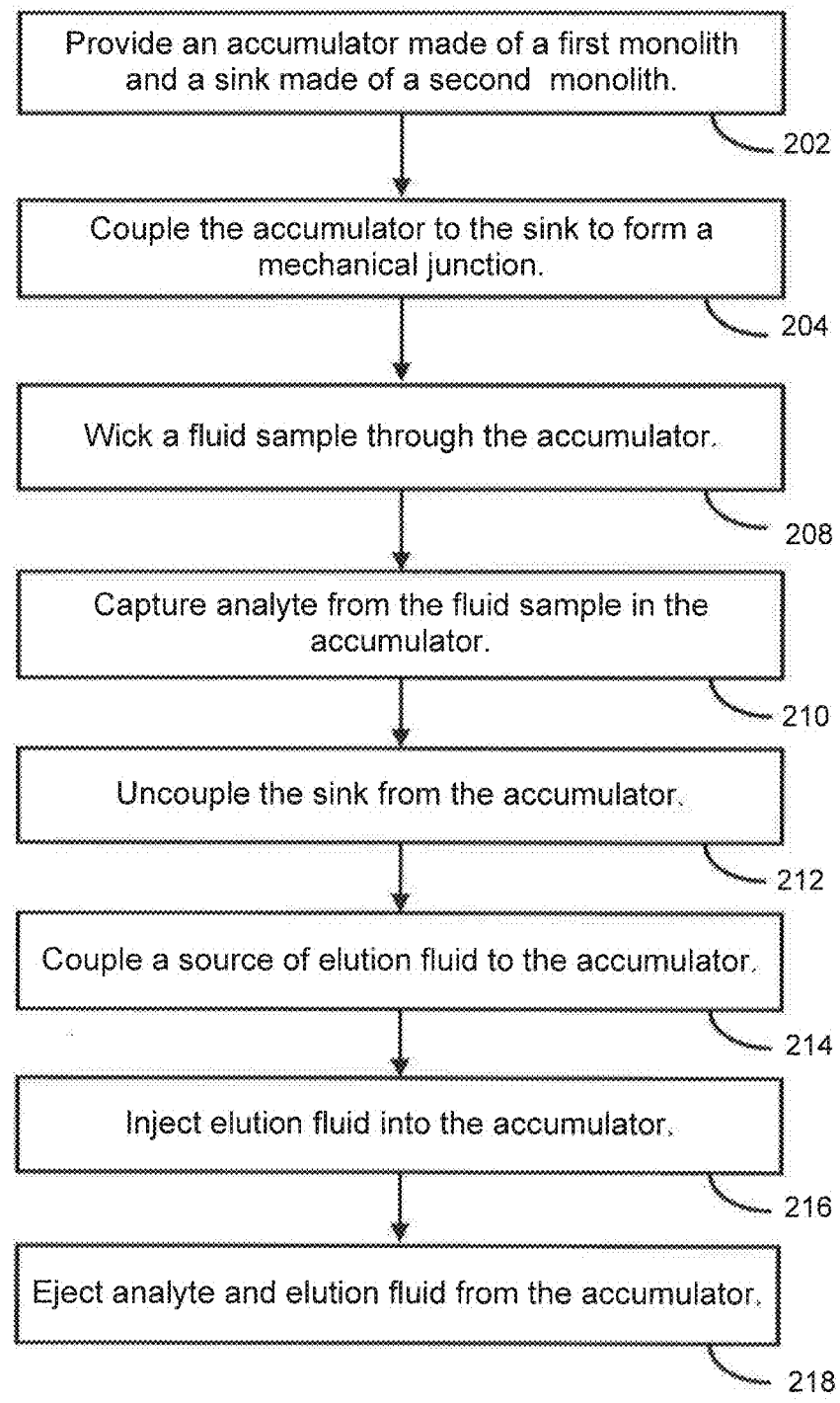
FIG. 2 shows a flowchart for an exemplary method of concentrating a target analyte in a system shown in FIGS. 1A-1C.

The present disclosure relates to a concentrator for concentrating one or more analytes in a fluid matrix, and related methods, using one or more self-wicking materials, such as monoliths. The composition, whether described as a device, system, apparatus, concentrator, etc., can be used to extract, concentrate, purify, isolate or combinations thereof, whether described as only performing one of these functions.

In one embodiment, the present disclosure relates to a method for concentrating an analyte in a fluid matrix, the method including providing an accumulator comprising a first self-wicking porous polymer monolith, the accumulator having a plurality of interface surfaces, and a fluid capacity volume (Vac); wicking the fluid matrix containing the analyte into the accumulator through any interface surface of the accumulator; and capturing the analyte in the accumulator.

Different target analytes that can be concentrated by the methods and compositions of the present disclosure including DNA, RNA, PNA, proteins, metabolites, pharmaceuticals, toxins, viruses, bacteria, spores, eukaryotic cells, amoeba, plankton, pollutants, heavy metals, environmental contaminants, pathogens, food additives, colorants, and polymers. The methods and compositions of the present disclosure are applicable to the diagnostics industry, genetic analysis industry, pharmaceutical industry, law enforcement, environmental monitoring, hospitals, clinics, food manufacturing, and quality control organizations. For example, DNA, RNA and related small molecules, such as toxins or pharmaceuticals, can be concentrated from forensic samples. For example, antibodies specific to a wide variety of target analytes can be coupled to monolith and capture the antibody specific targets for epidemiological research. For example, accumulator elements can be fabricated from molecularly imprinted monolith. These examples illustrate that monolith can be made having all the affinities that other chromatographic media can have.

The terms analyte and target analyte can describe molecules of interest contained within a sample. The terms may refer to the chemical species of interest in a sample that is desired for use or analysis. Generally, it is desirable to purify the target analyte from other components in a sample and to obtain the analyte in a sufficiently high concentration for subsequent processes such as characterization, identification or sequencing to be performed.

In some embodiments, the target analyte can be a biological molecule, including a nucleic acid. For example, the target analyte can include DNA.

The fluid matrix, or sample that contains the target analyte can be a biological sample, including blood, saliva, urine, stool, colostrum, milk, sputum, cerebrospinal fluid, amniotic fluid, plasma, semen, vaginal secretion, or serum. The biological fluid can be artificially cultured, for example, it can be a recombinant enzyme, a virus, fermentation medium, a vaccine, or similar. The biological fluid can also be associated with a plant, such as a plant exudate or an extract of a plant. In addition, a sample may be a fluid derived by the treatment or extraction of a portion of water, biological material, soil, a swab, blood, a suspension or a solution with a 'conditioning solution' or a process capable of extracting target analyte or capable of making the target analyte capable of being extracted from the sample by adsorption to the accumulator.

The fluid matrix can refer to all other materials in a sample that are not the target analyte. The fluid matrix can contain particulates or solids that can be removed by filtration or it may be an extract, containing non-analyte and potentially analyte also, of a solid sample. Spent fluid matrix can refer to the components of the fluid matrix that remain after the analyte has been captured by an accumulator element.

The fluid sample can also be obtained from swabbing or otherwise extracting material from surfaces, such as medical equipment, personal protective equipment, furniture, counters, or floors.

The fluid sample can also be water samples, cosmetics, extracts from soil, foods, pharmaceuticals or raw materials. The fluid sample can be an environmental sample, for example, it may be a water sample or an extract of a solid of interest, for example, a soil extract, an ash extract, or similar. A water sample can include samples taken at various stages in water purification processing, for example, the water sample may be raw sewage or processed sewage.

The fluid sample can be a sample of interest for molecular diagnostics or analytics. In addition to concentrating the target analyte(s), the processing of the fluid sample can include a detection/analysis step to determine the presence or absence of the target analyte(s).

In some embodiments, the sample can be a solid sample, e.g., a dried or lyophilized sample. The solid sample can be reconstituted in a liquid, e.g., an aqueous diluent. The aqueous diluent can be a salt, a buffer, a surfactant solution, an enzyme solution, an acidic solution or a basic solution.

The fluid sample containing target analyte, or sample, can be purified or partially purified using an industry standard purification process. The sample can be contain, or can be purified or partially purified to contain, about or less that about 500000, 100000, 50000, 10000, 5000, 1000, 500, 100, 50, 10, 5, 1, 0.5, 0.1, 0.05, 0.01, 0.005 or 0.001 ppm of non-DNA components.

Depending on the capacity of the system, the accumulator monolith, etc., the volume amount of the fluid matrix, or the amount of the fluid matrix tested, can be about, more than about, or less than about 0.1, 0.5, 1, 2, 3, 4, 5, 6, 7, 8, 9, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5500, 6000, 6500, 7000, 7500, 8000, 8500, 9000, 9500 or about 10000 µL. These vales can also define a range, such as about 400 to about 600 µL. The amount of fluid matrix to be tested can include any dilution of the sample or fluid matrix before testing, such as with a loading buffer.

The concentration of the target analyte in the fluid matrix, or fluid matrix to be tested, can be about, or greater than about, or less than about 0.00001, 0.00005, 0.0001, 0.0005, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90 or about 100 ng/µL. These vales can also define a range, such as about 0.001 to about 0.1 ng/µL.

In another embodiment, the concentration of the target analyte in the fluid matrix, or fluid matrix to be tested, can be about, or greater than about, or less than about 0.00001, 0.00005, 0.0001, 0.0005, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 or about 10 mM. These vales can also define a range, such as about 0.01 to about 1 mM.

The pH of the fluid matrix, or the pH of the fluid matrix tested, can affect performance. The pH of the fluid matrix, or the pH of the fluid matrix tested, can be about, more than about, or less than about 1, 2, 3, 4, 4.5, 5, 5.5, 6, 6.5, 7, 7.5, 8, 8.5, 9, 9.5, 10, 11 or about 12. These values can define a range, such as about a pH of about 2 to about 8, or about 5.5 to about 7.5. Similarly, the ionic strength of the sample, or combined sample in the loading solution, can vary depending on the analysis, the analyte, the monolith, etc. The ionic strength of the fluid matrix, or the combined sample, can affect performance. The ionic strength of the fluid matrix, or the fluid matrix tested, can be about, more than about, or less than about 0.1, 0.5, 1, 5, 10, 20, 30, 40, 50, 60, 70, 80, 90, 100, 200, 300, 500, 750, 1000, 1500, 2000, 2500, 3000, 3500, 4000, 4500, 5000, 5500, 6000, 6500, 7000, 7500, 8000, 8500, 9000, 9500 or about 10000 mM. These values can define a range, such as about 5 to about 30 mM, or about 150 to about 500 mM, or about 2000 to about 4000 mM.

The concentration of the target analyte in the fluid matrix, or the fluid matrix tested, can be increased using the methods and compositions of the present disclosure. The amount or degree of the concentration can be about, more than about, or less than about 2×, 3×, 4×, 5×, 6×, 7×, 8×, 9×, 10×, 20×, 30×, 40×, 50×, 60×, 70×, 80×, 90×, 100×, 500× or about 1000×. These values can be used to define a range, such as about 5× to about 50×.

In some embodiments, the elution volume from the system can be fixed. The degree of sample concentration can, therefore, be inversely proportional to the volume of sample loaded. For example, a 500 µL sample volume reduced to 50 µL provides a 10× level of concentration. Pre-dilution of the sample can reduce the net level of concentration. For some samples, pre-dilution is not necessary. For example, pre-dilution is optional for samples, such as environmental water samples, urine, or beverages. Other sample can be pre-diluted, such as saliva, stool, or body lotion.

The recovery of the target analyte from the system can be 100%, or less. A full recovery, or a recovery greater than about 95, 90, 85, 80, 75, 70, 65, 60, 55, 50, 45, 40, 35, 30, 25, 20, 15 or about 10%, of the target analyte can be obtained. In some embodiments, the recovery can be affected by the concentration of the analyte. A full recovery, or a recovery greater than about 95, 90, 85, 80, 75, 70, 65, 60, 55, 50, 45, 40, 35, 30, 25, 20, 15 or about 10%, can be obtained from a sample having a concentration of about, or greater than about, or less than about 0.00001, 0.00005, 0.0001, 0.0005, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90 or about 100 ng/µL. These values can be used to define a range, such as a recovery of about 50% or greater for analytes concentrations between 0.005 and 0.5 ng/µL. For example, a recovery of DNA from a biological sample matrix can be greater than about 90% for concentrations greater than about 1 ng/µL.

An accumulator is provided and can be used to filter out, retain or capture the target analyte from the fluid matrix or sample. The accumulator can be a self-wicking material, such as a self-wicking monolith, or "accumulator" or "accumulator material" or "accumulator monolith." The self-wicking material can be any material that has sufficient self-wicking properties, can be designed or modified to have an affinity for one or more analytes, can be formed into different geometries, or combinations thereof. For example, the self-wicking material can be a self-wicking monolith as described in U.S. patent application Ser. No. 14/549,055, the disclosure of which is incorporated by reference in its entirety. The accumulator can contain a self-wicking monolith that can be designed or modified to have an affinity for one or more target analytes.

As described herein, each accumulator, sink, and matrix absorber can be formed from a self-wicking material. One embodiment of the self-wicking material is a monolith which is used herein and in the examples as an exemplary self-wicking material. Other non-monolith accumulators, sinks and matrix absorber, can be used with the methods and compositions of the present disclosure. The self-wicking material can be any material that can provide self-wicking action, such as having a wick rate of about 1 cm or more, can be configured to form a coupling in fluid communication with at least one other material, and has a fluid capacity. Examples of self-wicking materials include absorbent pads, such as those used for lateral flow tests, cellulose fiber, such as woven and non-woven sheets, high-density cellulose which can be provided in a number of different thicknesses and densities, micro-patterned plastics, molecular sieve, superabsorbent materials, such as starch-acrylonitrile copolymer, sodium polyacrylate, polyacrylamide, CM-cellulose and PVA copolymers.

In one embodiment, the accumulator in a concentrator is a volume of chromatographic stationary phase made from a self-wicking macroporous monolith. The interior pore surfaces of the accumulator can include hydrophilic groups that cause wicking and one or more types of functional side-chains that can adsorb one or more target analytes from a sample as the sample flows through the accumulator. The functional molecules can be incorporated into the accumulator pore structure as monomers during polymerization, or they can be grafted onto the pore surfaces after the monolith has been formed using various chemical processes well known to those skilled in the art. Some example functional groups include primary amines, secondary amines, tertiary amines, sulfates, phosphates, acetates, benzene, phenol, benzoate, alkyl, amino alkyl, lectins, antibodies, apoproteins, avidins, polynucleotides, amphiphiles, chelators, toxins, pharmaceuticals, sugars, chiral molecules or cyano groups. The accumulator may have any shape that can be cured in a mold including disk, rod, truncated cone, star, or complex geometry. The accumulator can have multiple internal zones, each containing a different functional chemistry. The accumulator can be any size and can have multiple surfaces capable of interfacing with other components in a concentrator device.

The accumulator monolith can wick the fluid, e.g., the fluid matrix containing the analyte, wash fluid, elution fluid, etc., that is in fluid communication with any of its interface surfaces. As used herein, the term "self-wicking" refers to the effect of capillary action by the monolith pores on a liquid. This is the property of the monoliths that causes a liquid sample to flow spontaneously from a first portion of the monolith to another portion spaced from the first without the need for an external pressure differential to be applied (as is used, for example, in conventional column chromatography). It is this self-wicking ability that can alone provide motility to the fluids applied during the target analyte concentration and optional washing.

Self-wicking can be independent of the orientation of the monolith in space. It can occur vertically, for example up the monolith, or laterally, that is, along the monolith, depending on the method of application of the fluid.

In some embodiments, self-wicking refers to a material exhibiting a wicking measurement of at least about, more than about, or less than about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.2, 10, 11, 12, 13, 14, 15, or about 20 cm in the following wicking test. These values can be used to define a range, such as about 1.5 to about 3 cm. The different monoliths described here, or portions thereof, can have different wicking rates. The portions having different rates can be useful as flow restrictors, for example, to retain a fluid in a preceding portion of the self-wicking monolith.

Fluid flow through the monolith can occur without the need for externally applied pressure. Accordingly, self-wicking monoliths as described herein can be used in methods wherein the fluid flows with no externally applied pressure gradient across the monolith. A favorable interfacial energy between the fluid and the monolith material can cause the wicking action by pulling fluid into the material until all of the monolith has been wetted. The free energy of this interaction can create a hydrostatic pressure at the fluid front below ambient pressure. In other words, the back pressure of the fluid wicking through the monolith can be less than ambient pressure at any elevation, and therefore less than mean sea level pressure. When the monolith is filled with fluid, wicking stops.

The following wicking test measures the distance water travels up a monolith cured with dimensions: 1.27 cm wide, 6.35 cm long, 0.30 cm thickness. Prior to testing, the monolith is stored in atmospheric conditions (temperature: 18-22° C., RH 10-40%). The test involves (i) 3 mm of the monolith is submerged in de-ionized water with the monolith in the upright orientation, (ii) water moves up the length of the monolith due to wicking action, and (iii) the distance traveled by the water over the course of 2.0 min is measured at the corner of the monolith having the greatest measurement. The measurement may be made visually, simply by observing the solvent front. Alternatively, a dye may be added to aid measurement. The dye can be a dye that travels with the water without being significantly retarded by the monolith. Suitable examples include FD&C Yellow number 1 and fluorescein. Red 40 and Blue 1 can be also be used for some monoliths as described herein, although the dyes may interact with particular functionalities in the matrix (for example, free amino groups) of certain monoliths as described herein, thereby causing retardation. Very large dyes, such as blue dextran, may be retarded by the pore size of the monolith. Similarly, charged dyes may move along the monolith at different rates.

Wicking rate can also be measured in units of s/4 cm. A comparison Table equating measurements according to the wicking test as described herein and a wicking value in s/4 cm is provided below.

| Wick Rate (cm) as measured in the wicking test described herein | Conversion to wicking rate in s/4 cm |
|---|---|
| 1.0 | 1920 |
| 2.0 | 480 |
| 3.0 | 213 |
| 4.0 | 120 |
| 5.0 | 77 |
| 6.0 | 53 |

The monolith can be made from any material(s) that can be used to form a self-wicking monolith that can selectively capture a target analyte. In some embodiments, the self-wicking monolith can include a hydrophilic monomer and a linker monomer, such as those described in U.S. patent application Ser. No. 14/549,055, the disclosure of which is incorporated by reference in its entirety. The linker monomer can have two polymerizable groups spaced apart by a linker including at least one —C(R)$_2$O— group. Optionally, one or more further monomers can be included. Each R can be hydrogen, or can be any organic group. The linker can include an alkyl or substituted alkyl chain —(C(R)$_2$)$_n$— in which at least one or two of the —C(R)$_2$— groups can be replaced by oxygen. n can be 3 to 20, for example, 5 to 15, for example, 5 to 13. The R groups can include further polymerizable groups. The linker can be a polyether, for example, a polyethylene glycol or similar. The linker can include a polyethylene glycol chain, for example containing 1, 2, 3, 4, 5 or more —OC(R)$_2$C(R)$_2$— groups, for example, 1, 2, or 3 —OC(R)$_2$C(R)$_2$— groups.

Each of the polymerizable groups of the linker monomer can include a vinylic moiety. For example, each polymerizable group of the linker molecule can be independently selected from acryl or methacryl. In some embodiments, the linker is selected from —O—CH$_2$—CH$_2$—O—; —(—O—CH$_2$—CH$_2$—)$_n$—O—, wherein n is selected from 2, 3, 4, or 5; —O—CH$_2$—CH(OH)—CH$_2$—O—; and —O—CH$_2$—CH(OH)—CH$_2$—CH(OH)—CH$_2$—CH(OH)—CH$_2$—O—. The linker monomer can include further polymerizable groups, for example, the linker may be —OCH$_2$—C(CH$_2$O—)(CH$_2$CH$_3$)—CH$_2$O—, wherein — represents a bond to a further polymerizable group. Suitable linker monomers include ethyleneglycol diacrylate, ethyleneglycol dimethacrylate, tetra(ethylene glycol) dimethacrylate, tetra(ethylene glycol) diacrylate, and di(ethylene glycol) dimethacrylate. Suitable hydrophilic monomers include an acrylate or methacrylate, for example, the hydrophilic monomer can be 2-hydroxyethyl methacrylate (HEMA), 2-hydroxyacrylate, 2-hydroxyethyl acrylate, 2-hydroxypropyl methacrylate or 2-hydroxypropyl acrylate. In some preferred embodiments, it can be 2-hydroxyethyl methacrylate.

Combinations of linker monomers can include ethylene glycol dimethacrylate and tetraethylene glycol dimethacrylate, or ethylene glycol dimethacrylate and tetraethylene glycol diacrylate. For example, a combination of linker monomers can be ethylene glycol dimethacrylate and tetraethylene glycol diacrylate, for example, in a ratio of 4:3 to 1:3, for example in a ratio of 1:1 to 1:3, for example, in a ratio of 2:3 to 7:10. A combination of linker monomers can be ethylene glycol dimethacrylate and tetraethylene glycol dimethacrylate, for example in a ratio of, 5:1 to 1:1, for example, in a ratio of around 3:1.

The ratio of tetraethylene glycol dimethacrylate to hydrophilic monomer, for example, HEMA, can be about 20:1; 18:1; 16:1; 14:1; 12:1, 10:1; 8:1; 6:1; 4:1; 2:1; or about 1:1. These values can be used to define a range, such as about 10:1 to 1:3, or, 5:1 to 2:1. In some embodiments, the ratio of tetraethylene glycol dimethacrylate to hydrophilic monomer, for example, HEMA, can be about 3:1; 2:1; 1.5:1; 1.4:1; 1.3:1; 1.2:1; 1.1:1; 1:1; 0.9:1; 0.8:1; 0.7:1; 0.6:1; 0.5:1; 0.4:1; or about 0.3:1. These values can be used to define a range, such as about 1:1 to 0.7:1. For example, the ratio of tetraethylene glycol diacrylate to hydrophilic monomer, for example, HEMA, can be 5:2 to 1:3, for example, 2:1 to 1:1.

The total linker monomer to total hydrophilic monomer ratio can be from 1:1 to 10:1, from 1:1 to 7:1, or from 1:1 to 5:1, or from 2:1 to 4:1. Suitably, the total linker monomer to total other monomer content (hydrophilic monomer plus further monomer) can from 1:1 to 10:1, or from 1:1 to 7:1, or from 1:1 to 4:1.

The hydrophilic monomer refers to a monomer with a polar side-chain capable of ionization or hydrogen bonding in an aqueous environment. Generally, polymers with high content of hydrophilic monomers are wettable or will absorb water. Examples of hydrophilic side chains include, without limitation, hydroxyl, amino, acetate, guanidate, amide, sulfate, nitrate, or nitrile. The hydrophilic monomer can include a free hydroxyl group. For example, the hydrophilic monomer can be hydroxyacrylate, 2-hydroxyethyl methacrylate (HEMA), 2-hydroxyethyl acrylate, 2-hydroxypropyl methacrylate or 2-hydroxypropyl acrylate; or acrylic acid. In some embodiments, it is 2-hydroxyethyl methacrylate (HEMA).

The linker monomer can also include hydroxyl groups. A linker monomer can be a hydrophilic monomer. For example, it can be 3-(acryloyloxy)-2-hydroxypropyl methacrylate or glycerol 1,3-diglycerolate diacrylate. These linker monomers including a free hydroxyl group can serve as a linker monomer and/or as a hydrophilic monomer in monoliths and methods as described herein.

The linker monomer refers to a polymerizable compound having at least two polymerizable groups spaced apart by a linker comprising at least one —C(R)₂O— group. The two polymerizable groups can include vinylic moieties, and can for example be acryl or methacryl groups. Where the linker is joined to the two groups by —O—, the linker monomer can be an acrylate or a methacrylate, for example, a diacrylate or dimethacrylate.

Each R can be hydrogen, or any organic group. The linker can be an alkyl or substituted alkyl chain —(C(R)₂)ₙ— in which at least one, preferably at least two, —C(R)₂— groups are replaced by oxygen. The R groups may themselves include further polymerizable groups, and may be the same or different. In some embodiments, each R group is H. The linker can be an ethylene glycol, for example, ethylene glycol, diethylene glycol, or polyethylene glycol. Alternatively, the linker can be a glycerol, for example glycerol 1-3-diglycerolate or 3-acryloyloxy-2-hydroxypropylmethacrylate.

A linker monomer can include mixtures of two or more different such monomers. A linker monomer may refer to single linker monomer as described above, or to a combination of two or more such linker monomers. Exemplary linker monomers are provided in the Table below.

TABLE 1

| | |
|---|---|
| Ethylene glycol dimethacrylate (EGDMA) | 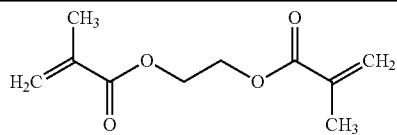 |
| Di(ethylene glycol) dimethacrylate | 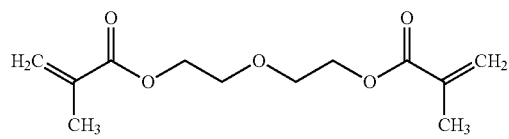 [SMILES: C=C(C)C(=O)OCCOCCOC(=O)C(=C)C] |
| Poly Ethylene glycol dimethacrylate (PEGDMA) | 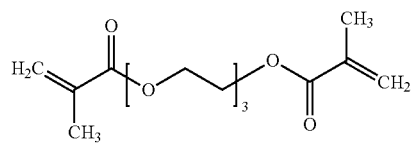 |
| Tetra(ethylene glycol) diacrylate (TEGDA) | 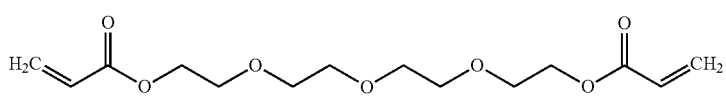 [SMILES: C=CC(=O)OCCOCCOCCOCCOC(=O)C=C] |
| Tetra(ethylene glycol) dimethacrylate (TEGDMA) | 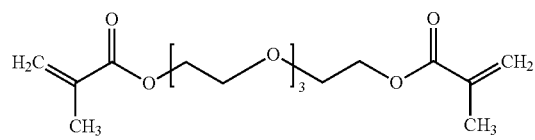 |
| Pentaerythritol triacrylate | 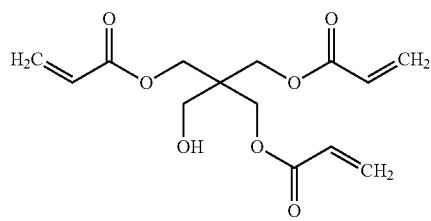 [SMILES: C=CC(=O)OCC(CO)(COC(=O)C=C)COC(=O)C=C] |
| 3-(Acryloyloxy)-2-hydroxypropyl methacrylate | 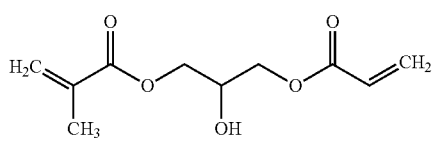 |
| Trimethylolpropane trimethacrylate | 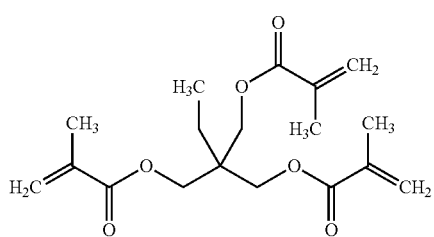 [SMILES: C=C(C)C(=O)OCC(CC)(COC(=O)C(=C)C)COC(=O)C(=C)C] |

TABLE 1-continued

| | |
|---|---|
| Bisphenol A glycerolate dimethacrylate | 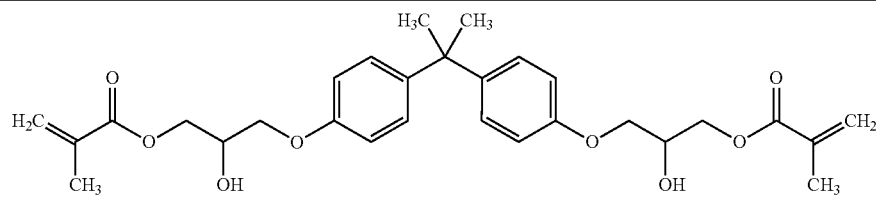 |
| Glycerol 1,3-diglycerolate diacrylate | 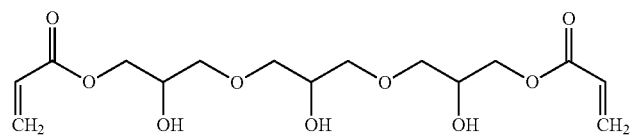 |

The accumulator monolith can have a variable fluid capacity volume. Depending on the capacity of the system, the fluid capacity volume (Vac) of the accumulator monolith can be about, more than about, or less than about 5, 10, 15, 20, 25, 30, 35, 40, 45, 50, 55, 60, 65, 70, 80, 85, 90, 95, 100, 110, 120, 130, 140, 150, 200, 300, 400 or about 500 µL. These values can also define a range, such as about 20 to about 50 µL. The fluid capacity volume of the accumulator can be equal to or less than the sample volume. The fluid capacity of the accumulator can be about 2×, 1.5×, 1×, 0.5×, 0.1×, 0.05×, 0.01×, 0.005× or about 0.001× of the sample volume. These values can be used to define a range, such as about 1× to about 0.1×.

The rate of absorption of the fluid matrix, or the amount of the fluid matrix tested, into the accumulator monolith can vary depending on self-wicking ability of the monolith, the sample composition, etc. The rate of absorption into the accumulator monolith can be about, more than about, or less than about 1, 5, 10, 15, 20, 25, 30, 35, 40, 45, 50, 60, 70, 80, 90, 100, 200, 300, 400, 500, 600, 700, 800, 900 or about 1000 µL/min. These values can define a range, such as about 20 to about 50 µL/min.

The absorption time of the system can be about, more than about, or less than about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 70, 80, 90, 100, 110, 120, 130, 140, 150, 160, 170 or about 180 minutes. These values can define a range, such as about 2 and about 20 minutes.

The accumulator monolith can be designed, produced, functionalized or otherwise modified to capture or retain specific target analytes in the accumulator. The accumulator monolith can have specific surface chemistry that can capture a target analyte from a cell lysate and release it when treated with an elution solution that has different properties than the lysate solution. Some of the different properties being a different pH, ionic strength, or the concentration of a specific solute. For example, the monolith can include DEAE for complexation of metals, or sulfate or phosphate for capture of proteins or positively charged molecules, or alkyl chains, e.g., C18, to capture small molecules, toxins, drugs, pollutants etc. The monoliths can be functionalized with lectins to capture sugars, or, functionalized with proteinase K to digest away proteins from a sample, or functionalized with antibodies to capture bacteria or viruses, or other materials specific to the antibodies.

In one embodiment, the monolith can include amino groups such as aminoethyl methacrylate to capture species with negative charge such as lipid-membrane fragments, DNA, and proteins. Amino groups are chemically reactive; they can be used for permanently immobilizing other chemicals on the interior surfaces of the monolith after initial fabrication. This bonding can be direct, or it can be via added linkers (e.g. carbodiimide). Amino groups can also be used as the anchor for capture chemistry (for example, to immobilize molecules such as antibodies and/or lectins), and for immobilizing proteinases.

Negatively charged groups such as carboxy or sulfate can be used to capture species with positive charge such as proteins. Carboxyl groups are chemically reactive; they can be used for permanently immobilizing other chemicals on the interior surfaces of the monolith after initial fabrication. This bonding can be direct, or it can be via an added linker.

Long chain alkyl groups, for example, incorporated through use of a monomer having such a chain during polymerization (for example, lauryl methacrylate, or aminolauryl methacrylate, or sulfo-lauryl methacrylate), can be used to capture oils and fatty chain molecules, for example, detergents, triglycerides, lecithins, lipid-membrane fragments and lipoproteins.

The capacity of the accumulator can vary depending the size of the accumulator monolith, the surface area, the volume, the affinity for the target analytes, etc. The capacity of the accumulator can be measured in the amount of target analyte captured. The binding capacity of the system for a target analyte can be about, more than about, or less than about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, 50, 60, 70, 80, 90 or about 100 µg. These values can be used to define a range, such as about 1 to about 5 µg.

The capacity of the system for a target analyte can also be defined in terms of analyte mass per monolith mass. The capacity can be about, more than about, or less than about 10, 20, 30, 40, 50, 60, 70, 80, 90, 100, 150, 200, 250, 300, 350, 400, 450, 500, 550 600, 650, 700, 750, 800, 850, 900, 950, 1000, 1100, 1200, 1300, 1400, 1500, 1600, 1700, 1800, 1900 or about 2000 ng/mg. These values can be used to define a range, such as about 100 to about 800 ng/mg. For example, a DNA capture monolith can hold between 100 to about 800 ng of DNA per mg monolith. In another example, a DNA capture monolith can hold about 3500 ng of DNA in a 7 mg (33 µL total volume, 25% solids) accumulator.

The various monoliths of the present disclosure can have a bulk density of about, more than about, or less than about 0.05, 0.1, 0.15, 0.2, 0.25, 0.3, 0.35, 0.4, 0.45, 0.5, 0.55, 0.6, 0.65, 0.7, 0.75 or about 0.8 g/cc. These values can define a range, such as about 0.15 to about 0.50 g/cc, or about 0.20 to about 0.40 g/cc.

The various monoliths of the present disclosure can have a porosity of about, more than about, or less than about 40, 45, 50, 55, 65, 70, 75, 80, 85, 90 or about 95%. These values can define a range, such as about 50 to about 85%, or about 60 to about 80%

The accumulator monolith can be formed into various shapes and can have a plurality of interface surfaces. The shape of the accumulator monolith can help facilitate self-wicking, can allow for coupling to additional system components, monoliths or both. One shape of the accumulator can be a truncated cone with dimensions of, for example, a diameter about, more than about, or less than about 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 6, 7, 8, 9 or about 10 mm at the tip. The base can have an increased diameter by about 1, 2, 3, 4, 5, 6, 7, 8, 9 or about 10 additional mm. The length of the cone can be about 3, 4, 5, 6, 7, 8, 9, 10, 12, 14, 16, 18 or about 20 mm. The values for each dimension can form individual ranges for each dimension, such as about 2 to about 5 mm for tip, about 3 to about 7 for the base and about 3 to about 9 for the length. In one embodiment, the tip is 2 mm, the base is 3 mm and the length is 5 mm. In another embodiment, the tip is 1 mm, the base is 6 mm and the length is 12 mm. The cross-section shape of the cone may be any shape, for example square, triangular, trapezoidal or irregular. The cross section shape of the accumulator element may change over the length of the accumulator. The shape can also be a cylindrical rod of monolith or a combination of a cylindrical rod section and a truncated cone section.

The shape can be any that includes a taper, such as a cone. A taper can improve the formation of a seal between the accumulator monolith and a housing or casing surrounding, covering or attached to a surface of the accumulator monolith. An accumulator monolith can swell and shrink at various stages in the fabrication process. As a result of the size variability, the taper can promote a seal between a sleeve and at least one portion of the accumulator monolith. The formed seal can also reduce or prevent the migration of fluid around the monolith during use.

The taper angle of the accumulator monolith can be about, more than about, or less than about 5, 6, 7, 8, 9, 10, 12, 15, 20, 30, 45 or about 60 degrees. For a range, 8 to about 12 degrees.

The taper angle of the casing, housing or sleeve can be the same as the accumulator, or can differ by less than about 5, 4, 3, 2, 1, 0.5, 0.25, 0.2, 0.15, 0.1, 0.05, 0.02 or less than about 0.01 degrees. In some embodiments, the accumulator and the sleeve (or housing) have at least one section of intimate contact such that a fluidic seal is made.

The method can further include providing a sink including a second self-wicking porous polymer monolith, the sink having an interface surface, and a fluid capacity volume (Vfs); and coupling any interface surface of the accumulator to the interface surface of the sink, wherein the interface surface of the accumulator and the interface surface of the sink are in fluid communication and configured to facilitate wicking of fluid across the coupling.

In one embodiment, the terms fluid connection or fluidic junction can be used to indicate any assembly that allows fluid to move from one element in a concentrator to another element. In the field, it is generally understood that a fluidic connection can withstand the pressure used in the system and can prevent fluid from leaking out of its intended path. Therefore, in some embodiments, fluidic connections can be fully surrounded by a solid enclosure that is non-permeable to the fluids that are used in the system. Further, fluidic connections can form fluid-impervious seals with the elements that they connect. Here, fluidic connections between wicking elements can require that the two elements are held in close enough proximity that fluid contained in a first element can be wicked into the second without breaking the fluid column. Generally, this means that the two elements must be in physical contact with each other. Fluidic connections in a wicking system can be made by bringing wicking elements into physical contact with each other. Fluidic connections in a wicking system can be broken by separating wicking elements that were previously in physical contact.

A sink is provided and can be used to hold or contain excess fluid, e.g., sample matrix fluid, wash fluid, after it has passed through the accumulator monolith. The sink can be a self-wicking monolith, or "sink monolith." The self-wicking monolith can be any monolith that has sufficient self-wicking properties and can be formed into different geometries, or combinations thereof. For example, the monolith can be a monolith as described in U.S. patent application Ser. No. 14/549,055, the disclosure of which is incorporated by reference in its entirety.

In one embodiment, the sink can be a volume of absorbent material made from self-wicking macroporous monolith or other suitable material with a high wick rate. The sink can be any size and can have multiple interface surfaces capable of forming fluidic connections with other components in a concentrator device. Functionally, one or more sink elements in a concentrator can provide the motive force for drawing samples through concentrator elements. After absorbing spent fluid matrix, sink elements can serve to sequester and hold the fluid matrix within them.

The sink monolith can be coupled to the accumulator monolith. The coupling can establish fluid communication between the sink and accumulator, such that fluid can be wicked from one monolith to the other. The sink can "pull" fluid through the accumulator monolith by wicking. The wicking action of the accumulator, the sink or the combination of both can eliminate the need for an external force or pressure to move fluid, e.g., sample matrix fluid, through the accumulator.

The sink monolith can wick the fluid, e.g., fluid from the accumulator monolith, that is in fluid communication with one or more of its interface surfaces. The sink monolith can have a self-wicking rate that is the same as, greater than, or less than the accumulator monolith. The self-wicking rate of the sink can be about 50%, 100%, 200%, 300%, 400% or about 500% of the wicking rate of the accumulator monolith. In some embodiments, the wick rate of the sink is higher than the accumulator to counteract the effect that any decrease in fluid transport through the accumulator would have on the time required to fully absorb a sample or wash solution.

The sink monolith can have a variable fluid capacity volume. Depending on the capacity of the system, the fluid capacity volume (Vfs) of the sink monolith can be about, more than about, or less than about 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45 or about 50 mL. These vales can also define a range, such as about 1 to about 10 mL. The sink monolith fluid capacity volume can be equal to greater that the sample volume, the accumulator monolith or both. The sink fluid capacity volume can be about 2×, 3×, 4×, 5×, 6×, 7×, 8×, 9×, 10×, 20×, 30×, 40×, or about 50× of the sample volume, the accumulator monolith or both. These values can be used to define a range, such as about 2× to about 20×. In one example, the sink monolith can draw into and maintain lysate and wash fluids in volumes much greater than those applied to the accumulator monolith.

The sink monolith can be formed into various shapes and can have a plurality of interface surfaces. At least one of the interface surfaces of the sink monolith is configured to couple to an interface surface of the accumulator monolith. The coupling of the two interface surfaces can facilitate wicking of fluid across the coupling.

The coupling of two monoliths, such as the accumulator and the sink, can be achieved by placing two pieces of wicking monolith into physical contact with each other. The amount of fluid that can move through such an interface can be roughly proportional to the area of the interface in physical contact. The area of the interface can be about, more than about, or less than about 1, 2, 3, 4, 5, 6, 7, 8, 9, 10, 11, 12, 13, 14, 15 or about 20% of the surface area of the accumulator monolith. These values can be used to define a range, such as about 5 to 10%. In some embodiments, the sink is larger than the accumulator so the relative percent area of the sink interface can be smaller than the relative percent rea of the accumulator interface.

The coupling of two monoliths, such as the accumulator and the sink, can include compressing the monoliths together. The compression of the accumulator and sink together can form a mechanical junction. The amount of compressive force can be small, such as the equivalent of a few pounds of force. In one embodiment, the weight of one 10 mg monolith placed on top of another monolith is sufficient compression. In other embodiments, slightly more pressure is required. The surfaces of the monoliths forming the coupling can also be smooth. The surface variations across an interface of a monolith can be less than about 5 mm, 4, 3, 2, 1, 0.8, 0.6, 0.5 or 0.3 mm. These values can be used to define a range, such as about 1 to about 0.5 mm. In some embodiments, the mechanical junction between any interface surface of the accumulator and the interface surface of the sink can be formed by interlocking surface geometries of the accumulator and the sink. See, e.g., FIG. 15.

The method and compositions of the present disclosure can further include wicking the fluid matrix in excess of the Vac from the accumulator into the sink, and retaining the excess fluid matrix in the sink. For example, a sample volume of about 500 µL can be wicked into an accumulator with a 30 µL fluid capacity. The 470 µL of excess fluid matrix is wicked into the sink. The sink can have a fluid capacity of about, greater than about, or less than about 0.1, 0.2, 0.3, 0.4, 0.5, 0.6, 0.7, 0.8, 0.9, 1, 2, 3, 4, 5, 6, 7, 8, 9, 10, 15 or about 20 mL. These values can be used to define a range, such as about 0.2 to 10 mL. In some embodiments, the monoliths can be regenerated. In other embodiments, the monolith cannot be regenerated and are intended for one-time use.

In some embodiments, the housing for the sink is not completely sealed. The housing can allow displaced air to escape as the sink fills with fluid.

The methods and compositions of the present disclosure can further include wicking a wash fluid having a volume Vw into the accumulator through any interface surface of the accumulator, wherein Vw is greater than Vac.

The wash fluid can be water or a dilute buffer. The wash fluid can be any fluid that (i) does not dislodge an appreciable amount of target analyte, and/or (ii) does not contain anything that would be considered a "contaminant" in the final output of the concentrator.

In one embodiment, a wash fluid can be any liquid that can be used to physically displace liquid such as spent fluid matrix or a previous wash fluid from the accumulator without displacing the target analyte. A wash fluid can also serve the function of dislodging or desorbing unwanted species from an accumulator element that may have adsorbed in addition to the target analyte. The final wash fluid before elution can be compatible with subsequent processes such as characterization, identification or sequencing to be performed on the target analyte. The wash fluid can be wicked into the system and can be pulled into the sink, or a wash fluid can be introduced using pressure in the same manner as the elution fluid.

The monoliths can stop wicking when the input fluid is exhausted or removed, in particular when no other external force or pressure is applied. When wicking is stopped, the monolith pores can remain filled with fluid. When a wash fluid is wicked through the accumulator it can displace the sample matrix and any non-captured or retained material or analytes. In some monoliths where mixing features have not been deliberately incorporated, the fluids do not mix or essentially do not mix as they are wicked. As such, the introduction of a wash fluid can effectively displace the sample matrix fluid from the accumulator with a wash volume that is equal to the fluid capacity of the accumulator.

To ensure complete removal of the sample matrix fluid, a wash volume of 2×, 3, 4, 5, 6, 7, 8, 9 or about 10× of the accumulator volume can be used. This can ensure that any small residual pockets are flushed. In some embodiments, greater than about 80% displacement can occur with about 2.5× the accumulator volume, and greater than about 95% displacement can occur with about 5×. For DNA extraction systems with particular monolith geometries, in some embodiments, an 8× value can provide a balance between wash effectiveness and time.

In one example, a DNA extraction uses a 200 µL lysate sample with a 25 µL fluid capacity accumulator. After the lysate is loaded, a wash fluid is used using three different 200 µL solutions. The fluid capacity of the sink is about 1800 µL. In other examples, 1, 4, or 8 mL samples can be used with either 50, 500 or 1000 µL accumulators.

The method of the present disclosure can further include uncoupling the accumulator from the sink, providing an elution fluid source, coupling the elution fluid source to any selected interface surface of the accumulator wherein the elution fluid source and the interface surface of the accumulator are in fluid communication, introducing an elution fluid having a volume Vef from the elution fluid source into the accumulator through the selected interface surface of the accumulator, wherein Vef is greater than Vac, and wherein the elution fluid releases the analyte from the accumulator, and collecting the analyte from any other interface surface of the accumulator.

After the target analyte has been loaded onto the accumulator and, if performed, washed, the accumulator and the sink can be uncoupled. Uncoupling involves eliminating the fluid communication, such as removing the physical contact, between the monolith elements. The two monoliths can be uncoupled by physically moving them apart, e.g., mechanical means. Alternatively, the coupling can include the removal of the portion of the accumulator containing the bound or captured target analyte, such as being cut and moved away. In one embodiment, a guillotine mechanism can be used, such as a blade or barrier that can be forced into the monolith to separate two portions of monolith and prevent the flow of liquid between the two separated portions during later steps of processing such as the elution step. Examples of guillotines may be a tube or a straight blade.

The uncoupling can be performed using a cutter configured to separate the accumulator and the sink and to discontinue the accumulator and sink from being in fluid communication. The separated portion can then be placed in contact with other monolith components. Alternatively the separated portion can be transferred to an elution component which ejects its fluid contents into a collection container. The accumulator element filled with target molecule can also be cut into two or more separate sections that each are transferred to supply analyte to different downstream processing systems. One of the separated components can be used as an archival medium. For example, in the case of DNA capture, the size of the excised piece of monolith can be controlled to deliver a specific amount of DNA to downstream processes that require the amount of DNA to be in a particular range. The monolith can also be divided into slices progressing away from the sample introduction face. Elution from each of these can allow for the DNA concentration to be controlled or held at a selected threshold. If there was insufficient DNA to saturate the accumulator element, only those fractions containing DNA can be selected for pooling to give the required concentration.

The separated portion, or portions, of the accumulator containing analyte can be transported using a shuttle mechanism that can break the junction between the sink monolith and the concentrator monolith. The shuttle can additionally bring a fluid reservoir and the concentrator monolith into contact and form a fluidic junction between the concentrator monolith and the outlet of the fluid reservoir. The shuttle mechanism can be a container holding the entire accumulator monolith or only a specific portion of accumulator monolith from the total fluid system. It can break or cut away a select portion of the accumulator monolith and shuttle it to one of the device components described above.

An elution fluid and an elution fluid reservoir can be provided. The elution fluid can be any fluid that can efficiently release the target analyte from the accumulator. An elution fluid can be any solution that disrupts the attractive forces between the analyte and the accumulator's interior surfaces causing the analyte to desorb or 'fall off' of the accumulator pore surfaces and be elutable. For example, DNA can be released from some of the monolith described herein with any solution having a pH greater than about 8.5. Some examples can include a 20 mM TRIS buffer having a pH of 9, or about 25 to about 200 mM ammonium hydroxide, or about 0.1 M sodium hydroxide, or a solution containing over 50% isopropyl alcohol, or over 30% ethanol, or over 1 M sodium chloride. For select antibody systems, any solution having a pH of less than about 2.8 can be used to release an antibody-bound target analyte.

In one embodiment, an elution fluid can be any liquid that can cause the target analyte to desorb from the accumulator monolith pore surfaces after capture and optional washing. The elution fluid can physically transport the desorbed target analyte out of the accumulator monolith. The elution fluid can be compatible with subsequent processes such as characterization, identification or sequencing to be performed on the target analyte. In the case where some non-analyte species remain adsorbed to the accumulator monolith, the elution fluid can preferentially cause analyte to desorb but will leave contaminant molecules adsorbed on the accumulator. The eluate can be the fluid ejected from an accumulator element as the result of introducing fluid into the accumulator element. In an elution step, the initial eluate that can be recovered from an accumulator is the fluid that was most recently introduced into the accumulator such as spent fluid matrix or a wash fluid. After a volume approximately equal to the accumulator capacity is eluted (Vac), the eluate can contain analyte and elution fluid. Eluate from a concentrator can contain purified and concentrated analyte. Eluate is the solution that can used for subsequent processes such as characterization, identification or sequencing.

The elution fluid can be contained in an elution source. The elution source can be out of fluid communication or not in fluid communication while the target analyte is being loaded and wicked into and captured by the accumulator. At some point thereafter, the elution fluid source can be coupled to any selected interface surface of the accumulator wherein the elution fluid source interface surface of the accumulator are in fluid communication The elution source, or elution fluid dispenser, can include an elution fluid reservoir, an elution fluid pressurizer and an output fitting configured to make a fluidic coupling to any interface surface of the accumulator. In one embodiment, the elution fluid dispenser is a syringe filled with the elution fluid. The syringe can be capped or otherwise not in fluid contact with the accumulator. In some embodiments, the syringe is capped with a heat-seal foil.

The elution volume from the accumulator monolith can vary depending on the size of the accumulator, the amount of analyte required, and the concentration required. The elution volume from the accumulator containing the analyte can be about, more than about, or less than about 1, 5, 10, 15, 20, 25, 30, 35, 40, 45, 50, 60, 70, 80, 90, 100, 200, 300, 400, 500, 600, 700, 800, 900 or about 1000 µL. These values can be used to define a range, such as about 20 to about 120 µL.

The elution fluid can be designed to release the target analyte from the accumulator monolith. The elution fluid can have a different pH, ionic strength, contain a specific solute, or combinations thereof. The elution fluid can also be a non-aqueous solution. The ionic strength of a solution is a measure of the concentration of ions in that solution in molality (mol/kg)

The elution fluid can have a pH value that differs from the fluid matrix of the sample fluid matrix, wash solution or both by about, or more than about, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 or about 10 pH units. These values can define a range, such as about 1 to about 3 pH units, or about 9 to about 11 pH units.

The elution fluid can have an ionic strength that differs from the fluid matrix of the sample fluid matrix, wash solution or both by about, or more than about, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 or about 10 molality (mol/kg). These values can define a range, such as about 0.5 to about 2 molality (mol/kg).

The elution fluid can have concentration of a specific solute that differs from the fluid matrix of the sample fluid matrix, wash solution or both by about, or more than about, 1, 2, 3, 4, 5, 6, 7, 8, 9, 10, 15, 20, 25, 30, 35, 40, 45, 50, 55, 60, 65, 70, 75, 80, 85, 90 or about 95 wt %. These values can define a range, such as about 30 to about 60 wt %. The specific solute can be one that has the same or higher affinity to be captured by or in the accumulator monolith, e.g., the specific solute can have a higher affinity than the target analyte to binding sites in the accumulator monolith. The specific solute can have a 2, 5, 10, 100, 1000, 10,000, 100,000, 1,000,000, 10,000,000, or about 100,000,000 fold greater affinity for binding sites in the accumulator monolith that the target analyte. The specific solute can also increase the solubility of the target analyte in the elution fluid.

The elution fluid can be introduced to, or into, the accumulator. The volume of the elution fluid can be greater than the volume capacity of the accumulator, i.e., wherein Vef is greater than Vac. Because the fluids can move through monolith in bands, a well-defined boundary between two different fluids can be created and contained within the pores of the accumulator. The analyte typically does not elute from the accumulator until the elution fluid boundary reaches the outlet. The elution fluid volume, Vef, can be about 2×, 3×, 4×, 5×, 6×, 7×, 8×, 9× or up to 10× of the accumulator monolith capacity, Vac.

After the elution fluid is introduced, the elution fluid containing the analyte is collected from a surface of the accumulator. The elution fluid can be collected after a defined amount of elution fluid has been passed into the accumulator, such as about 50, 60, 70, 80, 90, 100, 110, 120, 130, 140, 150, 160, 170, 180, 190 or about 200% of the accumulator capacity volume. These values can be used to define a range, such as about 90% to about 110%. The elution fluid can be collected in fractions over this range. The fractions can be individually tested for target analyte, and/or pooled to reconstitute the sample.

In some embodiments and similar to the determination of wicking rates, the elution fluid can contain a dye or other visible or detectable signature to indicate where the elution fluid is and when to begin collecting the elution fluid exiting the accumulator monolith.

There is no requirement that fluid be passed through the monolith in only one direction. There is also no requirement that only one type of fluid be passed through the monolith, or that there be only a single point for entry of fluid into, or a single point of exit out of, the monolith. In one embodiment, the accumulator monolith can have fluid pass through in more than one direction. A target can be captured in a first volume of fluid to pass through the monolith. The target analyte can then be modified, detected, and/or released in subsequent fluid volumes passed through the monolith in any direction, such as using multiple fluid sources and/or multiple sinks flowing in multiple directions. For example, the monolith can capture DNA by wicking a sample fluid matrix into the accumulator monolith through a first surface interface. The DNA can be eluted out of the same surface interface by passing an elution fluid into a different surface interface on the accumulator monolith, such as an opposite face or an orthogonal face. Numerous configurations of fluidic connections can be created including flipping the accumulator to introduced the sample fluid matrix to an accumulator monolith and flipping the accumulator over again to collect the eluted analyte from the same surface wherein the eluate is collected. Other configurations can include adding and removing different physical barriers from the accumulator surface interfaces, or swapping from one fluid reservoir to another on a single inlet port.

In some embodiments, the analyte fluid path through the accumulator is substantially the same, such that the analytes can be captured or retained on a portion of the accumulator and thereafter eluted in narrow band. For monoliths with multiple interfaces, the analyte inlet and elution fluid inlet can have a majority of the monolith between them.

In one example, a monolith acting as a cell-capture element may have a suspension of harvested cells introduced from the 'top' so that they are captured by the monolith while the suspending solution is washed through the accumulator element and into a sink. The sink may then be replaced with a solvent reservoir and the fluid driven through the monolith in the opposite direction such that at least some of the captured cells are ejected from the monolith. In another example, a dilute target molecule solution may be introduced from the 'top' and flowed through an accumulator element, and then eluted by fluid from a different reservoir that is attached to the 'side' of the accumulator element.

In another example, a large volume sample may be flowed through a accumulator element by introduction from the 'top' with the depleted carrier fluid absorbed by a sink element on the 'bottom' After the first sink zone is saturated with spent fluid, a second sink, or other processing zones may be attached to the 'side' of the accumulator element and additional fluid added from the 'top' or another location. In this manner, a relatively quick fluid transport rate can be maintained even after the introduction of a large volume of sample fluid has flowed through the accumulator. In addition, in this manner, analyte may be concentrated to increase the efficiency or sensitivity of subsequent steps. In yet another example, a large sample may be flowed through an accumulator element with a large volume. The captured analyte could then be eluted into a smaller accumulator element to further increase its concentration. This second accumulator element has a different type of affinity for the target analyte.

The method of the present disclosure can further include uncoupling the accumulator from the sink, providing a matrix absorber comprising a third self-wicking porous polymer monolith, the matrix absorber having an interface surface, a bypass channel, and a fluid capacity volume (Vma), wherein Vma is smaller than or equal to Vac, coupling the interface surface of the matrix absorber to any selected interface surface of the accumulator, wherein the interface surface of the matrix absorber intersects the output path of the accumulator such that it can contact and absorb the initial fluid volume Vma that elutes from the accumulator, providing an elution fluid source, coupling the elution fluid source to any other interface surface of the accumulator wherein the elution fluid source and the interface surface of the accumulator are in fluid communication, introducing an elution fluid having a volume Vef from the elution fluid source into the accumulator through any other interface surface of the accumulator, wherein Vef is greater than Vac, and wherein the elution fluid releases the analyte from the accumulator; and, collecting the analyte from the bypass channel outlet of the matrix absorber.

In some systems and compositions, a matrix absorber can be used. A matrix absorber is an additional self-wicking monolith positioned near or in contact with an outlet surface of the accumulator monolith after the sample and wash fluids have been wicked through the accumulator. Similar to the accumulator and the sink, the matrix absorber's self-wicking monolith can be any monolith that has sufficient self-wicking properties and can be formed into different geometries, or combinations thereof. For example, the monolith can be a monolith as described in U.S. patent application Ser. No. 14/549,055, the disclosure of which is incorporated by reference in its entirety. The accumulator can have an exit site that flows past or around the matrix absorber, i.e. the bypass channel, after the matrix absorber is saturated. In one embodiment, the bypass can be a tube that passes through the center of a monolith ring. In another embodiment, the matrix absorber monolith can be in contact with an outlet tube. The matrix absorber can absorb the first fluid to flow into the tube, but after it is full, all other fluid bypasses it.

The matrix absorber has a fluid capacity volume, e.g., Vma, and can have all or a portion of the Vma being unused or dry. Upon the introduction of the elution fluid to the accumulator, the matrix absorber can wick the first fluid, or soak up the first fluid, exiting the accumulator. The absorbed fluid is typically the sample matrix fluid or the wash fluid in the accumulator. During elution, the majority, if not all, of the fluid that exits the accumulator, up to Vac, contains no released analyte. After a volume of fluid, equal to or nearly equal to Vac, has exited the accumulator, a small volume of fluid elutes (eluate) containing a high concentration of the released target analyte. The small volume of fluid can be about 2, 3, 4, 5, 6, 7, 8, 9, 10, 11, 12, 13, 14, 15, 20, or about 25% of the accumulator capacity volume, or Vac. This small volume is similar to an eluted "peak" in chromatography. The fractions of fluid eluting before and after this small volume can contain much less concentrations of analyte. If these fractions containing no target analyte are collected together with the analyte peak, the target analyte is diluted. The dilution can be substantial and is undesirable if high analyte concentration is required.

In one embodiment, the matrix absorber is a volume of absorbent material made from self-wicking macroporous monolith or other suitable absorbent material. The matrix absorber can be placed in the outlet fluid path of a concentrator and can absorb a well-defined initial volume of eluate.

The matrix absorber can have at least one interface surface which can be coupled to any selected interface surface of the accumulator monolith or placed in contact with an outlet tube or channel. The fluid capacity of the matrix absorber can be less than the fluid capacity of the accumulator monolith, e.g., the fluid capacity volume (Vma) is smaller than or equal to Vac. The fluid capacity of the matrix absorber can be 110, 105, 102, 101, 100, 99, 98, 95, 92, 90, 88, 85, 82, 80 or about 75% that of the accumulator capacity. These values can define a range, such as about 80 to about 95%. The matrix absorber can have a fluid capacity of about, more than about, or less than about 5, 10, 15, 20, 25, 30, 35, 40, 45, 50, 55, 60, 65, 70, 80, 85, 90, 95, 100, 110, 120, 130, 140, 150, 200, 300, 400 or about 500 µL. These values can define a range, such as about 10 to about 30 µL. In some embodiments, the absorber can absorb fluid only until it is full. Thereafter, the matrix absorber does not absorb additional fluid and the fluid exiting the accumulator, e.g., the eluate, can flow around the matrix absorber, through the bypass channel for example, as opposed to flowing through it. The matrix absorber can also have an outlet port at the end of a bypass channel for the elution fluid, or eluate, or both that have not been absorbed, to flow around the matrix absorber after it has filled. The outlet port can be configured to allow the eluate to be transferred or flow directly into a collection vial.

Is some embodiments, the elution fluid can be introduced in more than one portion, e.g., 2, 3 4, or more portions. For example, the elution fluid can be introduced in a first portion having a volume Vef1 from an elution fluid source into the accumulator through one interface surface of the accumulator, wherein Vef1 is less than or equal to Vac. The fluid that elutes from the accumulator, i.e., is displaced from the accumulator by this first portion of elution fluid, can be absorbed in the matrix absorber and therein trapped. A second portion of elution fluid can be introduced having a volume Vef2 from the elution fluid source into the accumulator through the same or any other interface surface of the accumulator, wherein Vef1+Vef2 is greater than Vac, The fluid that elutes from the accumulator can include a small volume of fluid or eluate that contains the released target analyte that does get absorbed in the matrix absorber. The volume of eluted fluid from Vef2 that does not get absorbed in the matrix absorber can be collected from the bypass channel outlet of the matrix absorber. The eluate fraction of the fluid can also be collected.

In another embodiment, a first portion, or portions, of the elution fluid can be introduced into the accumulator to displace a similar first volume, or volumes, of fluid from the accumulator where the displaced fluid touches and can be wicked into the matrix absorber and trapped therein, wherein the first volume, or volumes, of displaced fluid can contain less than about 20, 15, 10, 5, 2 or about 1% of the analyte contained in the accumulator. A second portion, or further portions, of the elution fluid can be introduced into the accumulator to displace a second volume, or further volumes, of fluid from the accumulator, this second volume, or further volumes, can be not absorbed by the saturated matrix absorber and can therefore pass through the output of the matrix absorber, wherein the second volume, or further volumes, of displaced fluid can contain more than about 50, 60, 70, 80, 90, 95, 99 or about 100% of the analyte contained in the accumulator.

The present disclosure also relates to a concentrator. The concentrator can be a device that can accept a sample containing a target analyte as input. The output of the concentrator can be a solution containing the target analyte at a higher concentration and in a higher purity than it was present in the sample. The total amount of target analyte in the output solution can be equal to or less than the amount in the sample. The volume of the output solution can be less than the volume of the sample. The process of concentration can include manipulation of the concentrator or additional input such as wash solutions or an elution solution.

In another embodiment, the present disclosure relates to a concentrator for concentrating an analyte in a fluid matrix, the concentrator including an accumulator comprising a first self-wicking porous polymer monolith, the accumulator having a plurality of interface surfaces, and a fluid capacity volume (Vac), wherein the accumulator has an affinity for the analyte. The concentrator can further include a sink, wherein the sink comprises a second self-wicking porous polymer monolith or other suitable absorbent material, the sink having at least one interface surface, and a fluid capacity volume (Vfs), wherein the at least one interface surface of the sink and any interface surface of the accumulator are coupled together in fluid communication and configured to facilitate wicking of fluid across the coupling. The coupling between the accumulator and sink can be a mechanical junction.

Fluid junctions between monolith zones do not necessarily have to be covalent. In addition, a zone does not necessarily need to be comprised of a single piece of monolith. Monolith blocks can be held together by external compression or by interlocking geometries, e.g., See FIG. 15. The monolith surfaces within the interface can be held together such that there is physical contact along at least part of the interface surface. To achieve the maximum flow rate through the junction, the contact area should be at least equal to the cross sectional area of the smallest monolith piece at the junction. The extent of contact can be increased by using molds with smooth surfaces, which monolith pieces closely match during curing. Smooth surfaces can also be generated by other means such as cutting with blades, die cutter, laser, water knife or other methods that do not exert crushing force at the edge of the cut. The extent of contact can also be increased by using a monolith with sufficient flexibility that it will conform to the interface surface of the other monolith without crushing or other detrimental effects. By compressing an interlocking interface with a force less than what is required to fracture a given monolith formulation, the impact of any irregularities in the interface surfaces caused by mold imperfections or damage in handling can be mitigated. See, e.g., FIGS. 15 and 16 wherein the monoliths can be held together by compression.

The concentrator can further include an elution fluid reservoir configured to store elution fluid until the time of use. The reservoir can form a fluidic coupling with the accumulator monolith and being capable, when activated, of forcing elution fluid through the concentrator to elute captured target analyte. The pressured elution fluid can be delivered with a force of less than 1 or about 1, 2, 3, 4, 5, 6, 7, 8, 9, 10, 50 or about 100 psi. These values can be used to define a range, such as about 2 to about 5 psi.

The concentrator can further include an inlet and outlet, which may be the same port, for the introduction of sample and the collection of concentrated target analyte. The elution fluid dispenser can be configured to attach to the interface port of the housing and to establish fluid communication between the elution fluid reservoir and at least one interface surface of the accumulator.

The concentrator can further include a housing, sleeve or both, wherein the housing or sleeve can be configured to form a fluid-tight mechanical seal with a surface of the accumulator and having openings at two or more of the plurality of interface surfaces of the accumulator.

A monolith element may be held in a sleeve made of an elastomeric material, such as silicone rubber. The outer surface of the sleeve can be shaped to interface with the monolith enclosure. The sleeve can be made with an internal surface geometry that matches, or nearly matches, the shape of the monolithic accumulator and can include the accumulator being in contact with at least some portion of the inner surface of the sleeve along the length of the accumulator, except for the locations of at least two of the interface surfaces. The accumulator can be positioned within the sleeve such that the tip is flush or recessed in the sleeve. The accumulator-sleeve interface can be tapered and matched such that there is a tight junction between the two of them along the entire interface surface that prevents the migration of fluid around the accumulator element during use. The angle of the taper can be oriented such that any net force created upon the accumulator by the injection of pressurized fluid, such as elution fluid, can be directed such that the sleeve-monolith interface is strengthened. In other words, the accumulator can be pushed deeper into the conical shape of the sleeve and contact can be increased. The sleeve is preferably made of a material with some compliance so that, when the accumulator is pushed into the sleeve during elution with pressurized fluid, geometric irregularities in the accumulator surface will not create gaps around the accumulator that fluid could migrate through.

During elution under pressure, the accumulator can be sealed by the sleeve and/or housing such that the elution fluid inlet and eluate/elution fluid outlet are the interfaces capable of fluid flow. In some embodiments, the inlet and outlet are the only interfaces capable of fluid flow into and out of the concentrator. The strength of the seal can be such that the resistance to flow through the monolith is less than resistance to flow through any gap between the accumulator and seal. For non-pressurized flow, e.g., wicking, no sleeve or housing seal is required. In some embodiments under pressurized flow wherein a sleeve is not sealed against the accumulator, pressurized fluid can exit the accumulator. The flow can exit and reenter the accumulator closer to the outlet. Any accumulator material between the exit and re-entry point not exposed to the pressurized fluid can reduce the efficienly of the concentrator. The sleeve may be made using hydrophobic material, such as polyvinyl chloride or fluorosilicone, such that water will be less likely to migrate along the accumulator-sleeve interface.

In another embodiment, a monolith element can be held in a sleeve that is made from a material that is similar to the monolith, e.g., a polymer. In some embodiments, the sleeve is made from an incompletely cured acrylic polymer. The acrylic part can be fabricated using stereo-lithography. The polymer based sleeve can react with the monolith as it polymerizes such that the monolith and sleeve are cross-linked or mechanically interlaced when the polymerization was complete. Suitable sleeve materials could be methacrylate-based. They can be made from the same polymer as the monolith, but with low or zero solvent content. They could be made from silicone rubber, which can absorb some monomer before the monolith cures and can therefore be permeated with the acrylic polymer along the monolith-silicone boundary after the monolith is cured. The housing can be covalently bonded to the first self-wicking porous polymer monolith, or accumulator monolith.

The housing can further include an external port at, near or adjacent to one of the interface surfaces of the accumulator for receiving fluids.

In an exemplary embodiment, the accumulator is configured to selectively capture and release polynucleic acids. The capacity of the accumulator can have a capacity of at least 1 µg.

The collection container may be another piece of monolith, a vial, or the inlet of another fluidic system.

The systems and methods of the present disclosure can also be used in series or parallel. In series, a system can use one or more of the concentrators to selectively purify, concentrate, etc. one or more target analytes. For example, a first accumulator can be selective to a class of compounds. A second accumulator can be selective for a subset of the compounds. For example, a first accumulator can be selective for a target analyte but can also bind non-target analyte components. A second accumulator can be selective for the target analyte and not the non-target analyte components which bind to the first accumulator.

In another example, first and second concentrators in series can be used to achieve a higher net concentration factor, purity, etc. than a single concentrator would be capable of while still maintaining a practical sample absorption rate. In one configuration, the first accumulator can have a large $V_{ac1}$ and a relatively large cross-sectional area to allow for rapid flow rate. The first concentrator can achieve, for example, a concentration factor of 2×, 3×, 4×, 5×, 6×, 7×, 8×, 9× or about 10×. An amount of elution fluid $V_{ef1}$ smaller than the sample size can be used to elute the analyte to second accumulator. The second accumulator can have a smaller capacity volume, $V_{ac2} \ll V_{ac1}$. The second concentrator can achieve, for example a concentration factor of 2×, 5×, 7×, 10×, 15×, 20×, 30×, 40×, 50× or about 10×.

The present disclosure relates to a method for concentrating an analyte, or a class of analytes, in a fluid matrix including providing a first concentrator comprising a first self-wicking porous polymer monolith, the monolith comprising a first accumulator, the first accumulator including a plurality of interface surfaces, and a fluid capacity volume ($V_{ac1}$), providing a first sink comprising a second self-wicking porous polymer monolith, the sink having an interface surface, and a fluid capacity volume ($V_{fs1}$), coupling any interface surface of the first accumulator to the interface surface of the first sink, wherein at least one interface surface of the first accumulator and the interface surface of the first sink are in fluid communication and configured to facilitate wicking of fluid across the coupling, wicking the fluid matrix containing the analyte into the first accumulator through any interface surface of the first accumulator; and capturing the analyte in the first accumulator. The method can further include wicking the fluid matrix in excess of the Vac1 from the first accumulator into the first sink, and retaining the excess fluid matrix in the first sink. The method can also further include wicking one or more wash fluids each having a volume Vw1 into the first accumulator through any interface surface of the first accumulator, wherein Vw1 is greater than Vac1.

After the target analyte(s) has been captured by the first accumulator, the target analyte(s) can be further processed using one or more additional accumulators. The method can further include uncoupling the first accumulator from the first sink, providing a second concentrator comprising a third self-wicking porous polymer monolith, the monolith including a second accumulator and a second sink, the second accumulator including a plurality of interface surfaces, and a fluid capacity volume (Vac2), the second sink comprising a fourth self-wicking porous polymer monolith, the second sink having an interface surface, and a fluid capacity volume (Vfs2), and coupling any interface surface of the first accumulator to any interface surface of the second accumulator, wherein the interface surface of the first accumulator and the interface surface of the second accumulator are in fluid communication. The selection of the third and/or fourth self-wicking porous polymer monolith is similar to the monoliths as provided herein, including, for example, references to the fluid capacity volumes and the relative values thereof.

After the first accumulator is coupled to the second accumulator/second sink, a first elution fluid can be used to transfer the target analyte(s) to the second accumulator. The method can further include providing a source of a first elution fluid, coupling the first elution fluid source to any selected interface surface of the first accumulator, introducing (or dispensing or injecting) a first elution fluid having a volume Vef1 from the first elution fluid source through the selected interface surface of the first accumulator through the second accumulator and into the second sink, wherein Vef1 is greater than Vac1+Vac2, and wherein the first elution fluid releases the analyte from the first accumulator, and capturing the analyte in the second accumulator.

The first accumulator can thereafter be removed and the second accumulator can be optionally washed. The target analyte(s) can then be removed using a second elution fluid. The method further including uncoupling the first accumulator from the second accumulator, uncoupling the second accumulator from the second sink, providing a source of a second elution fluid, coupling the second elution fluid source to any selected interface surface of the second accumulator, introducing a second elution fluid having a volume Vef2 from the second elution fluid source into the second accumulator through the selected interface surface of the second accumulator, wherein Vef2 is greater than Vac2, and wherein the second elution fluid releases the analyte from the second accumulator, and collecting the analyte from any other interface surface of the second accumulator. The selection of the second elution fluid is similar to the first elution fluid as provided herein, including, for example, the fluid volumes and the relative values thereof.

In some embodiments, the first and the second sink can be the same sink. The sink can be coupled/uncoupled to the different accumulators. In other embodiments, the first and the second elution fluid is the same fluid. For example, the monolith binding properties may be different.

A matrix absorber can also be used. The method can further include uncoupling the first accumulator from the second accumulator, uncoupling the second accumulator from the second sink, providing a matrix absorber including a fifth self-wicking porous polymer monolith, the matrix absorber having an interface surface, a bypass channel with an outlet, and a fluid capacity volume (Vma), wherein Vma is smaller than or equal to Vac2, coupling the interface surface of the matrix absorber to any selected interface surface of the second accumulator, wherein the interface surface of the matrix absorber and the selected interface surface of the second accumulator, providing a source of a second elution fluid, coupling the second elution fluid source to any other interface surface of the second accumulator, introducing a second elution fluid having a volume Vef2 from the second elution fluid source into the second accumulator through the any other interface surface of the second accumulator, wherein Vef2 is greater than Vac2, and wherein the second elution fluid releases the analyte from the second accumulator, and collecting the analyte from the bypass channel outlet of the matrix absorber. The selection of the fifth self-wicking porous polymer monolith is similar to the monoliths as provided herein, including, for example, references to the fluid capacity volumes and the relative values thereof.

The present disclosure also relates to a method and system for concentrating an analyte in a fluid matrix including two or more concentrators or accumulators. The system can include a first accumulator including a first self-wicking porous polymer monolith, the accumulator having a plurality of interface surfaces, and a fluid capacity volume (Vac1); a first sink including a second self-wicking porous polymer monolith, the sink having an interface surface, and a fluid capacity volume (Vfs1), a second accumulator including a third self-wicking porous polymer monolith, the second accumulator having a plurality of interface surfaces, and a fluid capacity volume (Vac2), a second sink including a fourth self-wicking porous polymer monolith, the second sink having an interface surface, and a fluid capacity volume (Vfs2), wherein at least one interface surface of the first accumulator and the interface surface of the first sink, at least one interface surface of the second accumulator and the interface surface of the second sink, and at least one interface surface of the first accumulator and at least one interface surface of the second accumulator are configured to form a coupling, and wherein the first and second accumulators have an affinity for the analyte, or target analytes. The system can further include a first elution fluid configured to release the analyte from the first accumulator. The system can further include a second elution fluid configured to release the analyte from the second accumulator. Finally, the system can further include a matrix absorber, the matrix absorber having a fifth self-wicking porous polymer monolith, the matrix absorber having an interface surface, a bypass channel, and a fluid capacity volume (Vma), wherein Vma is smaller than or equal to Vac2, wherein the interface surface of the matrix absorber is configured for fluid communication with any interface surface of the accumulator of the second concentrator.

In some embodiments, the accumulator and the sink can be contained in a single monolith having different zone, i.e., an accumulator zone and a sink zone. Multi-zone monoliths, and the preparation thereof, is disclosed in U.S. patent application Ser. No. 14/549,055, the disclosure of which is incorporated by reference in its entirety.

Exemplary embodiments of the methods and the compositions are shown in the Figures.

FIG. 1A shows a block diagram of concentrator 100 made of accumulator 110 coupled to sink 120 configured to concentrate analyte from a fluid sample 150. Accumulator 110 is made of a functionalized or derivatized self-wicking porous polymer monolith having an interface surface 112, an interface surface 114 and a fluid capacity volume equal to Vac. Sink 120 is made of self-wicking porous polymer monolith having an interface surface 122 and a fluid capacity volume equal to Vfs. Fluid sample 150, consisting of analyte 152 and fluid matrix 154 is wicked into accumulator 110 via interface surface 112 and continues wicking through the accumulator 110 and into sink 120. The coupling between accumulator 110 and sink 120 is configured to facilitate wicking from the accumulator 110 to the sink 120 by a fluid sample 150 and can be held in this configuration by a compressive force.

In FIG. 1B, the analyte is captured on the internal pore surfaces of the accumulator 110. The analyte and some fluid matrix 152 are contained within the monolith pores of accumulator 110. The volume of fluid sample 150 is greater than the fluid capacity volume of accumulator 110 and is less than the fluid capacity volume Vfs of sink 120. Most of the fluid matrix wicks into the sink 120, which can be several fluid volumes larger than accumulator 110 and is typically able to absorb at least the portion of fluid matrix volume 154 exceeding the capacity of accumulator 110.

In FIG. 1C, the sink 120 is uncoupled from accumulator 110 and elution fluid 156 is injected into accumulator 110. The injection of elution fluid 156 into the accumulator 110 elutes the analyte 152 as part of output fluid 160, which also contains elution fluid 156 and fluid matrix 154. The volume of elution fluid Vef is greater than the fluid capacity Vac of accumulator 110.

FIG. 2 shows a flowchart for a method 200 of concentrating analyte for the system shown in FIGS. 1-1C. In block 202, accumulator 110 made of self-wicking porous polymer monolith having an interface surface 112, an interface surface 114 and a fluid capacity Vac is provided. A sink 120 made of a self-wicking porous polymer monolith having an interface surface 122 with a fluid capacity Vfs is also provided.

In block 204, the interface surface 114 of accumulator 110 is coupled to the interface surface 122 of the sink 120 to form a fluidic junction and forming concentrator 100. In block 206, a compressive force can be applied to form the junction.

In block 208, fluid sample 150 of volume Vs containing analyte 152 and fluid matrix 154 is wicked into concentrator 100 via interface surface 112 of accumulator 110, through the body of accumulator 110 and into sink 120, where Vs>Vac. In block 210, analyte 152 from fluid sample 150 is captured in accumulator 110 as the sample 150 passes through accumulator 110. Fluid matrix 154 in excess of accumulator 110 fluid capacity Vac is wicked into sink 120 but first passes through accumulator 110.

In block 212, sink 120 is uncoupled from accumulator 110. In block 214, a source of elution fluid 156 is coupled to any surface of accumulator 110 as shown in FIG. 1C. In block 216, elution fluid 156 of volume Vef is injected or introduced into accumulator 110 via coupling to the accumulator 110, where Vef>Vac. In block 218, analyte 152 and elution fluid 156 are ejected as output 160 from accumulator 110.

The volume of fluid sample 150 is greater than the fluid capacity Vac of accumulator 110 and less than the fluid capacity Vfs of sink 120. Most of fluid matrix 154 wicks into sink 120, which is typically several fluid volumes larger than accumulator 110 and able to absorb the fluid matrix 154 that does not settle in accumulator 110.

FIGS. 3A-3D show a block diagram of an embodiment of a system configured to concentrate analyte from a fluid sample. The description of the components and operation of FIGS. 1A and 1B also apply to FIGS. 3A and 3B.

FIG. 3C shows wash fluid 158 being dispensed into concentrator 100 via interface surface 112 resulting in wash fluid 158 displacing fluid matrix 154 out of accumulator 110 and into sink 120. After the dispensing of wash fluid 158 into concentrator 100, then sink 120 is uncoupled from accumulator 110, as shown in FIG. 3D. FIG. 3D shows elution fluid 156 being injected into accumulator 110 resulting in at least some of the analyte 152 in accumulator 110 being ejected in output 160, which will include elution fluid 156 and wash fluid 158.

Figure 4:
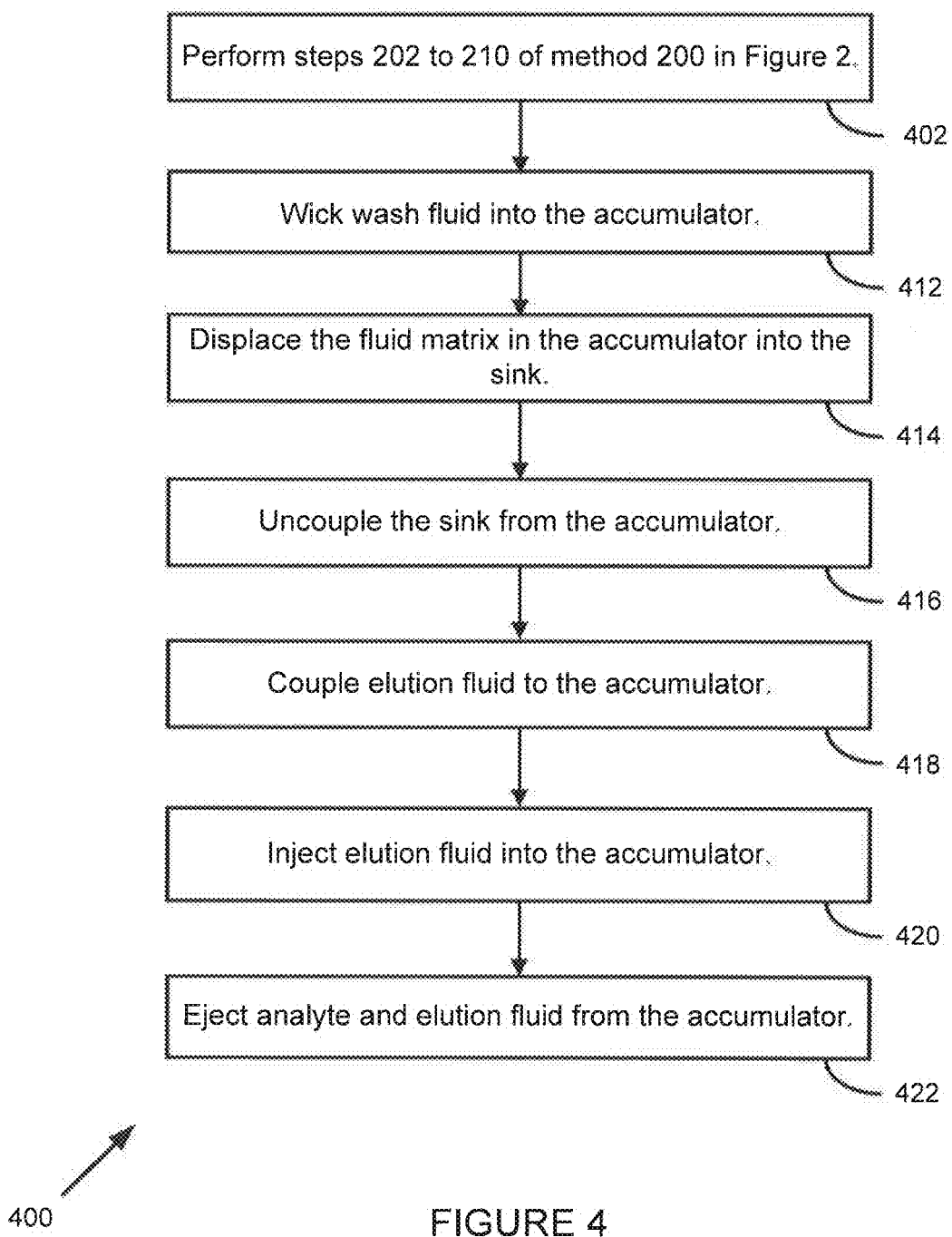
FIG. 4 shows a flowchart for an exemplary method of concentrating a target analyte in a system shown in FIGS. 3A-3D.

FIG. 4 shows a flowchart for a method 400 of concentrating analyte for the system shown in FIGS. 3A-3D. In block 402, method steps 202-210 from method 200 from FIG. 2 are performed with respect to FIGS. 3A and 3B before proceeding to block 412.

In block 410, a volume Vw of wash fluid 158 is wicked into accumulator 110 via interface surface 112, where Vw>Vac. In block 414, the fluid matrix 154 in accumulator 110 is displaced into sink 120. Wash fluid 158 in excess of accumulator 110 fluid capacity Vac is wicked into sink 120. In block 416, sink 120 is uncoupled from accumulator 110. In block 418, a source of elution fluid 156 is coupled to any surface of accumulator 110. In block 420, elution fluid 156 of volume Vef is injected into accumulator 110 via the coupling to the accumulator 110, wherein Vef>Vac. In block 422, analyte 152 and elution fluid 156 are ejected from accumulator 110.

FIGS. 5A-5D show a block diagram of an embodiment of a system configured to concentrate analyte from a fluid sample. The description of the components and operation of FIGS. 1A and 1B also apply to FIGS. 5A and 5B.

Figure 5B:
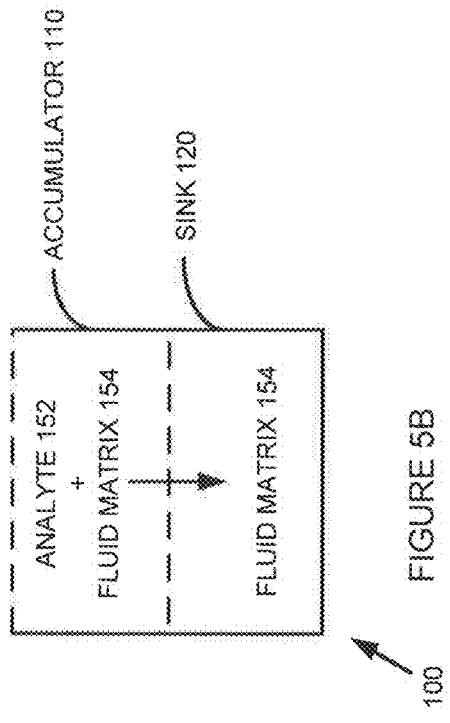
FIGS. 5A-5D show a block diagram of an embodiment of a system configured to concentrate a target analyte from a fluid sample.
Figure 5D:
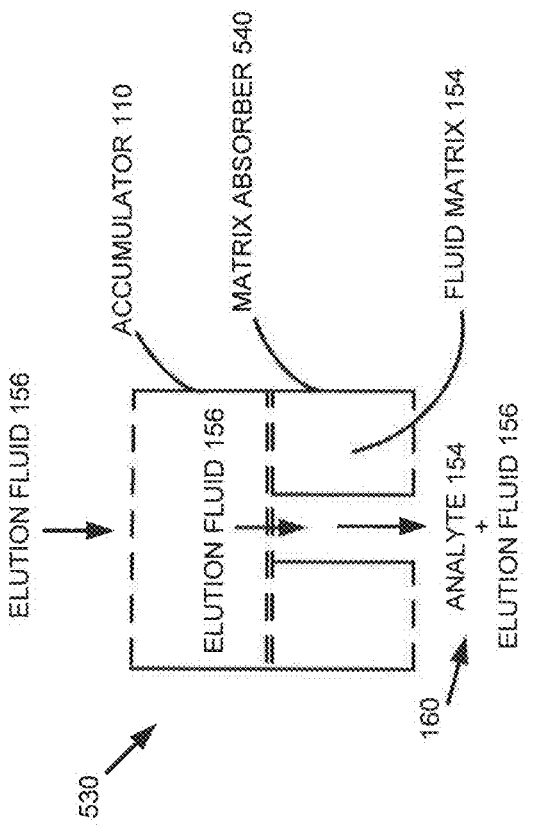
Figure 5A:
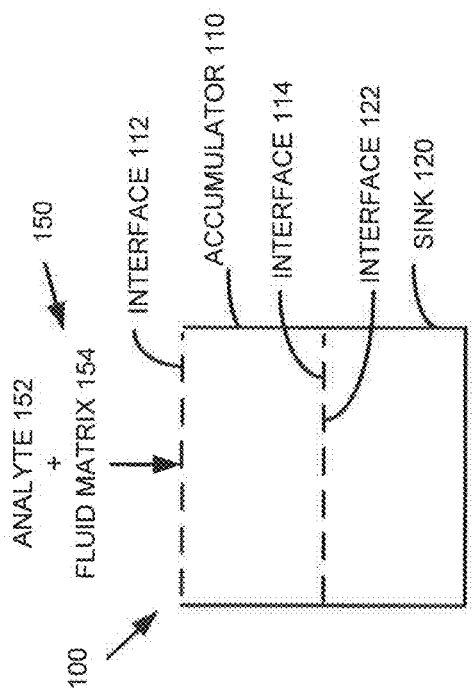
Figure 5C:
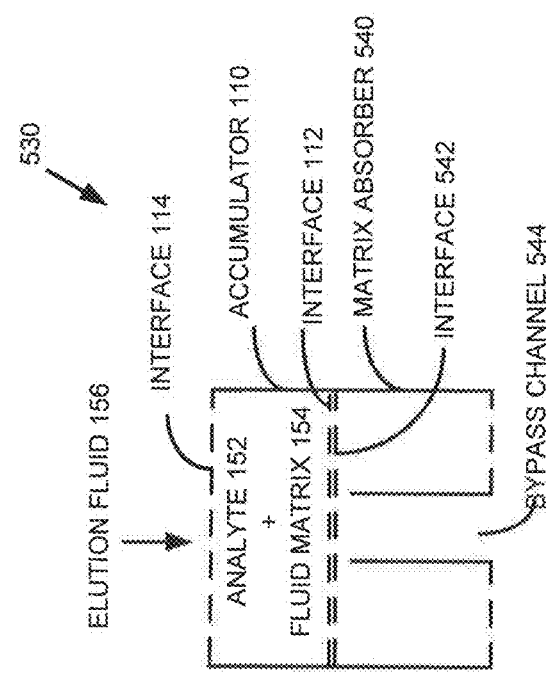

In FIG. 5C, after the capture of analyte 152 in accumulator 110 in FIG. 5B, sink 120 is uncoupled from accumulator 110. Matrix absorber 540 is made of a self-wicking porous polymer monolith having an interface surface 542 and a bypass channel 544 and forming concentrator 530. Matrix absorber 540 interface surface 542 and interface surface 112 of accumulator 110 are coupled by a fluidic junction. Elution fluid 156 is to be injected into any other surface of accumulator 110. The volume of elution fluid Vef is greater than or equal to the fluid capacity Vac of accumulator 110.

In FIG. 5D, after the injection of elution fluid 156 into accumulator 110, the elution fluid 156 displaces the fluid matrix 154 into the monolith of matrix absorber 540 and the analyte 152 and elution fluid 156 are in the output 160 via bypass channel outlet 544.

Figure 6:
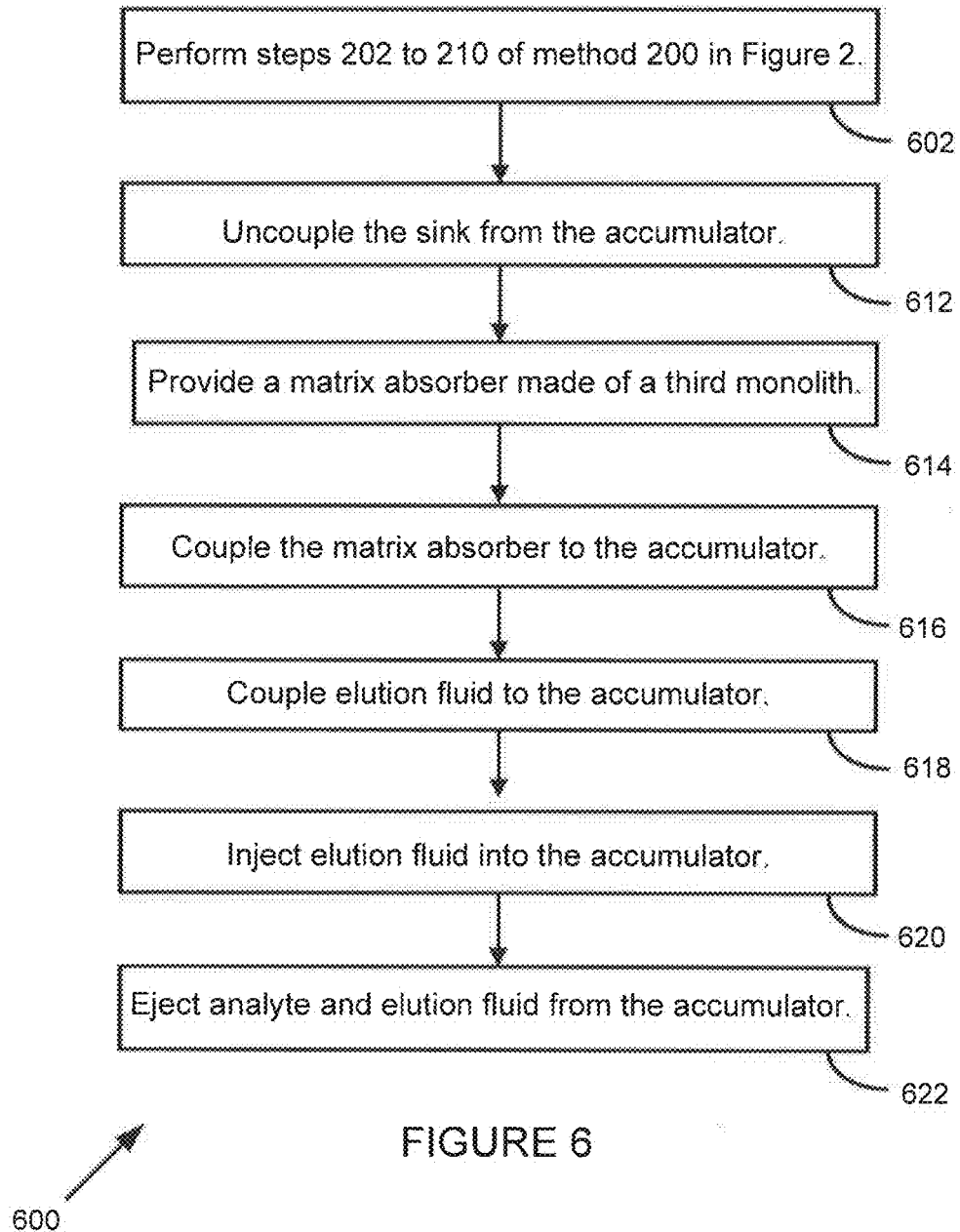
FIG. 6 shows a flowchart for an exemplary method of concentrating a target analyte in a system shown in FIGS. 5A-5D.

FIG. 6 shows a flowchart for a method 600 of concentrating analyte for the system shown in FIGS. 5A-5D. In block 602, method steps 202-210 from method 200 from FIG. 2 are performed with respect to FIGS. 5A and 5B before proceeding to block 612. In block 612, sink 120 is uncoupled from accumulator 110. In block 614, matrix absorber 540 made of a self-wicking porous polymer monolith is provided having an interface surface 542 and a bypass channel 544. In block 616, interface surface 542 of matrix absorber 540 is coupled to interface surface 112 of accumulator 110. In block 618, a source of elution fluid 156 is coupled to any other surface of accumulator 110. In block 620, elution fluid 156 of volume Vef is injected via the elution fluid coupling into accumulator 110, where Vef>Vac.

In block 622, analyte 154 and elution fluid 156 are ejected from accumulator 110 via bypass channel 544 of matrix absorber 540.

FIGS. 7A-7E show a block diagram of an embodiment of a system configured to concentrate analyte from a fluid sample. The description of the components and operation of FIGS. 1A and 1B also apply to FIGS. 7A and 7B. FIG. 7C shows wash fluid 158 being dispensed into accumulator 110. FIGS. 7D-7E show a concentrator 730 configured to include accumulator 110 coupled to matrix absorber 730. FIG. 7D shows matrix absorber 740 made of a third self-wicking porous polymer monolith having an interface surface 742 and bypass channel outlet 744. FIG. 7E shows output 160 consisting of analyte 152 and elution fluid 156 ejected from accumulator 110 via bypass channel outlet 744 of matrix absorber 740. Wash fluid 158 has been ejected from accumulator 110 into matrix absorber 740.

Figure 8:
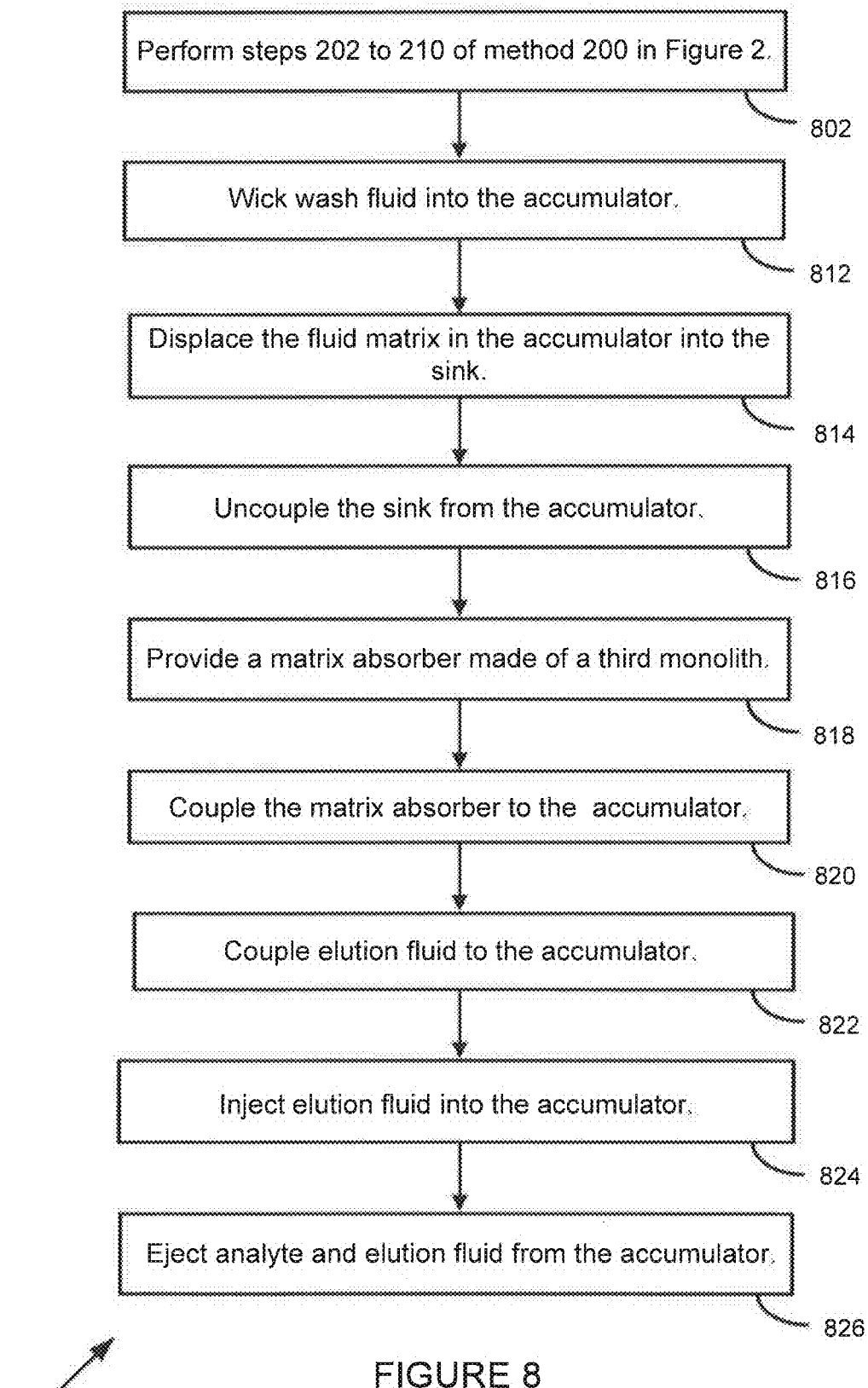
FIG. 8 shows a flowchart for an exemplary method of concentrating a target analyte in a system shown in FIGS. 7A-7E.

FIG. 8 shows a flowchart for a method 800 of concentrating analyte for the system shown in FIGS. 7A-7E. In block 802, method steps 202-210 from method 200 from FIG. 2 are performed with respect to FIGS. 7A and 7B before proceeding to block 812. In block 812, a volume Vw of wash fluid 158 is wicked into accumulator 110 via the interface surface 112, where Vw>Vac. In block 814, fluid matrix 154 in accumulator 110 is displaced into sink 120. Wash fluid 158 in excess of accumulator 110 fluid capacity Vac is wicked into sink 120. In block 816, sink 120 is uncoupled from accumulator 110. In block 818, matrix absorber 740 made of a self-wicking porous polymer monolith is provided having an interface surface 742 and a bypass channel 744. In block 820, interface surface 742 of matrix absorber 740 is coupled to interface surface 112 of accumulator 110. In block 822, a source of elution fluid 156 is coupled to any other surface of accumulator 110. In block 824, elution fluid 156 of volume Vef is injected via the elution fluid coupling into accumulator 110, where Vef>Vac. In block 826, analyte 152 and elution fluid 156 are ejected from accumulator 110 via bypass channel outlet 744 of matrix absorber 740.

FIGS. 9A-9D show a block diagram of an embodiment of a system configured to concentrate analyte from a fluid sample. The description of the components and operation of FIGS. 1A and 1B also apply to FIGS. 9A and 9B. FIG. 9C shows a first portion of elution fluid 156 to be injected into accumulator 110. FIG. 9D shows a second portion of elution fluid 156 to be injected into accumulator 110.

Figure 10:
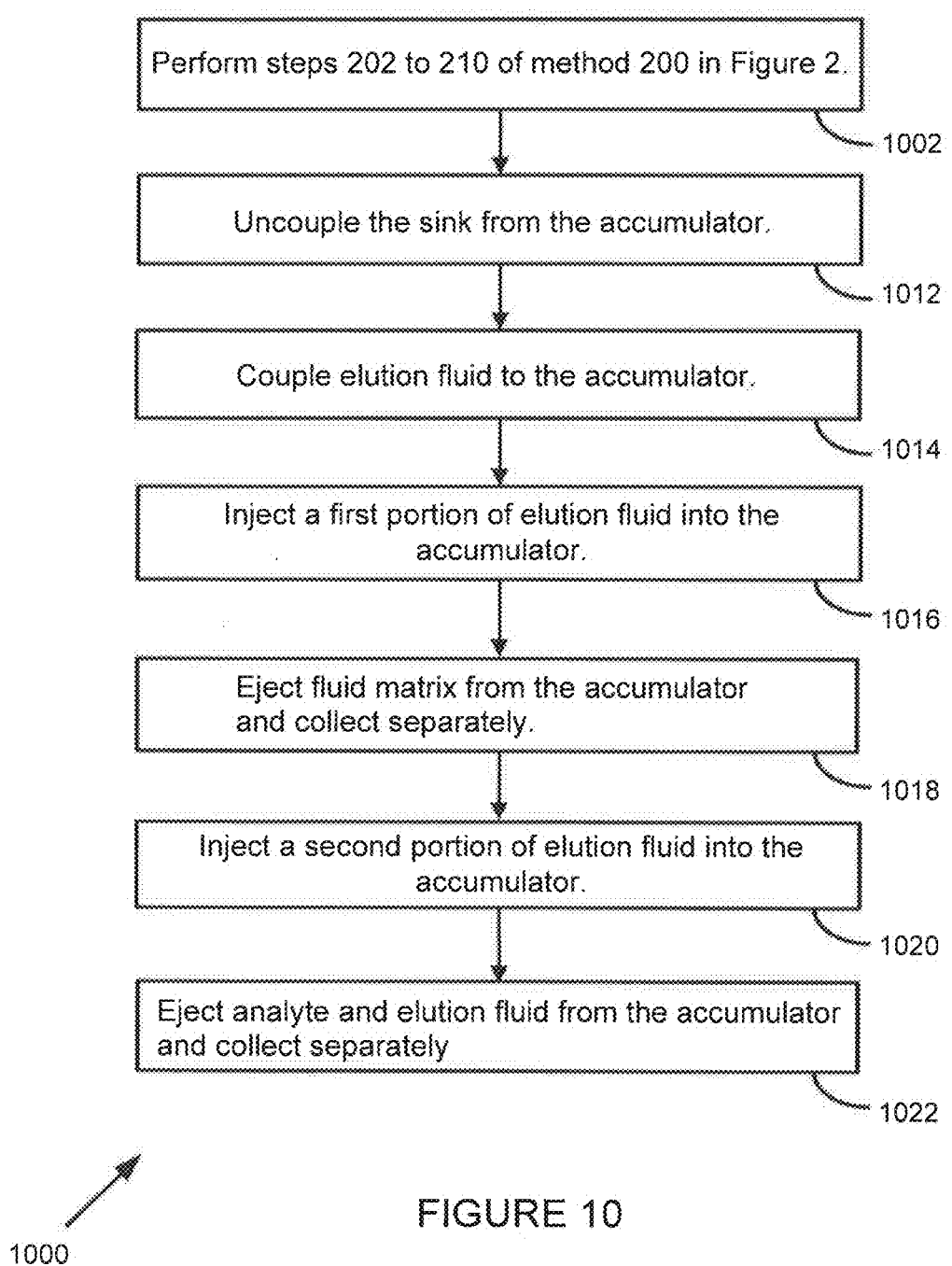
FIG. 10 shows a flowchart for an exemplary method of concentrating a target analyte in a system shown in FIGS. 9A-9D.

FIG. 10 shows a flowchart for a method 1000 of concentrating analyte for the system shown in FIGS. 9A-9D. In block 1002, method steps 202-210 from method 200 from FIG. 2 are performed with respect to FIGS. 9A and 9B before proceeding to block 1012. In block 1012, sink 120 is uncoupled from accumulator 110. In block 1014, a source of elution fluid 156 is coupled to any surface of accumulator 110. In block 1016, a first portion of elution fluid 156 of volume Vef1 is injected via the elution fluid coupling into accumulator 110, where Vef1<Vac. In block 1018, fluid matrix 154 of volume Vef1 is ejected from accumulator 110 and collected separately or discarded. In block 1020, a second portion of elution fluid 156 of volume Vef2 is injected via the elution fluid coupling into accumulator 110, where Vef1+Vef2>Vac. In block 1022, analyte 152 and elution fluid 156 with volume Vef2 is ejected from accumulator 110 and collected separately.

FIGS. 11A-11H show a series of diagrams for the operation of a system of self-wicking monoliths for analyte cleanup and concentrator.

In FIG. 11A, accumulator 110 is coupled with sink 120 to form a fluidic coupling. Accumulator housing or sleeve 1116 forms a liquid-tight seal with the loading cup 1130. Fluid sample 150 consisting of analyte 152 and fluid matrix 154 is contained in a transfer device 1140 such as a pipettor.

In FIG. 11B, fluid sample 150 is transferred into sample cup 1130 and is wicked into the inlet surface of accumulator 110. The sample 150 passes through accumulator 110, where analyte 152 is bound to the interior surfaces. Matrix fluid depleted of analyte 1151 is further wicked into sink 120. Wicking will continue until the sample fluid 150 is exhausted or until the sink 120 is full.

In FIG. 11C, when the sample cup 1130 contains no additional fluid sample 150, a wash solution 158 is added to the sample cup 1130.

In FIG. 11D, wash fluid 158 carries any matrix fluid, 1151 out of accumulator 110 and into sink 120, and leaves analyte 152 bound to accumulator 110 interior pore surfaces. As wash fluid 158 wicks into sink 120 and pushes matrix fluid 1151 further into sink 120, the portion 1159 of sink 120 closest to accumulator 110 receives wash fluid 158.

In FIG. 11E, the sample cup, 1130 is uncoupled from accumulator 110. Sink 120 is uncoupled from accumulator 110.

In FIG. 11F, accumulator 110 in housing 1116 is coupled with outlet fitting 1190 and elution fluid dispenser 1170, similar to a syringe. The elution fluid dispenser includes elution fluid 156 held in a container 1160 which can be ejected by plunger 1180. The outlet fitting 1190 is optional, but serves the role of generating small droplets that can readily be collected.

In FIG. 11G, a coupling is formed between the housing 1116 and the elution fluid dispenser 1170. A coupling is also formed between the housing 1116 and the outlet 1190, if present. In FIG. 11H, the elution fluid dispenser plunger is depressed, injecting elution fluid 156 into accumulator 110. Eluate 160 droplets form on the tip of outlet 1190 and drip into collection tube 1165.

FIGS. 12A-12H show a series of diagrams for the operation of a system of self-wicking monoliths for analyte concentration. The description and operation of the concentrator shown in FIGS. 12A and 12B is the same as previously discussed with regard to FIGS. 11A and 11B.

In FIG. 12C, sample cup 1130 is uncoupled from accumulator 110. Sink 120 is uncoupled from accumulator 110. In FIG. 12D, accumulator 110 in housing 1116 is brought into proximity with the elution fluid dispenser 1170 and the matrix absorber 1290. Elution fluid dispenser 1170 includes elution fluid 156 held in a container 1160 which can be ejected by depressing plunger 1180. The matrix absorber 1290 has a fluid capacity Vma about the same or smaller than the fluid capacity Vac of accumulator 110 and includes bypass channel 1292 (shown in FIG. 12F).

In FIG. 12E, a coupling is formed between accumulator housing 1116 and elution fluid dispenser 1170. In FIG. 12F, the outlet of accumulator 110 is coupled with the matrix absorber 1290. In FIG. 12G, elution fluid 156 is injected into accumulator 110 by depressing plunger 1180. The initial eluate contains residual matrix fluid 154 and little or no analyte 152. The initial eluate is absorbed by matrix absorber 1290 until the fluid capacity of matrix absorber 1290 is reached. In FIG. 12H, elution fluid 156 continues to be injected through accumulator 110 after matrix absorber 1290 is saturated. This eluate 160 moves through the bypass channel 1292 in matrix absorber 1290 and drips into collection tube 1265.

Figure 13:
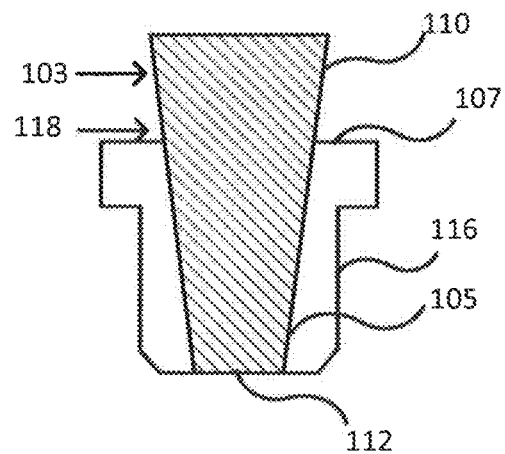
FIG. 13 shows an exemplary view of an accumulator monolith having a tapered shape in a housing or sleeve. A portion of the accumulator monolith extends past or out of one of the housing openings and can be used to form a fluidic junction with another monolith.

FIG. 13 shows a cross sectional view of an accumulator and sleeve assembly. Accumulator 110 is partially covered by sleeve 116. Fluid barrier 105 between accumulator 110 and sleeve 116 provides a liquid tight fluid barrier so that no fluid can flow in between accumulator 110 and sleeve 116. Interface surface 112 of accumulator 110 is the point of introduction for a fluid sample. Portion 103 of accumulator 110 that protrudes above the sleeve 116 is available to form a fluidic junction with a sink element or other portion of a wicking fluidic system. Portion 103 of accumulator 110 can play a mechanical role and may not capture analyte unless the amount of analyte loaded exceeds the capacity of the lower part of accumulator 110. After accumulator 110 has captured analyte from a fluid sample wicked into the accumulator via interface surface 112, then the upper portion 103 of accumulator 110 can be sheared off at break point 118, adjacent to surface 107. Surface 107 can form a fluidic seal with an elution assembly, such as the one shown in FIGS. 17A-17D, before elution fluid is injected into the top of accumulator 110.

Figure 14:
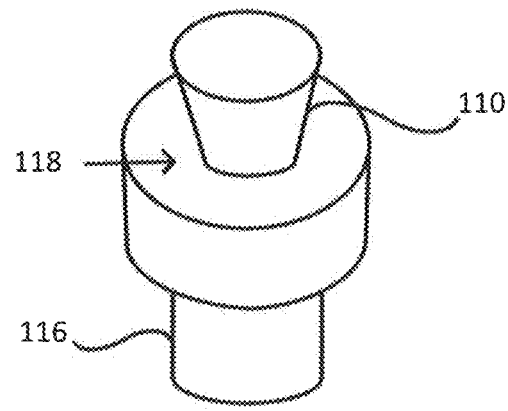
FIG. 14 shows another exemplary view of an accumulator monolith having a tapered shape in a housing or sleeve.

FIG. 14 shows a perspective view of an accumulator and seal assembly, such as the one shown in FIG. 13.

Figure 15:
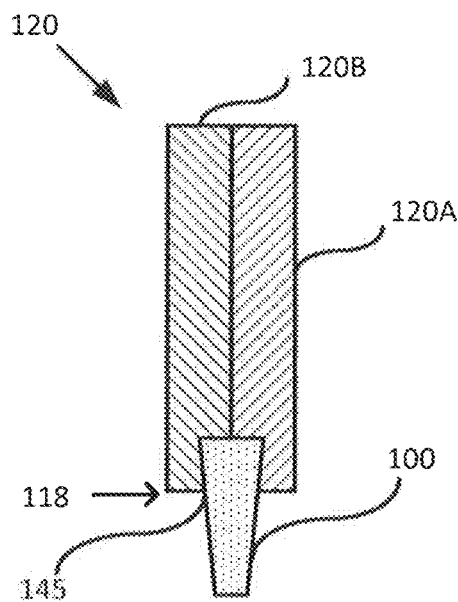
FIG. 15 shows an exemplary combination of an accumulator monolith in fluid communication with a two-piece sink monolith. A portion of the accumulator monolith extends past or out of one of the housing openings.

FIG. 15 shows a cross sectional view of a sink coupled to an accumulator, such as used in the shuttle-design concentrator of FIGS. 17A-17D. Accumulator 100 may be the same or similar to accumulator 110 shown in FIGS. 13 and 14. Junction or interface 145 is a fluidic junction between sink 120 and accumulator 100. Interface 145 requires physical contact between the separate monolith components. Fluid that wicks into accumulator 100 will continue into sink 120. As sink 120 wicks up additional fluid, it passes through accumulator 110100 before entering sink 120. Sink 120 includes section 120A and 120B. After accumulator 100 has captured analyte from a fluid sample wicked into the accumulator, then the lower portion of accumulator 100 can be sheared off at break point 118.

Figure 16:
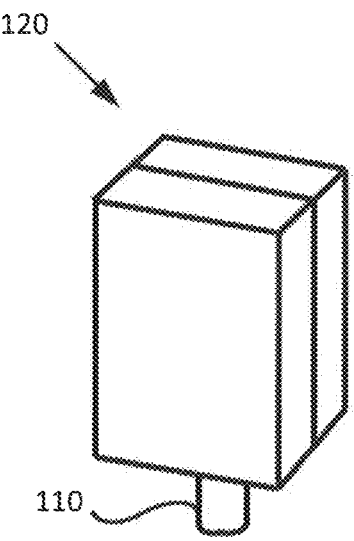
FIG. 16 shows another exemplary view of the combination of an accumulator monolith in fluid communication with a two-piece sink monolith.

FIG. 16 shows a perspective view of a sink coupled to an accumulator, such as the one shown in FIG. 15.

FIGS. 17A-17D show the elements of a self-contained wicking concentrator 1700. This single-use, disposable unit does not use electrical power. The unit is used as described in Examples 1 and 2.

Figure 17B:
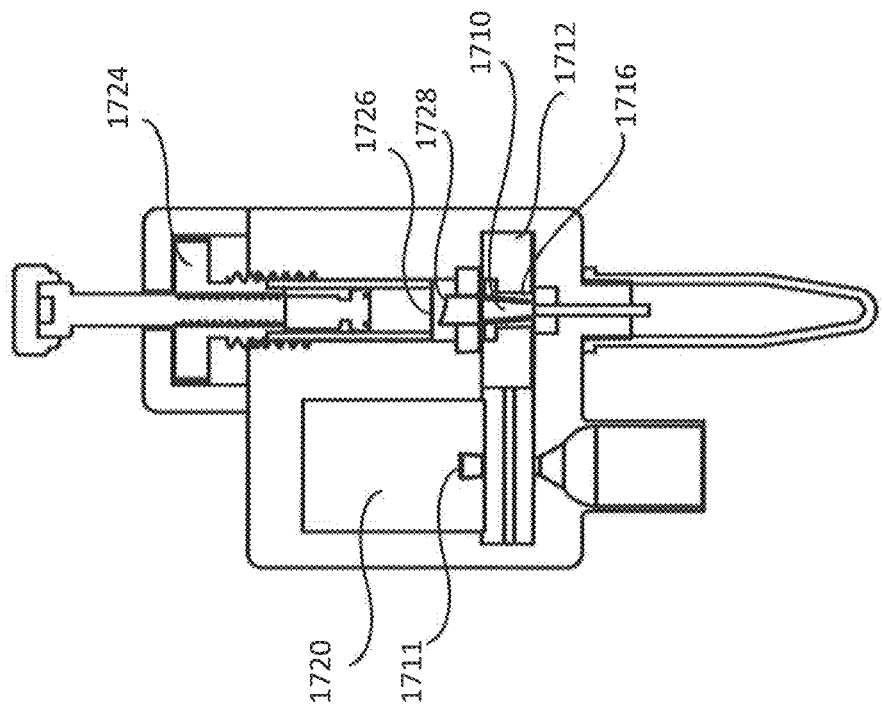
FIGS. 17A-17D show different exemplary configurations from the sequence of use protocol steps for an exemplary device containing an accumulator monolith and a sink monolith for concentrating a target analyte from a fluid sample.
Figure 17A:
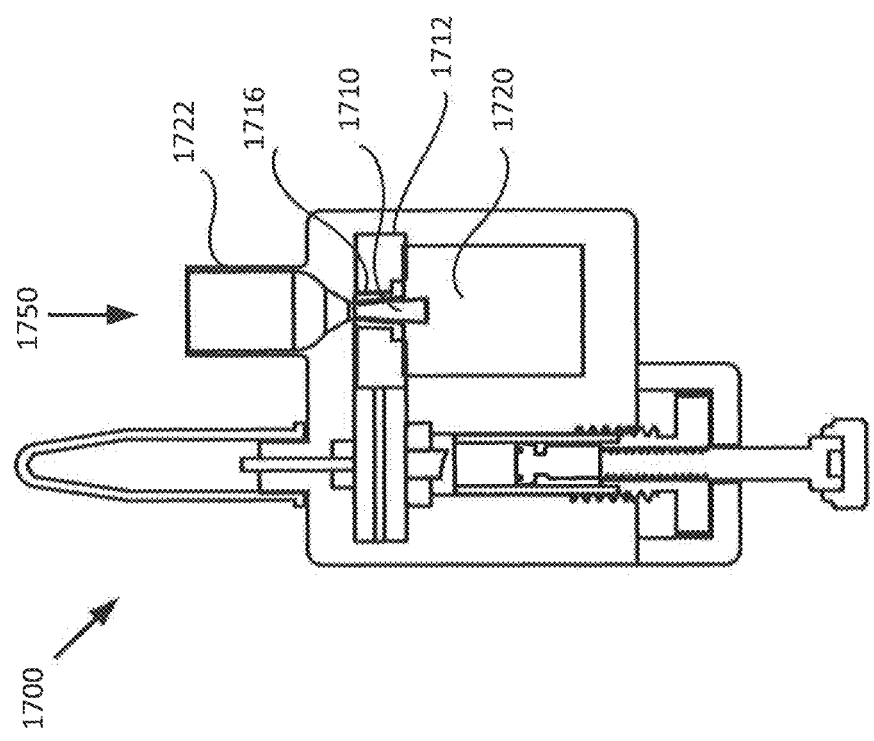
Figure 17D:
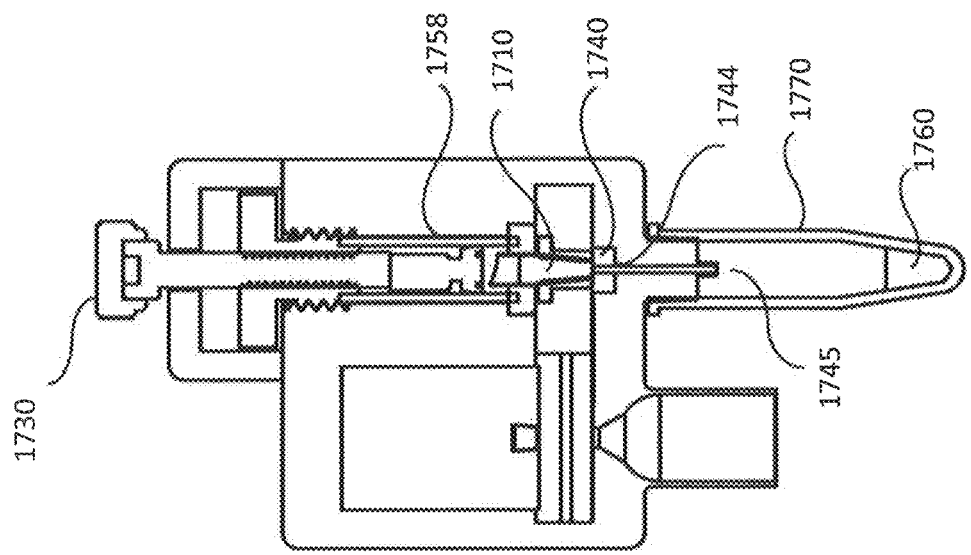
Figure 17C:
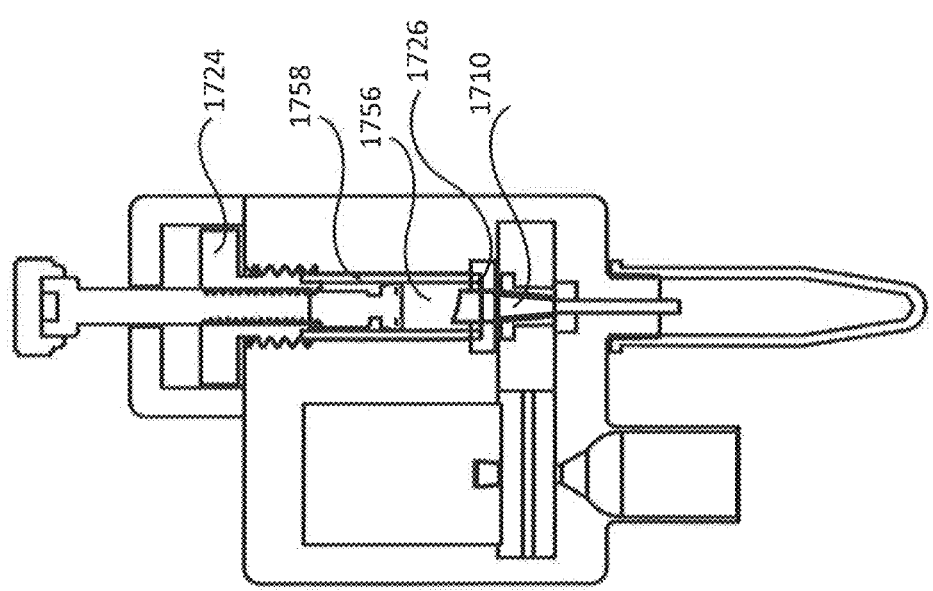

FIG. 17A shows the concentrator orientation as the sample 1750 is introduced via loading cup 1722 and absorbed through accumulator 1710 and into sink 1720. Accumulator 1710 is partially covered by sleeve 1716, and the sample cup forms a fluidic coupling with the sleeve 1716, preventing leakage of fluid sample 1750. FIG. 17B shows the system in the elution orientation with the shuttle 1712 moved from the loading position on the sink side to the elution position on the other side of the system. The accumulator 1710 has been cut into two parts. The upper portion 1711 of accumulator 1710 is still coupled to sink 1720 and is no longer involved in further processing. Pierceable seal 1726 is positioned above tubular blade 1728. Activator knob 1724 is in the upper position. FIG. 17C shows the position of the fluid reservoir after activation. The activator knob 1724 and the fluid reservoir 1758 have been lowered to seal against the sleeve 1716, and the tubular blade 1728 has pierced the pierceable seal 1726. FIG. 17D shows the system after elution is complete. The plunger assembly 1730 has been depressed to force the elution fluid 1756 through accumulator 1710. The initial eluate has also wicked into matrix absorber 1740. After the matrix absorber 1740 becomes filled with the initial eluate from the accumulator, which consists primarily of spent fluid matrix 1754, then eluate 1760 will flow through the bypass channel 1744 of matrix absorber 1740, emerge from the outlet tube 1745, and be collected in collection tube 1770.

FIGS. 18A-18D show the key design elements of a self-contained wicking concentrator 1800. This single-use, disposable unit does not use electrical power. The unit is used as described in Example 4. This design contains an alternative mechanical system to the one shown in FIGS. 17A-17D that uses a 'guillotine' mechanism to isolate the accumulator from the sink.

Figure 18B:
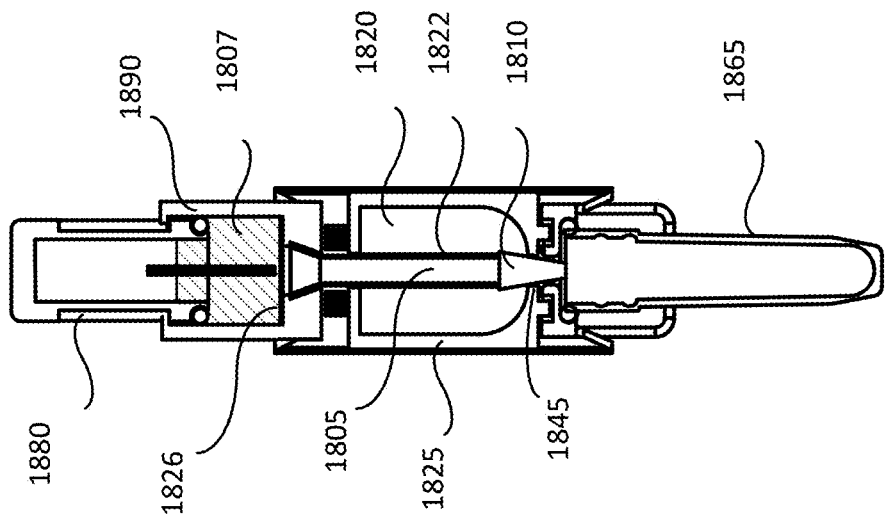
FIGS. 18A-18D show different exemplary configurations from the sequence of use protocol steps for another exemplary device containing an accumulator monolith and a sink monolith for concentrating a target analyte from a fluid sample.
Figure 18A:
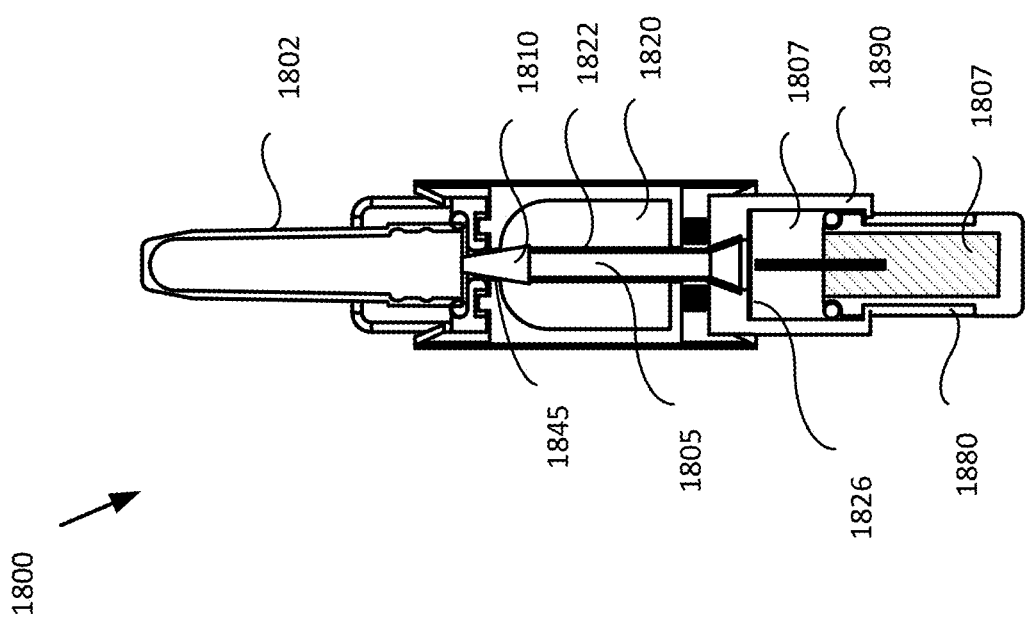
Figure 18D:
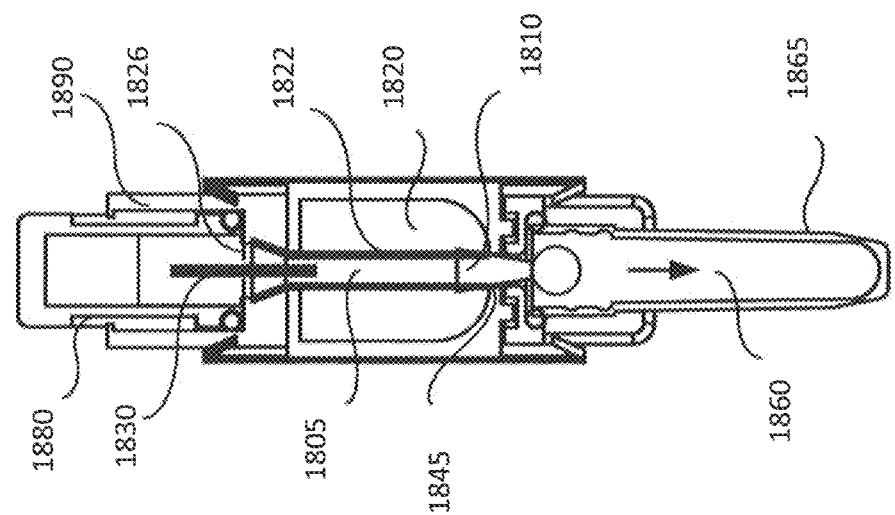
Figure 18C:
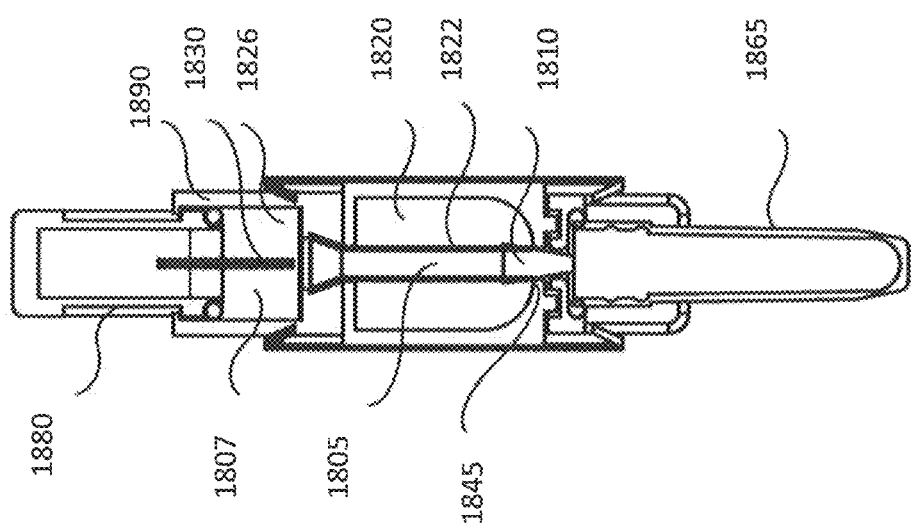

The components including 1802, sample vial; 1805, tubular steel cutter; 1807, elution fluid; 1810, accumulator; 1820, sink; 1822, hollow shaft within sink; 1820, sink; 1825 sink frame; 1826, pierceable seal; 1830, seal piercer; 1845, mechanical fluid junction; 1860, output; 1865, collection tube; 1880, plunger; and 1890, elution fluid reservoir housing. FIG. 18A shows the loading orientation after the sample, contained in the sample vial 1802, has been wicked into the device through the accumulator 1810 and into the sink 1820. FIG. 18B shows the system in the elution orientation before activation. FIG. 18C demonstrates the position of the fluid reservoir after activation. The elution fluid reservoir housing 1890 has been lowered and locked into its activated position and the tubular steel cutter 1805 has been lowered to cut through the edges of the accumulator 1810 and seal against the sink frame 1825 to form a fluidic junction 1845 that isolates the accumulator 1810 from the sink 1820. FIG. 18D illustrates the system during elution. The plunger 1880 has been depressed to force the seal piercer 1830 through the pierceable seal 1826 and to pressurize the elution fluid 1807 so it flows through the steel tubing 1805, through the accumulator 1810 and into the collection tube 1865.

FIG. 22A shows a block diagram of a first concentrator 2200 made of a self-wicking monolith accumulator 2210 and a monolith sink 2220 held together to create a fluidic junction between them. A fluid sample 2250 is introduced to the accumulator 2210.

FIG. 22B shows the state of the components after fluid sample 2250 has been wicked into the first concentrator 2200. As the fluid sample 2250 wicks through the first accumulator 2210 and into the first sink, 2220, analyte 2252 is captured in the first accumulator 2210 and the spent fluid matrix 2254 wicks into sink #1 2220.

Figure 22C:
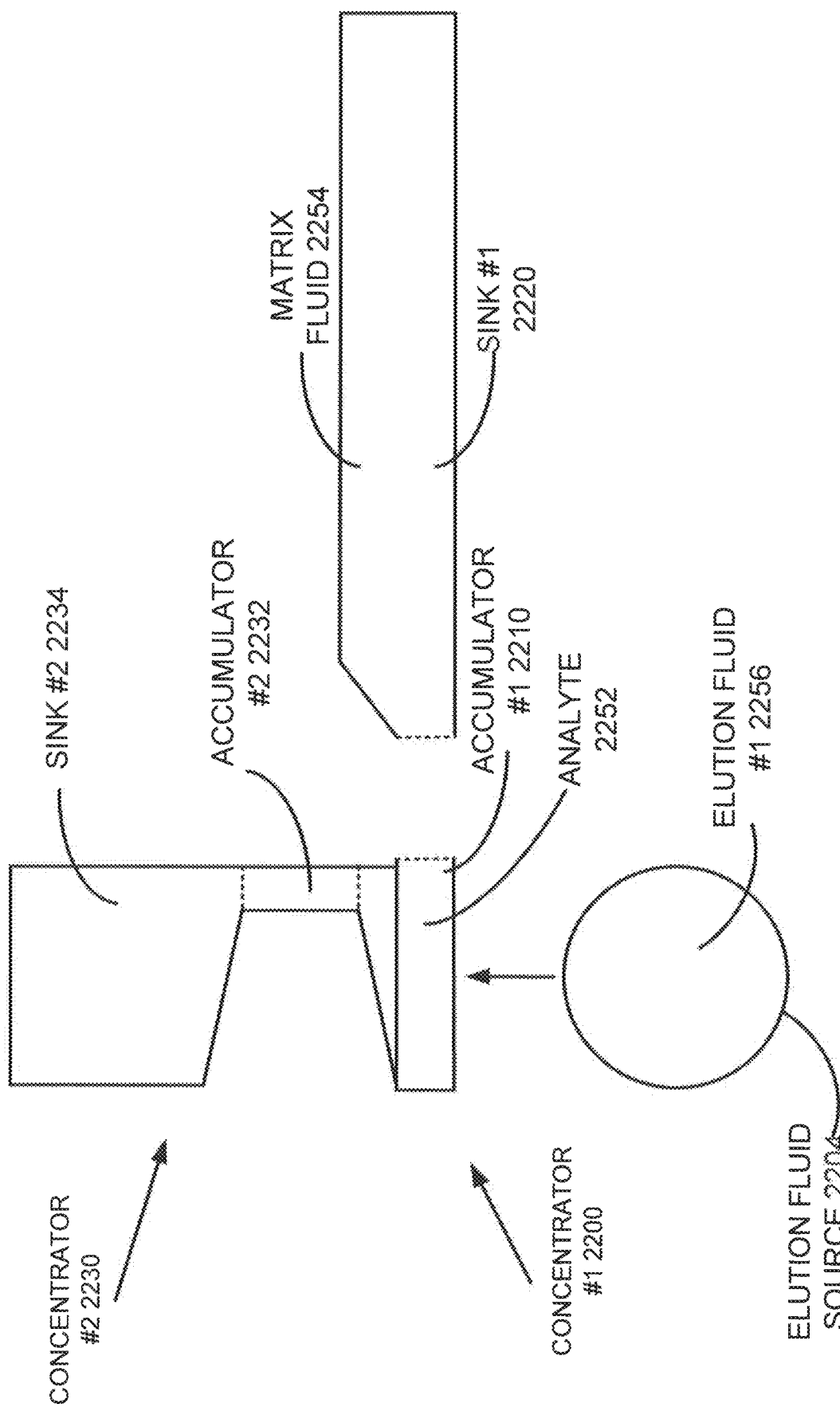

FIG. 22C shows a block diagram of a second concentrator 2230 made of a self-wicking monolith accumulator #2 2232 and a monolith sink #2 2234 held together to create a fluidic junction between them. Accumulator #1 2210 has been separated from sink #1 2220 and is coupled to concentrator #2 2230. An elution fluid source 2204 containing an elution fluid 2256 can be coupled to accumulator #1 2210.

Figure 22D:
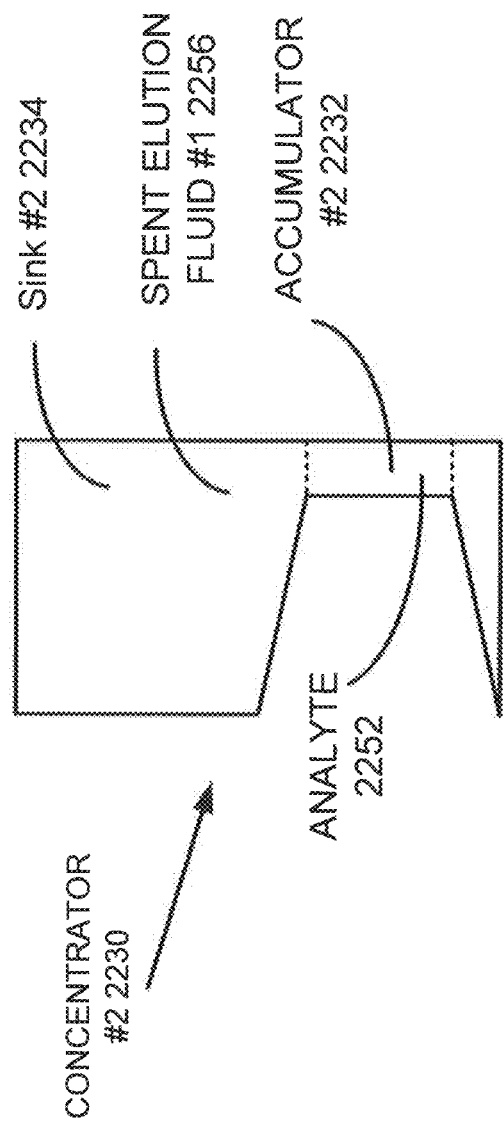

FIG. 22D shows the state of the components after elution fluid 2256 has been wicked through accumulator zone 2210 and released analyte 2252. Accumulator #1 2210 is shown removed. The analytes were carried into accumulator #2 2232 of concentrator #2 2230 and adsorbed to the pore surfaces. Depleted elution fluid 2256 continued through accumulator #2 2232 and into sink #2 2234. After the transfer of analyte 2252 into accumulator zone 2232, concentrator #2 2230 is ready for further processing, such as washing or isolation of accumulator zone 2232 by cutting it away from sink #2 2234.

Figure 23:
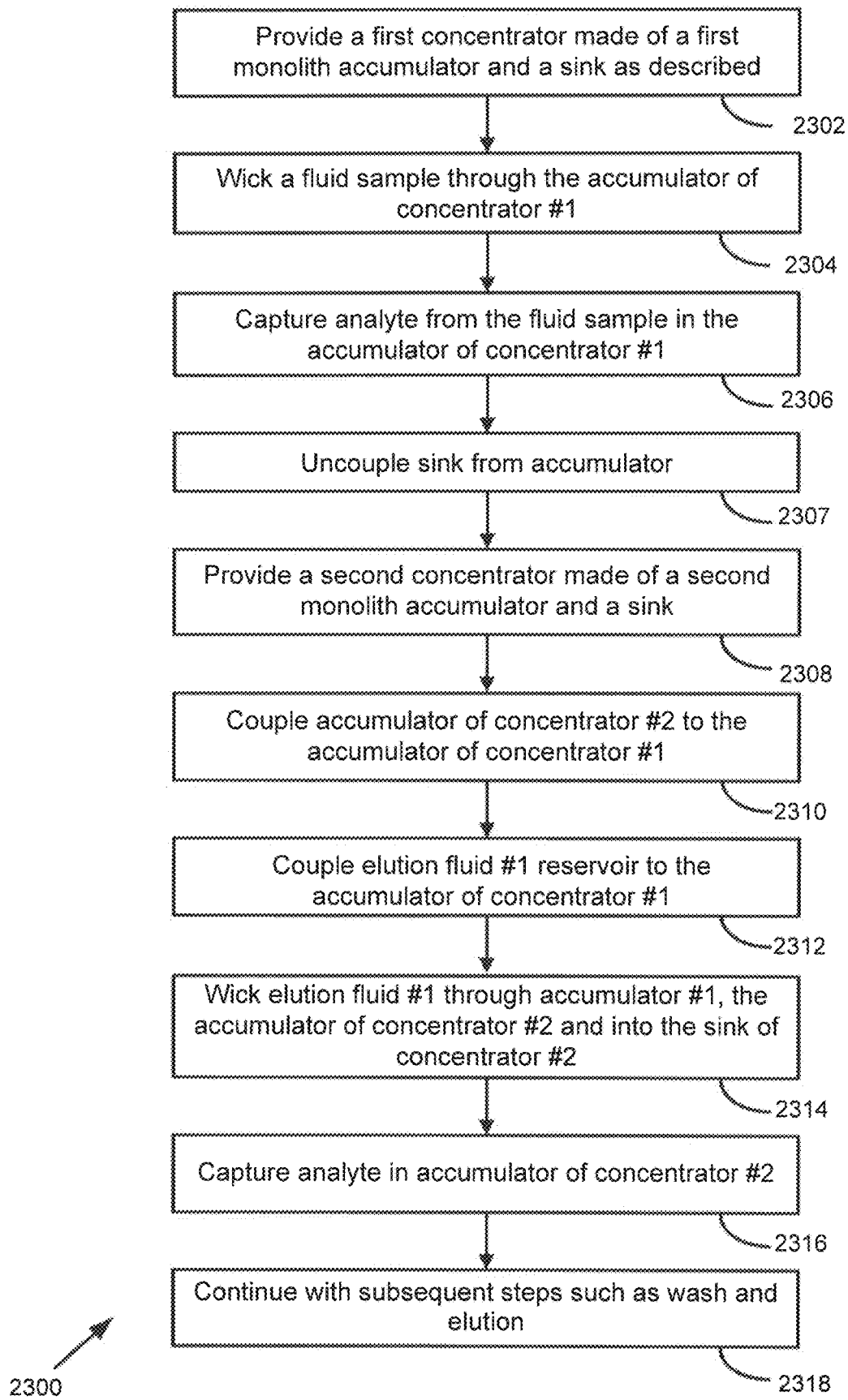
FIG. 23 shows a flowchart for an exemplary method of concentrating a target analyte in a system shown in FIGS. 22A-22D.

FIG. 23 shows an exemplary flowchart for an exemplary method 2300 of concentrating a target analyte in a system shown in FIGS. 22A-22D.

In block 2302, a first concentrator 2200 made of a first monolith accumulator 2210 and a first monolith sink 2220 are provided. In block 2304, a fluid sample 2250 is wicked through accumulator 2210 of concentrator 2200. In block 2306, a target analyte 2252 is captured from the fluid sample 2250 in accumulator 2210 of concentrator 2200. In block 2307, accumulator 2210 is uncoupled from sink 2220 and further processing can continue without sink 2220.

In block 2308, a second concentrator 2230 made of a second monolith with an accumulator 2232 and a monolith sink 2234 are provided. In block 2310, the second accumulator 2232 of concentrator 2230 is coupled to the first accumulator 2210 of the first concentrator 2200. In block 2312, a source of elution fluid 2250 is coupled to the first accumulator 2210 of concentrator 2200.

In block 2314, elution fluid 2250 is wicked through the first accumulator 2210 of concentrator 2200, through the second accumulator 2232 of the second concentrator 2230 and into the second sink 2234 of concentrator 2230. In block 2316, analyte is captured in accumulator 2232 of concentrator 2230. In block 2318, subsequent processes such as washing, isolation of the second accumulator 2232 and coupling with a second elution solution reservoir and elution, as described with respect to the other figures may be performed subsequently.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

DNA Concentration System

A DNA sample was concentrated using a manual concentrator apparatus. A 500 µL DNA sample was obtained from extraction of a buccal cell sample. The sample matrix contained 20 mM TRIS pH 7.5. The concentration of DNA in the sample was about 1 ng/µL. The sample had been prepared using an industry standard purification process. A sample volume of about 450 µL was used and concentrated using the system.

The concentrator apparatus included a concentrator cartridge for containing the accumulator monolith, etc., a cartridge stand to hold the apparatus in place (not shown for clarity), and a collection tube, as shown in FIGS. 17A-17D. The concentrator apparatus was assembled in stages. For example, the accumulator monolith was polymerized, washed, and dried in a separate process. The monolith was prepared by polymerization of a polymer mixture of EGDMA:HEMA 2:1 with 1.5% TBAMA and 1% DMAP by weight. This mixture was combined at a 1:3 ratio with a mixture of 19:1 octanol:water. 50 µl of this mixture was dispensed into a 1000 µL pipette tip that was pressed against a piece of silicone rubber to seal the outlet. The mixture was polymerized for 20 minutes under UV irradiation at a power of 0.6-0.7 mW/cm$^2$ for 20 minutes. After polymerization, the polymer was washed extensively with isopropanol, methanol and water drawn through by vacuum and then dried at −26 mM Hg vacuum at 40° C. for 16 hours. The accumulator has an affinity to DNA and can capture and retain DNA from the sample by electrostatic interaction.

The volume capacity of the accumulator monolith was about 37 µL. About 60% of the total space, e.g., 33 µL or about 25 µL of fluid capacity, was used for DNA capture. The portion of the total space used for fluid capacity can be about, more than about, or less than about 10, 15, 20, 25, 30, 35, 40, 45, 50, 55, 60, 65, 70, 80, 85, 90% or about %. These values can also define a range, such as about 50 to about 70%. The remainder of the space, if any, forms the fluid interface with the sink.

After fabrication of the accumulator monolith, it was inserted into a 40-durometer (very soft) silicone rubber sleeve. The sleeve is sufficiently soft or pliable to allow the sleeve to expand to accommodate, securely fit and seal the accumulator monolith. The sleeve was then inserted into a shuttle. The portion of the accumulator that extends beyond the sleeve will be broken away when the shuttle is used to move the accumulator from sample capture to sample elution.

The sink monolith was polymerized, washed, and dried in a separate process. The sink was fabricated in two symmetrical halves by polymerization of a polymer mixture of EGDMA:HEMA 2:1 with 1% DMAP by weight. This mixture was combined at a 1:3 ratio with a mixture of 19:1 octanol:water. 800 µL of this mixture was dispensed into an open-face fluorosilicone mold and irradiated with 365 nm UV light for 20 minutes at an intensity of about 1 uW/cm$^2$. After polymerization, the sink halves were extensively washed by soaking in IPA, and then Methanol baths. The total fluid capacity of the sink was about 1.2 mL.

The apparatus was built up by placing half of the sink in the concentrator base. The shuttle-sleeve-accumulator was then placed in the base. The portion of the accumulator that sticks out of the sleeve fits into a recess in the sink-half. The second half of the sink was placed on top, and finally a cover was glued on top of the sink & shuttle to hold it all together. FIG. 15 shows how the three monolith pieces fit together inside the rest of the apparatus. A multi-cavity sink mold was used to prepare multiple sinks at one time. The mold was made from fluorosilicone rubber of medium hardness (70 durometer, Shore A). The mold is designed to create the recesses for the tapered accumulator as two pieces of sink can be used to sandwich around the accumulator.

A matrix absorber (optional) was available, but was not used. The matrix absorber was prepared separately in the same method as the sink halves. The fluid capacity of the matrix absorber was about 20 µL. The matrix absorber, when used, can be attached to the accumulator prior to the elution fluid introduction (as shown in FIG. 12). The matrix absorber can be held in place by a compression fit in the housing or system. Alternatively, a rod-shaped monolith element with the appropriate fluid capacity (~20 µL) can be inserted into a hole drilled beside the outlet tube, as shown in FIGS. 17A-17D. If this piece of monolith is in fluid communication with the outlet tube, it can also act as a matrix absorber. The specific shape of the matrix absorber has no significant influence on its function.

The elution portion of the apparatus includes a syringe prepared by cutting the barrel and plunger from a commercial, plastic syringe. The barrel-plunger was assembled, filled with the elution fluid, and sealed with foil using an inductive heat-seal system. The filled assembly was dropped into the base. An activator was screwed down on top of it. A retainer (U-shaped piece) was glued on to keep it from being removed. Finally, the plunger was threaded through the center of the activator.

The elution fluid was 25 mM ammonium hydroxide. The syringe was filled with about 60 µL of the elution fluid. The elution fluid is designed to elute or eject the DNA from the accumulator by deprotonating the amino groups on the monolith and thereby eliminating the electrostatic attraction between charged amine groups and DNA.

FIGS. 17A-17D shows an overview of the apparatus and method. The apparatus, or cartridge, was supported on a stand with the sample cup facing up. A 450 µL aliquot of the DNA sample was combined with 50 µL loading buffer concentrate and sufficient water to bring the sample volume to 500 µL. The loading buffer was 20 mm TRIS pH 7.5, the 10× loading buffer was 200 mM TRIS pH 7.5 which was diluted 10-fold for use. The combination was loaded on to the apparatus. The sample was dispensed into the cup and was wicked through the accumulator and into the sink. The total volume of the combined sample and loading buffer was wicked through the accumulator.

The DNA present in the sample is captured by the accumulator. The "spent" sample matrix or fluid is wicked through the accumulator and into the sink. The absorption of the DNA solution took between 5 and 15 minutes. The absorption of the sample can vary depending on the volume, wicking capacity of the monolith(s) and the size of the apparatus. The sink is designed to have excess fluid capacity to ensure the sample, or combined sample and loading buffer, can be wicked into, and contained within, the sink. Once it has been absorbed, it remains within the sink and is discarded when the device is disposed of.

After the sample has been absorbed, the shuttle is moved from the loading position into the elution position. Upon this movement, the portion of the accumulator that was positioned inside of the sink breaks away from the active portion of the accumulator and remains trapped between the two halves of the sink. The portion of the accumulator that is contained within the sleeve and shuttle moves to the elution side of the apparatus. To ensure that no DNA is lost in the portion of the accumulator broken away, the accumulator capacity was higher than the amount of DNA in the sample. The capacity can be 2×, 3×, 4×, 5×, 6×, 7×, 8×, 9× or up to 10× of the expected sample amount. In doing so, the DNA that enters the accumulator gets captured by the initial monolith surface area it encounters (not already containing bound DNA).

Next, the apparatus was turned over to elute and collect the DNA. The syringe barrel was pushed down against the piercer. The foil seal was broken. The syringe barrel forms a seal against the upper surface of the sleeve (through the cutter support shown in FIGS. 17A-17D) and a sealed fluidic channel from the syringe directly to the interface surface of the DNA-filled accumulator is formed. The seal piercer is a sharp piece of steel tubing supported in a die-cut piece of silicone sheeting. Finally, the plunger actuator screw was rotated, and the elution fluid was pushed out of the syringe and through the accumulator over the course of 5-30 seconds. As the high pH elution fluid passed through the accumulator, it deprotonated the ammonium groups on the monolith and released the electrostatically-bound DNA. The concentrated DNA flowed out of the apparatus through the elution tube and was collected in the attached vial. The amount of DNA collected and eluted was about 480 ng. The concentration of eluted DNA solution was about 9.6 µg/mL, representing a concentration factor increase of about 9.6, and a yield greater than 95%. Analysis of the eluted DNA showed no significant fragmentation. The Purity of the concentrated DNA, measured by A260/A280 nm was comparable to that of the original DNA stock solution.

Example 2

DNA Concentration System Protocol

The following protocol describes the operation of a DNA Concentration System.

Protocol—Caution: Do not manipulate shuttle, activation knob or collection screw until instructed to do so. Sample should contain DNA that has been extracted and is relatively pure. The DNA binding capacity of the concentrator cartridge is 2.5 µg. These values can define a range, such as about 1 and about 5 µg.

Sample Prep. In a separate tube, add 50 µL Loading Buffer (10×) to 450 µL sample for a total of 500, or pre-dilute the Loading Buffer (10×) to 1× with nuclease-free water and use the 1× loading buffer to raise the sample volume to 500 µL. Note that DNA binding is compatible with low ionic strength buffers commonly used in DNA elution/re-suspension (TE 8.0, TRIS 8.0, water). Raising the volume of the loaded DNA to 500 µL can improve the quality of the output DNA by washing soluble contaminants more deeply into the cartridge.

In all instances the pH of the diluted sample should be ≤about pH 8.0. If uncertain, check a droplet of the sample with pH paper. The ionic strength of the loading solution should not exceed 30 mM. At 40 mM, recovery is reduced to 40% of maximum. At 50 mM, recovery is reduced to 30% of maximum.

Position each cartridge in the Loading Orientation as shown in FIG. 17A. Load the cartridge by adding 500 µL diluted sample the Sample Loading Port. Pipette up and down, without splashing, making sure no bubbles are trapped at the bottom of the Sample Loading Port.

Wait 15 minutes or until all of the sample fluid is absorbed. If fluid does not appear to be flowing, use a fresh pipette tip and attempt to dislodge bubbles in the sample loading port by gentle pipetting. After fluid is absorbed, remove cartridge from the stand and invert to the collection orientation. Slide the shuttle to the collection position until a click is felt. Turn the activation knob clockwise until it stops. Gently turn the collection screw clockwise until it stops. Fluid droplets are released into the collection tube. Remove, cap and label the tube containing the purified DNA.

Example 3

Concentration of Dilute Purified DNA

A DNA concentration device, as shown in FIG. 17A-D, having an accumulator monolith, as described in Examples 1 and 2, was used. The accumulator monolith was identical to the accumulator described in Example 1.

A 200 µL sample of 10 mM TRIS buffer, pH 7.3, containing 200 ng of human genomic DNA was placed into the receiving cup of the DNA concentrator device. The sample was allowed to absorb completely into the device. The DNA was captured and retained on the accumulator monolith.

After absorption, the shuttle containing the accumulator monolith was moved from the loading position to the elution position. This movement disconnected the accumulator monolith from the sink monolith and positioned the accumulator between the device outlet port and the elution syringe. Upon introducing the elution fluid, 50 mM TRIS buffer, pH 10, small drops of fluid emerged from the outlet and were collected in a 200 μL microfuge tube attached to the outlet port of the device. The microfuge tube was removed from the device, closed and stored.

Figure 19:
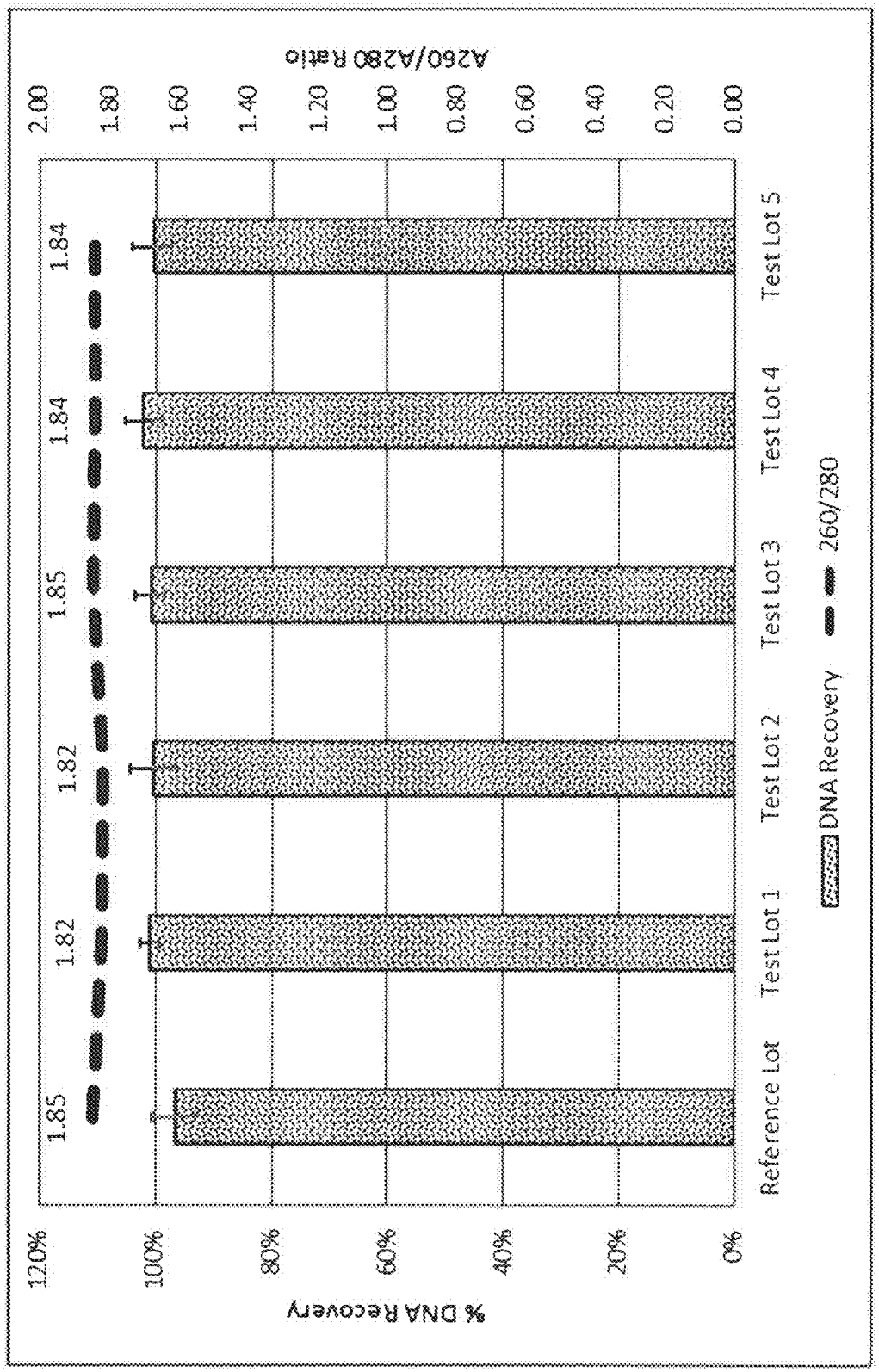
FIG. 19 shows a comparison of % DNA recovery of the same sample tested using different DNA concentration devices, as provided in Example 3.

The concentrated DNA was characterized by UV absorbance, gel electrophoresis, and quantitative PCR. Aside from the change in concentration, the data obtained from the concentrated DNA was indistinguishable from that of the original DNA. FIG. 19 shows a comparison of % DNA recovery of the same sample tested using a set of 10 of the DNA concentration devices built from each of 5 different monolith fabrication batches, for a total of 15 tests. The recovery of pure DNA is essentially quantitative for all test lots and demonstrates an A260/A280 ratio of approximately 1.8 which is the same as the ratio before application to the matrix.

Figure 20:
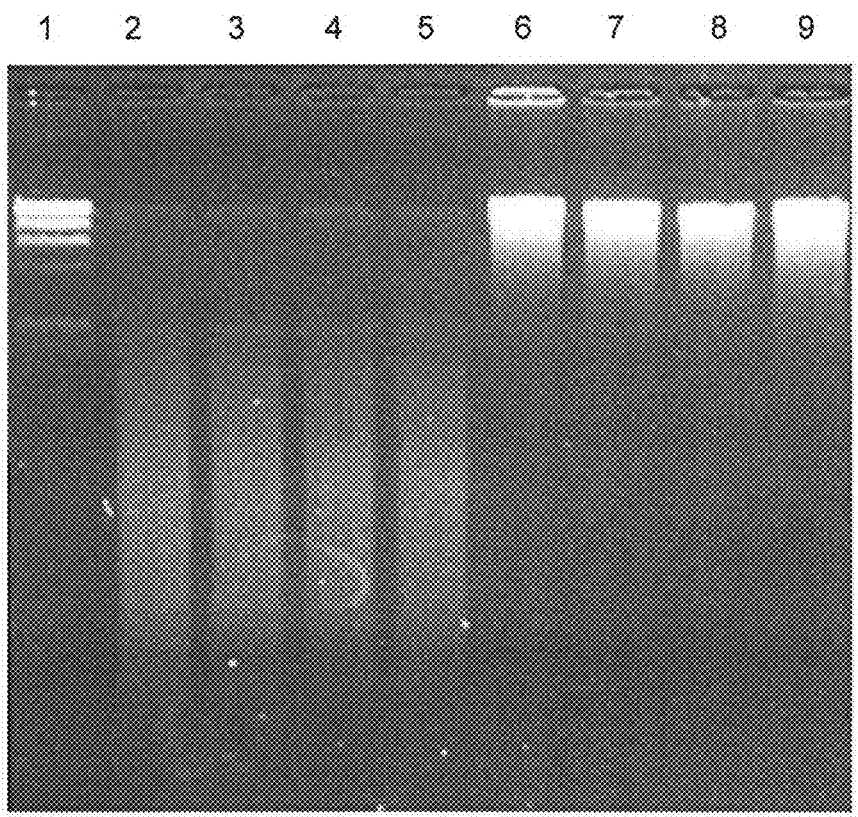
FIG. 20 shows a comparison of gel electrophoresis results for pre-loaded vs. collected DNA samples, as provided in Example 3.

FIG. 20 shows gel electrophoresis results from pre-concentration vs. 3 different collected DNA concentrates. Lane 2 is pre-concentration AluI digested DNA and lanes 3-5 are the concentrated AluI digests. No differences are observed. Lane 6 is pre-concentration BamHI digested DNA and lanes 7-9 are the concentrated BamHI digests. No differences are observed.

Figure 21:
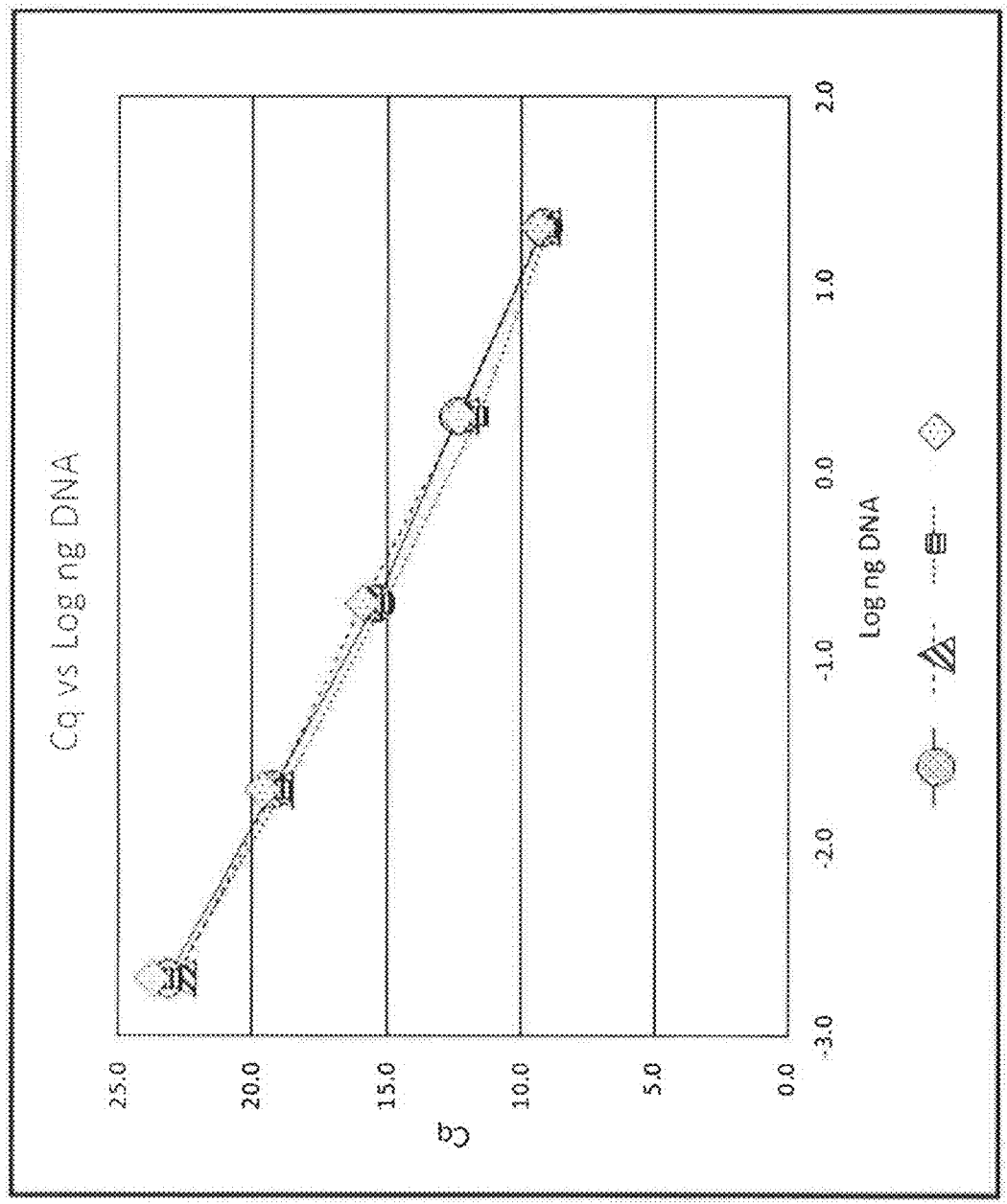
FIG. 21 shows a comparison of PCR results from collected enterobacteria phage Lambda DNA digests, as provided in Example 3.

Table 2 and FIG. 21 show the PCR results from collected Lambda DNA digests. Table 2 shows the DNA concentrated by the device amplifies the same as input DNA over 5 orders of magnitude. FIG. 21 shows a plot of Cq versus log ng of DNA, pre-concentration versus post-concentration for 3 devices. The results indicate an absence of PCR inhibitors in the concentrates and a recovery of DNA of similar quality as the input DNA.

TABLE 2

| log10 (ng of DNA Loaded) | Cq | | | |
|---|---|---|---|---|
| | Input DNA | Cartridge 1 | Cartridge 2 | Cartridge 3 |
| 1.3 | 9.2 | 9.3 | 9.0 | 9.4 |
| 0.3 | 12.3 | 12.3 | 11.6 | 12.3 |
| −0.7 | 15.4 | 15.9 | 15.2 | 15.9 |
| −1.7 | 19.2 | 19.2 | 18.8 | 19.6 |
| −2.7 | 23.1 | 22.8 | 22.9 | 23.7 |

Example 4

Alternate DNA Concentration System Configuration

A concentrator monolith system, as shown in FIGS. 18A-18D, can be used having an accumulator monolith (1810) inserted within sink monolith (1820). An empty sink frame made from acrylic with a thickness of 6 mm was clamped between two pieces of borosilicate glass. A fluid-tight plug was inserted in the outlet hole, and the frame was filled with 1600 μL sink monolith mixture containing 1:3:1 TEGDMA:EGDMA:HDEMA with 1% DMAP by weight thoroughly mixed 1:3 with a solvent solution containing 2:1 n-octanol:1,5 pentane diol. The wick rate for this material was measured to be 2.60 cm. After filling, a PVC rod was inserted in the top port of the mold and pushed down until it rested against the outlet plug. The sink (1820) was cured for 25 minutes from both sides with 365 nm UV irradiation of about 0.7 mW/cm$^2$ intensity. After curing was complete, the glass slides, rod and plug were removed. Polymerization of the sink monolith within an acrylic frame resulted in these parts being fused together. The residual solvents and any residual monomer were removed from the sink assembly by soaking in 3 consecutive isopropanol baths and then a water bath. The sink was then dried in a 60° C. vacuum oven for 24 hours.

An accumulator monolith (1810) identical to the one described in Example 1 was inserted from the top of the sink, and pushed through the internal tube created by the PVC rod until it was securely wedged into the outlet hole in the PVC frame. The maximum diameter of the accumulator is about 0.5 mm larger than the inner diameter of the tube in the sink. Because of this, the accumulator is held in contact with the sink by compression forming a mechanical fluid junction (1845).

In an alternative monolith assembly method, the cured, but unwashed, accumulator is used to plug the sink frame outlet hole. The sink monomer is then added and the PVC rod inserted. Before polymerization the sink mixture can penetrate slightly into the accumulator. When the sink is finally polymerized, it forms a crosslinked fluidic connection to the accumulator.

The elution assembly was constructed by heat-sealing a pierceable membrane (1826) to the inside of the elution fluid reservoir housing (1890). The tubular steel cutter (1805) was fabricated by sharpening one end of a stainless steel tube and flaring the other, and snapping the flare into a seat in the housing. The elution assembly was completed by filling the hollow plunger with elution fluid consisting of 30 mM TRIS buffer pH 9 and then snapping the assembled reservoir housing on to it.

The remainder of the concentrator was also designed to snap together. The peripheral components of the concentrator were snapped on to the sink-accumulator assembly as shown in FIGS. 18A-18D. Finally, the elution assembly was installed by sliding the tubular steel cutter (1805) down into the through-hole in the sink (1822) and snapping the reservoir housing (1890) into place.

FIGS. 18A-18D show an overview of the apparatus at key points in a typical method of use. A 10-1000 μL aliquot of sample containing nucleic acids, such as cell lysate, is combined with an appropriate amount of 10× loading buffer concentrate. This solution is placed in the sample tube (1802) and snapped onto the clip at the inlet. The device is then inverted to the orientation shown in FIG. 18A, and the sample falls to contact the tip of the accumulator (1810) which initiates the process of wicking the sample into the monolith assembly through the accumulator. After the sample is completely absorbed, the sample tube (1802) is filled with a wash solution (100-200 μL is a typical volume for each wash) such as 10 mM TRIS pH 7.5, snapped back on to the concentrator inlet, and wicked into the monolith through the accumulator. Additional washes with, for example, isopropanol solutions or other buffers can be performed up to a total of 1100 μL.

Once the sample has been washed, the sample vial is replaced with a clean collection vial (1865) and the concentrator is flipped into the orientation shown in FIG. 18 B. The accumulator (1810) is separated from the sink (1820) and isolated by unlocking and then moving the elution fluid reservoir housing (1890) down towards the outlet. The tubular steel cutter (1805) cuts through the periphery of the accumulator as it moves down and finally cuts into the sink frame, forming a water-tight seal. The position of this assembly after activation is shown in FIG. 18C.

Finally, the plunger (1880) is unlocked and depressed. It is locked again when it reaches the fully depressed position. This is shown in FIG. 18D. There can be an air pocket in the syringe assembly that can be compressed by movement of the plunger and served to pressurize the elution fluid (1807) to about 3 psi. The elution fluid (1807) travels down the steel tube (1805) and is forced through the accumulator by this pressure. The micron-scale pores of the accumulator prevents air from passing through the accumulator at the pressure generated within the device. Because of this, elution occurs only after the elution fluid (1807) has trickled down the steel tube and contacts the accumulator. Eluate drips out of the accumulator (1810) and into the elution tube (1865).

Example 5

Protocol for the Concentration of DNA from a Cell Lysate Sample

A concentrator monolith system can be used to purify and concentrate DNA from a cell lysate sample. The concentrator monolith can include a sink and an accumulator monolith. A sink material is provided that is identical to the material used in either Example 1 or Example 4. Similarly, either apparatus described in Example 1 or Example 4 can be used with pH 11 NaOH as the elution solution.

The accumulator monolith is fabricated from a monomer mixture of 3:17:3 TEGDA:EGDMA:HEMA with 3% TBAMA and 1.5% DMAP, by weight. This is mixed 1:3 with a solution of 90% Methanol and 10% water. 50 µL of the accumulator monomer solution is dispensed into a 1000 µL pipette tip with the outlet capped. The solution is irradiated from the top and both sides with 365 nm UV light for 20 minutes. The light intensity from the sides is about 0.6 mW/cm$^2$ and the intensity from above is about 0.4 mW/cm$^2$. The self-wicking rate of this monolith ranges from 4 to 6 cm.

For some monoliths, it was found that top illumination provided a smoother top surface. One reason may be the mold did not press against the top surface. The monoliths of the present disclosure can be irradiated on one or more of the intended surface interfaces which can be configured to couple to other materials. The monoliths of the present disclosure can also be held or contained in the mold during irradiation with one or more of the intended surface interfaces not in contact with the mold. The smoother surfaces can effect a better coupling and improved fluid communication.

DNA from buccal cells were purified and concentrated. Buccal cell collection included the following steps:
1. Dispense 350 µL, of 20 mM TRIS buffer pH 7.5 into 2.0 mL microtube.
2. Harvest buccal cells from donor by swabbing cheek for 20 s. (Puritan Purflock Ultra, Puritan Diagnostic 25-3606-U).
3. Place swab with cells into a 2 mL microtube with buffer. Break off the swab handle at the indentation and seal the tube with the swab inside. The sample may be stored for up to 1 hour before lysis.
4. When ready for extraction and concentration, vortex sample briefly (~1 s) three times at maximum and remove the swab from the tube. Squeeze out the remaining fluid using the rim of the microtube and discard.
5. Use a haemocytometer to measure cell concentration. Add buffer as needed to adjust cell counts to ~1.8-2.2×10$^6$ cells/mL before digestion.

The cell lysis included the following steps
1. Prepare 2× buccal cell lysis concentrate (20 mM TRIS pH 7.5, 15 mM EDTA, and 14.8 mAU/mL Proteinase K). 100 µL mixture per extraction.
2. Dispense 100 µL of buccal cells sample (~2.0×10$^6$ Buccal Cells/mL) to digest plate (96 well plate) or other suitable container.
3. Add 100 µL of 2× buccal cell lysis concentrate and mix by pipetting three times up and down.
4. Securely Seal the samples with tube caps or adhesive plate sealer. Double check each seal.
5. Incubate sealed plate at 55° C. for 30 minutes on a thermal cycler.

The DNA capture and concentration included the following steps
1. Transfer each lysate to sample tube after mixing with pipette.
2. Attach sample tube to concentrator unit and invert.
3. Allow sample to wick into concentrator, approximately 5 minutes.
4. Wash with wash solution 1 by removing the sample tube, adding 200 µL of wash 1 solution (30 mM TRIS pH 7.6), then attaching the sample tube to concentrator unit and inverting, and allowing the wash to wick into the concentrator.
5. Wash with wash solution 2 by removing the sample tube, adding 200 µL of wash 2 solution (20% IPA, 30 mM MOPS pH 7.6), then attaching the sample tube to concentrator unit and inverting, and allowing the wash to wick into the concentrator.
6. Repeating the wash with wash solution 1.
7. Replace the sample tube with a clean collection tube.
8. Activate the elution system by removing the safety pin and twisting the reservoir housing clockwise until it stops.
9. Elute the sample by twisting the elution system plunger/turn clockwise and depressing until it clicks into place.
10. Wait at least 2 minutes for elution to complete. Hold the concentrator upright during elution, laying it on its side can stop the elution process. If elution stops, it can be resumed by returning the concentrator to an upright position and/or gently tapping the side of the concentrator to free any internal bubbles that may be blocking flow.
11. Seal, label and store the concentrated DNA.

The DNA quality can be evaluated by the following steps
1. Measuring the DNA concentration using Quantifluor or a comparable fluorescent dye. The concentration should be between 1 and 2 micrograms of DNA.
2. Measuring the purity of the DNA using the A260/A280 ratio. The ratio should be between 1.8 and 2.0.
3. If desired, the DNA fragmentation can be measured by agarose gel electrophoresis. There can be a dominant high molecular weight band with traces of smaller fragments that are formed during the digestion step.
4. Evaluating PCR inhibition by testing a housekeeping gene with serial dilutions in a standard qPCR protocol. Use about 2.5 µL DINA concentrate per 25 µL reaction. Use a 2, 3, or 10× serial dilution. The slope should can be between −3.1 to −3.6. If the slope is not within this range, repeat after heating PCR aliquots to 95° C. for 5 minutes before adding to PCR master mix.

While this disclosure has been particularly shown and described with reference to example embodiments thereof, it will be understood by those skilled in the art that various changes in form and details may be made therein without departing from the scope of the invention encompassed by the appended claims.

We claim:

1. A method for concentrating a negatively charged analyte in a fluid matrix, the method comprising:
providing an accumulator comprising a first self-wicking porous polymer monolith, the accumulator having:
a plurality of interface surfaces;
an accumulator fluid capacity volume (Vac); and
an affinity for negatively charged analyte;
providing a sink comprising a second self-wicking material, the sink having:
an interface surface configured for fluidic communication with any one of the plurality of interface surfaces of the accumulator; and
a sink fluid capacity volume (Vfs), wherein the sink fluid capacity volume (Vfs) is greater than the accumulator fluid capacity volume (Vac);
coupling a selected one of the plurality of interface surfaces of the accumulator to the interface surface of the sink;
wicking the fluid matrix containing the negatively charged analyte into the accumulator through any other interface surface of the accumulator;
capturing the negatively charged analyte in the accumulator by electrostatic attraction;
wicking the fluid matrix in excess of the accumulator fluid capacity volume (Vac) from the accumulator into the sink;
uncoupling the accumulator from the sink; and
eluting the negatively charged analyte from the accumulator without using a wash fluid to remove fluid matrix out of the accumulator.

2. The method of claim 1, wherein the first self-wicking porous polymer monolith has a self-wicking rate of at least 1 cm.

3. The method of claim 1, wherein the second self-wicking material is a porous polymer monolith.

4. The method of claim 1, wherein the second self-wicking material has a self-wicking rate of at least 1.8 cm.

5. The method of claim 1, further comprising:
retaining the excess fluid matrix in the sink.

6. The method of claim 1, wherein the coupling of the accumulator and the sink comprises compressing the accumulator and sink together to form a mechanical junction.

7. The method of claim 1, wherein eluting comprises:
coupling the elution fluid source to any selected interface surface of the accumulator wherein the elution fluid source and the selected interface surface of the accumulator are in fluid communication;
introducing an elution fluid having an elution fluid volume (Vef) from the elution fluid source into the accumulator through the selected interface surface of the accumulator, wherein the elution fluid volume (Vef) is greater than the accumulator fluid capacity volume (Vac), and wherein the elution fluid releases the analyte from the accumulator; and
collecting the negatively charged analyte from any other interface surface of the accumulator.

8. The method of claim 1, wherein eluting comprises:
providing a matrix absorber comprising a third self-wicking material, the matrix absorber having:
an interface surface,
a bypass channel with an outlet, and
a matrix absorber fluid capacity volume (Vma), wherein the matrix absorber fluid capacity volume (Vma) is smaller than or equal to the accumulator fluid capacity volume (Vac);
coupling the interface surface of the matrix absorber to any selected interface surface of the accumulator, wherein the interface surface of the matrix absorber and the selected interface surface of the accumulator are in fluid communication;
providing an elution fluid source;
coupling the elution fluid source to any other interface surface of the accumulator wherein the elution fluid source and the any other interface surface of the accumulator are in fluid communication;
introducing an elution fluid having an elution fluid volume (Vef) from the elution fluid source into the accumulator through the any other interface surface of the accumulator, wherein the elution fluid volume (Vef) is greater than the accumulator fluid capacity volume (Vac), and wherein the elution fluid releases the analyte from the accumulator; and
collecting the analyte from the bypass channel outlet of the matrix absorber.

9. The method of claim 1, wherein eluting comprises:
providing a matrix absorber comprising a third self-wicking material, the matrix absorber having:
an interface surface,
a bypass channel with an outlet, and
a matrix absorber fluid capacity volume (Vma), wherein the matrix absorber fluid capacity volume (Vma) is smaller than or equal to the accumulator fluid capacity volume (Vac);
coupling the interface surface of the matrix absorber to any selected interface surface of the accumulator, wherein the interface surface of the matrix absorber and the selected interface surface of the accumulator are in fluid communication;
providing an elution fluid source;
coupling the elution fluid source to any other interface surface of the accumulator wherein the elution fluid source and the any other interface surface of the accumulator are in fluid communication;
introducing a first portion of an elution fluid having a first elution fluid volume (Vef1) from the elution fluid source into the accumulator through the any other interface surface of the accumulator, wherein the first elution fluid volume (Vef1) is less than the accumulator fluid capacity volume (Vac),
introducing a second portion of an elution fluid having a second elution fluid volume (Vef2) from the elution fluid source into the accumulator through the any other interface surface of the accumulator, wherein the first elution fluid volume (Vef1)+second elution fluid volume (Vef2) is greater than the accumulator fluid capacity volume (Vac), and wherein the elution fluid releases the analyte from the accumulator; and
collecting the analyte from the bypass channel outlet of the matrix absorber.

10. The method of claim 9, wherein the first portion of the elution fluid introduced into the accumulator displaces a first volume of fluid from the accumulator to the matrix absorber wherein the first volume of displaced fluid contains less than about 10% of the analyte contained in the accumulator.

11. The method of claim 9, wherein the second portion of the elution fluid introduced into the accumulator displaces a second volume of fluid from the accumulator through the output of the matrix absorber, wherein the second volume of displaced fluid contains more than about 50% of the analyte contained in the accumulator.

12. The method of claim 1, wherein at least a portion of the accumulator surface is sealed to prevent the passage of fluid out of the accumulator.

13. A concentrator for concentrating a negatively charged analyte in a fluid matrix, the concentrator comprising:
- an accumulator comprising a first self-wicking porous polymer monolith, the accumulator having:
  - a plurality of interface surfaces;
  - an accumulator fluid capacity volume (Vac); and
  - an affinity for the negatively charged analyte by electrostatic attraction;
- a sink comprising a second self-wicking material, the sink having:
  - at least one interface surface configured for fluidic communication with any one of the plurality of interface surfaces of the accumulator; and
  - a sink fluid capacity volume (Vfs), wherein:
    - the sink fluid capacity volume (Vfs) is greater than the accumulator fluid capacity volume (Vac);
    - the at least one interface surface of the sink and a selected one of the plurality of interface surfaces of the accumulator are coupled together in fluidic communication; and
    - the sink is configured to facilitate wicking of the fluid matrix in excess of accumulator fluid capacity (Vac) from the accumulator into the sink.

14. The concentrator of claim 13, wherein the accumulator is a tapered cylinder shape.

15. The concentrator of claim 13, wherein the second self-wicking material is a porous polymer monolith.

16. The concentrator of claim 13, wherein the coupling between the accumulator and sink comprises a mechanical junction.

17. The concentrator of claim 13, further comprising a housing, wherein the housing is configured to form a fluid-tight mechanical seal with a surface of the accumulator and having openings at one or more of the plurality of interface surfaces of the accumulator.

18. The concentrator of claim 17, wherein the housing is covalently bonded to the first self-wicking porous polymer monolith.

19. The concentrator of claim 17, wherein the housing has a hollow tapered cylinder shape.

20. The concentrator of claim 17, wherein the housing further comprises an external port at one of the interface surfaces of the accumulator for receiving fluids.

21. The concentrator of claim 13, further comprising an elution fluid dispenser, the elution fluid dispenser having:
- an elution fluid reservoir; and
- an elution fluid pressurizer;
- wherein the elution fluid dispenser is configured to attach to the external port of the housing and to establish fluid communication between the elution fluid reservoir and one of the at least one interface surface of the accumulator.

22. The concentrator of claim 13, further comprising a cutter, wherein the cutter is configured to separate the accumulator and the sink, wherein upon separation the accumulator and sink are no longer in fluid communication.

23. The concentrator of claim 13, further comprising a matrix absorber, the matrix absorber comprising a third self-wicking material, the matrix absorber having:
- an interface surface,
- a bypass channel with an outlet, and
- a matrix absorber fluid capacity volume (Vma), wherein the matrix absorber fluid capacity volume (Vma) is smaller than or equal to the accumulator fluid capacity volume (Vac);
- wherein the interface surface of the matrix absorber is configured for fluid communication with any interface surface of the accumulator.

24. The method of claim 1, wherein the negatively charged analyte comprises at least one of: lipid-membrane fragments, DNA, nucleic acids and proteins.

25. The method of claim 1, wherein the accumulator can capture and retain DNA from the fluid matrix.

26. The method of claim 1, wherein the accumulator comprises amino groups to capture the negatively charged analyte.

27. The method of claim 26, wherein the eluting releases the negatively charged analyte from the accumulator by deprotonating the amino groups on the accumulator and thereby eliminating the electrostatic attraction between the amino groups and the negatively charged analyte.

28. The method of claim 1, wherein the eluting disrupts the electrostatic attraction between the negatively charged analyte and the accumulator.

29. The concentrator of claim 13, wherein the negatively charged analyte comprises at least one of: lipid-membrane fragments, DNA, nucleic acids and proteins.

30. The concentrator of claim 13, wherein the accumulator can capture and retain DNA from the fluid matrix.

31. The concentrator of claim 13, wherein the accumulator comprises amino groups to capture negatively charged analyte.

32. The concentrator of claim 31, wherein the elution fluid is formulated to release the negatively charged analyte from the accumulator by deprotonating the amino groups on the accumulator and thereby eliminating the electrostatic attraction between the amino groups and the negatively charged analyte.

33. The concentrator of claim 13, wherein the elution fluid is formulated to disrupt the electrostatic attraction between the negatively charged analyte and the accumulator.

* * * * *